United States Patent
Cunningham et al.

(10) Patent No.: US 11,834,709 B2
(45) Date of Patent: Dec. 5, 2023

(54) MULTIPLEXED TARGET-BINDING CANDIDATE SCREENING ANALYSIS

(71) Applicant: Genentech, Inc., South San Francisco, CA (US)

(72) Inventors: Christian N. Cunningham, South San Francisco, CA (US); Kenneth Karl Hallenbeck, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 96 days.

(21) Appl. No.: 17/502,022

(22) Filed: Oct. 14, 2021

(65) Prior Publication Data

US 2022/0119860 A1    Apr. 21, 2022

Related U.S. Application Data

(60) Provisional application No. 63/092,104, filed on Oct. 15, 2020.

(51) Int. Cl.
  *C12Q 1/68*    (2018.01)
  *C12Q 1/686*   (2018.01)
  *B01L 7/00*    (2006.01)

(52) U.S. Cl.
  CPC .............. *C12Q 1/686* (2013.01); *B01L 7/52* (2013.01); *B01L 2300/1805* (2013.01)

(58) Field of Classification Search
  CPC .................................................. C12Q 1/686
  See application file for complete search history.

(56) References Cited

U.S. PATENT DOCUMENTS

| | | | |
|---|---|---|---|
| 8,934,098 B2 | 1/2015 | Cox et al. | |
| 2011/0012411 A1 | 5/2011 | Hoshizaki et al. | |
| 2020/0035329 A1 | 1/2020 | Janaway et al. | |

FOREIGN PATENT DOCUMENTS

| | | | |
|---|---|---|---|
| CA | 2855953 A1 | 5/2013 | |
| WO | 98/26098 A1 | 6/1998 | |
| WO | 2004/099441 A2 | 11/2004 | |
| WO | 2006/084132 A2 | 8/2006 | |

OTHER PUBLICATIONS

International Search Report and Written Opinion dated Jan. 28, 2022 in International Application No. PCT/US2021/055111, 12 pages.
Orlando David et al., "Quantitative ChIP-Seq Normalization Reveals Global Modulation of the Epigenome," Cell Reports, vol. 9, No. 3, Nov. 1, 2014, pp. 1163-1170, XP055881602, US ISSN 2211-1247, DOI: 10.1016/j.celrep.2014.10.018.

*Primary Examiner* — Teresa E Strzelecka
*Assistant Examiner* — Olayinka A Oyeyemi
(74) *Attorney, Agent, or Firm* — Baker Botts L.L.P.

(57) ABSTRACT

A method and system for normalizing a polymerase chain reaction (PCR) amplification process for a plurality of samples containing DNA. Cycle data for performing the PCR amplification process is identified for the plurality of samples. The cycle data includes a corresponding cycle count for each sample of the plurality of samples. The plurality of samples is sorted into a plurality of bins based on the cycle data such that cycle count variation between bins of the plurality of bins is reduced. A bin cycle count is assigned to each bin of the plurality of bins. The bin cycle count is unique to each bin of the plurality of bins. Identification information is generated for the bins. An output for performing a PCR amplification of the plurality of samples is generated using the bins and the bin cycle count for each bin of the plurality of bins.

10 Claims, 23 Drawing Sheets

| Bin 1 | Bin 2 | Bin 3 | Bin 4 | Bin 5 | Bin 6 | Bin 7 | Bin 8 |
|---|---|---|---|---|---|---|---|
| (0 <= Ct < 7) Cycles:9 | (7 <= Ct < 9) Cycles:11 | (9 <= Ct < 11) Cycles:13 | (11 <= Ct < 13) Cycles:15 | (13 <= Ct < 15) Cycles:17 | (15 <= Ct < 17) Cycles:19 | (17 <= Ct < 19) Cycles:21 | (19 <= Ct < 22) Cycles:23 |
| | | G6, 10.999 | C6, 11.716 | A6, 14.899 | A10, 15.255 | A2, 18.695 | I4, 19.513 |
| | | G24, 9.703 | C20, 11.369 | A24, 13.164 | A16, 16.168 | A4, 17.183 | I6, 19.521 |
| | | M24, 10.031 | C24, 11.809 | C2, 13.525 | A18, 16.527 | A8, 17.126 | I12, 19.347 |
| | | | G2, 12.238 | C4, 13.456 | A20, 15.736 | A12, 17.799 | I14, 20.374 |
| | | | G20, 12.609 | C8, 14.072 | A22, 15.917 | A14, 17.779 | I16, 19.07 |
| | | | K24, 12.403 | C10, 13.789 | C14, 16.027 | E4, 18.084 | I22, 21.254 |
| | | | O2, 12.777 | C12, 14.906 | C18, 15.699 | E22, 17.721 | |
| | | | O20, 12.698 | C16, 13.989 | E6, 16.478 | I2, 17.825 | |
| | | | O24, 11.863 | C22, 13.343 | E8, 15.326 | I8, 18.591 | |
| | | | | E2, 14.894 | E10, 15.212 | I10, 18.603 | |
| | | | | E20, 14.795 | E12, 16.205 | I18, 16.273 | |
| | | | | E24, 14.881 | E14, 16.346 | I20, 17.435 | |
| | | | | G4, 13.25 | E16, 15.916 | K4, 17.742 | |
| | | | | G8, 13.296 | E18, 15.867 | K12, 18.556 | |
| | | | | G10, 13.903 | G14, 15.078 | K14, 18.397 | |
| | | | | G12, 14.388 | I24, 16.18 | K20, 17.98 | |
| | | | | G16, 13.366 | K2, 15.252 | M12, 17.442 | |
| | | | | G18, 14.691 | K6, 16.405 | M14, 18.259 | |
| | | | | G22, 13.159 | K8, 15.691 | M18, 17.398 | |
| | | | | M10, 14.454 | K10, 16.76 | | |
| | | | | M20, 14.932 | K16, 16.044 | | |
| | | | | M22, 14.982 | K18, 16.712 | | |
| | | | | ... | ... | | |

FIG. 9A

| Bin 1<br>(0 <= Ct < 6) Cycles:8 | Bin 2<br>(6 <= Ct < 7) Cycles:9 | Bin 3<br>(7 <= Ct < 8) Cycles:10 | Bin 4<br>(8 <= Ct < 9) Cycles:11 | Bin 5<br>(9 <= Ct < 10) Cycles:12 | Bin 6<br>(10 <= Ct < 11) Cycles:13 | Bin 7<br>(11 <= Ct < 12) Cycles:14 | Bin 8<br>(12 <= Ct < 15) Cycles:16 |
|---|---|---|---|---|---|---|---|
| | A6, 6.274 | C16, 7.087 | A22, 8.608 | A4, 9.196 | A2, 10.298 | A8, 11.269 | A14, 12.693 |
| | C6, 6.462 | C18, 7.489 | A24, 8.523 | C2, 9.976 | A10, 10.084 | A12, 11.55 | E4, 12.406 |
| | M6, 6.822 | G2, 7.682 | C10, 8.639 | C8, 9.117 | A16, 10.625 | A18, 11.155 | E22, 12.33 |
| | | G6, 7.687 | C12, 8.406 | C20, 9.451 | A20, 10.501 | C4, 11.269 | G4, 12.005 |
| | | G24, 7.538 | C14, 8.178 | C22, 9.249 | E6, 10.22 | E12, 11.491 | I4, 12.975 |
| | | K8, 7.629 | C24, 8.033 | G8, 9.66 | E8, 10.898 | E16, 11.298 | I8, 12.373 |
| | | K16, 7.635 | E2, 8.809 | G14, 9.237 | E10, 10.766 | I20, 11.406 | I10, 14.973 |
| | | O8, 7.922 | G10, 8.36 | G20, 9.809 | E14, 10.939 | | I12, 12.151 |
| | | | G12, 8.531 | I6, 9.763 | E18, 10.884 | | I14, 13.791 |
| | | | G16, 8.411 | K6, 9.334 | E20, 10.639 | | I16, 12.369 |
| | | | G18, 8.705 | K14, 9.305 | E24, 10.013 | | I18, 13.033 |
| | | | G22, 8.961 | O6, 9.796 | I2, 10.782 | | I22, 13.615 |
| | | | K2, 8.848 | O10, 9.003 | I24, 10.757 | | K4, 12.281 |
| | | | K10, 8.49 | O14, 9.57 | K22, 10.592 | | M4, 12.722 |
| | | | K12, 8.181 | O18, 9.326 | K24, 10.726 | | M8, 12.602 |
| | | | K18, 8.607 | O20, 9.234 | M22, 10.417 | | M10, 13.125 |
| | | | K20, 6.759 | O22, 9.967 | | | M12, 13.482 |
| | | | M2, 8.421 | | | | M14, 14.052 |
| | | | M24, 8.828 | | | | M16, 12.164 |
| | | | O2, 6.975 | | | | M18, 12.64 |
| | | | O12, 8.351 | | | | M20, 12.246 |
| | | | O16, 8.894 | | | | O4, 12.204 |
| | | | O24, 8.447 | | | | |

FIG. 9B

| Bin 1 | Bin 2 | Bin 3 | Bin 4 | Bin 5 | Bin 6 | Bin 7 | Bin 8 |
|---|---|---|---|---|---|---|---|
| (0 <= Ct < 12.777) Cycles:14 | (12.777 <= Ct < 13.903) Cycles:15 | (13.903 <= Ct < 14.894) Cycles:16 | (14.894 <= Ct < 15.44) Cycles:17 | (15.44 <= Ct < 16.18) Cycles:18 | (16.18 <= Ct < 17.126) Cycles:19 | (17.126 <= Ct < 18.259) Cycles:20 | (18.259 <= Ct < 21.254) Cycles:21 |
| C6, 11.716 | A6, 13.164 | C8, 14.072 | A6, 14.899 | A16, 16.168 | A18, 16.527 | A4, 17.183 | A2, 18.695 |
| C20, 11.369 | C2, 13.525 | C16, 13.989 | A10, 15.255 | A20, 15.736 | E6, 16.478 | A8, 17.126 | I4, 19.513 |
| C24, 11.809 | C4, 13.456 | E20, 14.795 | C12, 14.906 | A22, 15.917 | E12, 16.205 | A12, 17.799 | I6, 19.521 |
| G2, 12.238 | C10, 13.788 | E24, 14.861 | E2, 14.894 | C14, 16.027 | E14, 16.346 | A14, 17.779 | I8, 18.591 |
| G6, 10.999 | C22, 13.343 | G10, 13.903 | E8, 15.326 | C18, 15.699 | I24, 16.18 | E4, 18.084 | I10, 18.603 |
| G20, 12.609 | G4, 13.25 | G12, 14.386 | E10, 15.212 | E16, 15.916 | K6, 16.405 | E22, 17.721 | I12, 19.347 |
| G24, 9.703 | G8, 13.296 | G18, 14.691 | G14, 15.078 | E18, 15.867 | K10, 16.76 | I2, 17.825 | I14, 20.374 |
| K24, 12.403 | G16, 13.366 | M10, 14.454 | K2, 15.252 | K6, 15.691 | K18, 16.712 | I20, 17.435 | I16, 19.07 |
| M24, 10.031 | G22, 13.159 | O8, 13.944 | M2, 15.359 | K16, 16.044 | K22, 16.537 | K4, 17.742 | I18, 18.273 |
| O20, 12.698 | O2, 12.777 | O10, 13.91 | M20, 14.932 | M4, 15.44 | M8, 16.217 | K20, 17.98 | I22, 21.254 |
| O24, 11.863 | O6, 13.682 | O12, 14.794 | M22, 14.982 | M6, 16.172 | M16, 16.919 | M12, 17.442 | K12, 18.556 |
|  | O22, 13.294 | O16, 14.518 | O18, 15.033 | O14, 16.034 | O4, 16.341 | M18, 17.398 | K14, 18.397 |
|  |  |  |  |  |  |  | M14, 18.259 |

FIG. 10

| Bin 1 (0 <= Ct < 11.5) Cycles:13 | Bin 2 (11.5 <= Ct < 13.5) Cycles:15 | Bin 3 (13.5 <= Ct < 15.5) Cycles:17 | Bin 4 (15.5 <= Ct < 17.5) Cycles:19 | Bin 5 (17.5 <= Ct < 18.5) Cycles:20 | Bin 6 (18.5 <= Ct < 19.5) Cycles:21 | Bin 7 (19.5 <= Ct < 20.5) Cycles:22 | Bin 8 (20.5 <= Ct < 21.5) Cycles:23 |
|---|---|---|---|---|---|---|---|
| C20, 11.369 | A24, 13.164 | A6, 14.899 | A4, 17.163 | A12, 17.799 | A2, 18.695 | I4, 19.513 | I22, 21.254 |
| G6, 10.999 | C4, 13.456 | A10, 15.255 | A8, 17.126 | A14, 17.779 | I8, 18.591 | I6, 19.521 | |
| G24, 9.703 | C6, 11.716 | C2, 13.525 | A16, 16.168 | E4, 18.084 | H10, 18.603 | I14, 20.374 | |
| M24, 10.031 | C22, 13.343 | C8, 14.072 | A18, 16.527 | E22, 17.721 | H2, 19.347 | | |
| | C24, 11.809 | C10, 13.788 | A20, 15.736 | I2, 17.825 | I16, 19.07 | | |
| | G2, 12.238 | C12, 14.906 | A22, 15.917 | I18, 18.273 | K12, 18.556 | | |
| | G4, 13.25 | C16, 13.989 | C14, 16.027 | K4, 17.742 | | | |
| | G8, 13.296 | E2, 14.894 | C18, 15.699 | K14, 18.397 | | | |
| | G16, 13.366 | E8, 15.326 | E6, 16.478 | K20, 17.98 | | | |
| | G20, 12.609 | E10, 15.212 | E12, 16.205 | M14, 18.259 | | | |
| | G22, 13.159 | E20, 14.795 | E14, 16.346 | | | | |
| | K24, 12.403 | E24, 14.881 | E16, 15.916 | | | | |
| | O2, 12.777 | G10, 13.903 | E18, 15.867 | | | | |
| | O20, 12698 | G12, 14.388 | I20, 17.435 | | | | |
| | O22, 13.294 | G14, 15.078 | I24, 16.18 | | | | |
| | O24, 11.863 | G18, 14.691 | K6, 16.405 | | | | |
| | | K2, 15.252 | K8, 15.691 | | | | |
| | | M2, 15.359 | K10, 16.76 | | | | |
| | | M4, 15.44 | K16, 16.044 | | | | |
| | | M10, 14.454 | K18, 16.712 | | | | |
| | | M20, 14.932 | K22, 16.537 | | | | |
| | | M22, 14.982 | M6, 16.172 | | | | |
| | | ... | ... | | | | |

FIG. 11A

| Bin 1 | Bin 2 | Bin 3 | Bin 4 | Bin 5 | Bin 6 | Bin 7 | Bin 8 |
|---|---|---|---|---|---|---|---|
| (0 <= Ct < 7.5) Cycles:9 | (7.5 <= Ct < 9.5) Cycles:11 | (9.5 <= Ct < 10.5) Cycles:12 | (10.5 <= Ct < 11.5) Cycles:13 | (11.5 <= Ct < 12.5) Cycles:14 | (12.5 <= Ct < 13.5) Cycles:15 | (13.5 <= Ct < 14.5) Cycles:16 | (14.5 <= Ct < 15.5) Cycles:17 |
| A6, 6.274 | A4, 9.196 | A2, 10.298 | A8, 11.269 | A12, 11.55 | A14, 12.693 | I14, 13.791 | I10, 14.973 |
| C6, 6.462 | A22, 8.608 | A10, 10.084 | A16, 10.625 | E4, 12.406 | I4, 12.975 | I22, 13.615 | |
| C16, 7.087 | A24, 8.523 | C2, 9.976 | A18, 11.155 | E22, 12.33 | I18, 13.033 | M14, 14.052 | |
| C18, 7.489 | C8, 9.117 | E6, 10.22 | A20, 10.501 | G4, 12.005 | M4, 12.722 | | |
| M6, 6.822 | C10, 8.639 | E24, 10.013 | C4, 11.269 | I6, 12.373 | M8, 12.602 | | |
| | C12, 8.406 | G8, 9.66 | E8, 10.898 | I12, 12.151 | M10, 13.125 | | |
| | C14, 8.178 | G20, 9.809 | E10, 10.766 | I16, 12.369 | M12, 13.482 | | |
| | C20, 9.451 | I6, 9.763 | E12, 11.491 | K4, 12.281 | M18, 12.64 | | |
| | C22, 9.249 | M22, 10.417 | E14, 10.939 | M16, 12.164 | | | |
| | C24, 8.033 | O6, 9.796 | E16, 11.298 | M20, 12.246 | | | |
| | E2, 8.809 | O14, 9.57 | E18, 10.884 | O4, 12.204 | | | |
| | G2, 7.682 | O22, 9.967 | E20, 10.639 | | | | |
| | G6, 7.687 | | I2, 10.782 | | | | |
| | G10, 8.36 | | I20, 11.406 | | | | |
| | G12, 8.531 | | I24, 10.757 | | | | |
| | G14, 9.237 | | K22, 10.592 | | | | |
| | G16, 8.411 | | K24, 10.726 | | | | |
| | G18, 8.705 | | | | | | |
| | G22, 8.961 | | | | | | |
| | G24, 7.536 | | | | | | |
| | ... | | | | | | |

MULTIPLEXED TARGET-BINDING CANDIDATE SCREENING ANALYSIS

CROSS-REFERENCE TO RELATED APPLICATION

This application claims priority to U.S. Provisional Patent Application No. 63/092,104, entitled "Multiplexed Target-Binding Candidate Screening Analysis," filed Oct. 15, 2020, which is incorporated herein by reference in its entirety.

FIELD

Provided herein are methods and systems for improved multiplexed screening analysis. More specifically, methods and systems are provided for multiplexed screening of nucleotide-tagged peptide libraries for target-binding activity.

BACKGROUND

Current multiplexed target-binding candidate screening analysis systems have difficulty with the simultaneous selection of many nucleotide-containing peptide libraries for binding to a desired target due to problems such as sample-to-sample variations and data complexity. There is, therefore, a need for improved multiplexed target-binding candidate screening analysis systems and methods to help simultaneous selection of candidate binders against a desired binding target, e.g., a protein.

SUMMARY

The embodiments described herein provide various methods, systems, and computer program products for improved multiplexed screening analysis.

In some embodiments, a method is provided for normalizing a plurality of libraries of DNA-containing compositions. The method includes receiving quantification information for each of a plurality of libraries of DNA-containing compositions for a first round of selection, wherein each of the libraries comprises DNA conjugates, and wherein the first round of selection causes selection of the DNA conjugates based on binding affinity to a target protein. The method further includes determining a polymerase chain reaction ("PCR") cycle count specific for each of the libraries using the quantification information, wherein DNA-containing compositions of each of the libraries can produce or are determined to produce an associated pre-set amount of DNA after performing PCR with a corresponding PCR cycle count. The method further includes sorting the libraries of DNA-containing compositions into bins using corresponding PCR cycle counts so determined, wherein each bin comprises a different subset of the libraries of the DNA-containing compositions determined to share a common PCR cycle count for DNA amplification, and each subset of the libraries of the DNA-containing compositions in the same bin shares a common PCR cycle count different from that of other bins of libraries. The method further includes instructing a thermocycler to perform PCR, in a same run, on one of the bins with a corresponding common PCR cycle count simultaneously for a subset of the libraries of DNA-containing compositions of the same bin. The method further includes instructing the thermocycler to perform PCR on each of additional bins with a corresponding common PCR cycle count so that the plurality of libraries of DNA-containing compositions are normalized.

In some embodiments, there is provided a computer-program product tangibly embodied in a non-transitory machine-readable storage medium, including instructions configured to cause one or more data processors to perform a method for normalizing a plurality of libraries of DNA-containing compositions. The method includes receiving quantification information for each of a plurality of libraries of DNA-containing compositions for a first round of selection, wherein each of the libraries comprises DNA conjugates, and wherein the first round of selection causes selection of the DNA conjugates based on binding affinity to a target protein. The method further includes determining a polymerase chain reaction ("PCR") cycle count specific for each of the libraries using the quantification information, wherein DNA-containing compositions of each of the libraries are determined to produce an associated pre-set amount of DNA after performing PCR with a corresponding PCR cycle count. The method further includes sorting the libraries of DNA-containing compositions into bins using corresponding PCR cycle counts so determined, wherein each bin comprises a different subset of the libraries of the DNA-containing compositions determined to share a common PCR cycle count for DNA amplification, and each subset of the libraries of the DNA-containing compositions in the same bin shares a common PCR cycle count different from that of other bins of libraries. The method further includes instructing a thermocycler to perform PCR, in a same run, on one of the bins with a corresponding common PCR cycle count simultaneously for a subset of the libraries of the DNA-containing compositions of the same bin. The method further includes instructing the thermocycler to perform PCR on each library of DNA-containing compositions of additional bins so that the plurality of libraries of DNA-containing compositions are normalized.

In some embodiments, a system is provided for normalizing a plurality of libraries of DNA-containing compositions. The system includes a data store configured to store a dataset containing quantification information of each of a plurality of libraries of DNA-containing compositions for each round of selection, wherein each of the libraries of DNA-containing compositions comprises DNA conjugates, and wherein each round of selection causes selection of the DNA conjugates based on binding affinity to a target protein; one or more data processors; and a computing device communicatively connected to the data store and configured to receive the data set, the computing device comprising a non-transitory computer readable storage medium containing instructions which, when executed on the one or more data processors, cause the one or more data processors to perform a method for normalizing a plurality of libraries of DNA-containing compositions. The method includes sorting the libraries of DNA-containing compositions into bins using the datasets, wherein each bin comprises a different subset of the libraries of the DNA-containing compositions determined to share a common PCR cycle count for DNA amplification using the quantification information, and each subset of the libraries of the DNA-containing compositions in the same bin shares a common PCR cycle count different from that of other bins of libraries. The system further includes a thermocycler configured to perform PCR, in a same run, on one of the bins with a corresponding common PCR cycle count simultaneously for DNA-containing compositions of the same bin and to perform PCR on each library of DNA-containing compositions of additional bins so that the plurality of libraries of DNA-containing compositions are normalized.

In some embodiments, a method is provided for monitoring quantification information of a plurality of libraries of DNA-containing compositions to detect target binding. The method includes receiving quantification information of each of a plurality of libraries of DNA-containing compositions for a first round of selection, wherein each of the libraries comprises DNA conjugates, and wherein the first round of selection causes selection of the DNA conjugates based on binding affinity to a target protein. The method further includes generating a first window within a graphical user interface, the first window displaying the quantification information of each of the libraries for the first round of selection. The method further includes repeating the receiving step and generating step to generate additional windows over a plurality of subsequent rounds of selection, wherein each of the additional windows displays quantification information of each of the libraries for each of the subsequent rounds of selection so that quantification information of the DNA-containing compositions of each of the libraries for each round is monitored.

In some embodiments, there is provided a computer-program product tangibly embodied in a non-transitory machine-readable storage medium for monitoring quantification information of a plurality of libraries of DNA-containing compositions to detect target binding, The computer-program product includes instructions configured to cause one or more data processors to perform a method for monitoring quantification information of libraries to detect target binding in a graphical user interface. The method includes receiving, at a first step, quantification information of each of a plurality of libraries of DNA-containing compositions for a first round of selection, wherein each of the libraries of DNA-containing compositions comprises DNA conjugates, and wherein the first round of selection causes selection of the DNA conjugates based on binding affinity to a target protein. The method includes displaying, at a second step, a first window within a graphical user interface, the first window containing the quantification information of each of the libraries of DNA-containing compositions after the first round of selection; and repeating the first and second steps to generate additional windows over a plurality of subsequent rounds of selection, wherein each of the additional windows displays quantification information of each of the libraries for each of the subsequent rounds of selection so that quantification information of the DNA-containing compositions of each of the libraries for each round is monitored.

In some embodiments, a system is provided for monitoring quantification information of a plurality of libraries of DNA-containing compositions to detect target binding. The system includes a data store configured to store a dataset containing quantification information of each of a plurality of libraries of DNA-containing compositions for each round of selection, wherein each of the libraries of DNA-containing compositions comprises DNA conjugates, and wherein each round of selection causes selection of the DNA conjugates based on binding affinity to a target protein. The system further includes one or more data processors and a computing device communicatively connected to the data store and configured to receive the data set, the computing device comprising a non-transitory computer readable storage medium containing instructions which, when executed on the one or more data processors, cause the one or more data processors to perform a method for displaying the quantification information of each of the libraries of DNA-containing compositions. The method includes generating a graphical user interface comprising windows that are selected to display the quantification information of each of the libraries of DNA-containing compositions for any round of selection that has been selected to be displayed.

In one or more embodiments, a method is provided for normalizing a polymerase chain reaction (PCR) amplification process for a plurality of samples containing DNA. Cycle data for performing the PCR amplification process is identified for the plurality of samples. The cycle data includes a corresponding cycle count for each sample of the plurality of samples. The plurality of samples is sorted into a plurality of bins based on the cycle data such that cycle count variation between bins of the plurality of bins is reduced. A bin cycle count is assigned to each bin of the plurality of bins. The bin cycle count is unique to each bin of the plurality of bins. Identification information is generated for the bins. An output for performing a PCR amplification of the plurality of samples is generated using the bins and the bin cycle count for each bin of the plurality of bins.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is embodied in a non-transitory machine-readable storage medium and that includes instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the claimed embodiments. Thus, it should be understood that although the present claimed embodiments have been specifically disclosed as embodiments and optional features, modification and variation of the concepts herein disclosed may be resorted to by those skilled in the art, and that such modifications and variations are considered to be within the scope of the appended claims.

BRIEF DESCRIPTION OF THE DRAWINGS

The present disclosure is described in conjunction with the appended figures:

FIG. 9A is a table illustrating a first round of dynamic binning using an upper bias in accordance with one or more embodiments.

FIG. 9B is a table illustrating a fourth round of dynamic binning using an upper bias in accordance with one or more embodiments.

FIG. 10 is a table illustrating a first round of dynamic binning using even distribution in accordance with one or more embodiments.

FIG. 11A is a table illustrating a first round of dynamic binning with a bias towards samples having cycle counts within a selected range of cycle counts in accordance with one or more embodiments.

FIG. 11B is a table illustrating a fourth round of dynamic binning bias towards samples having cycle counts within a selected range of cycle counts in accordance with one or more embodiments.

Figure 1:
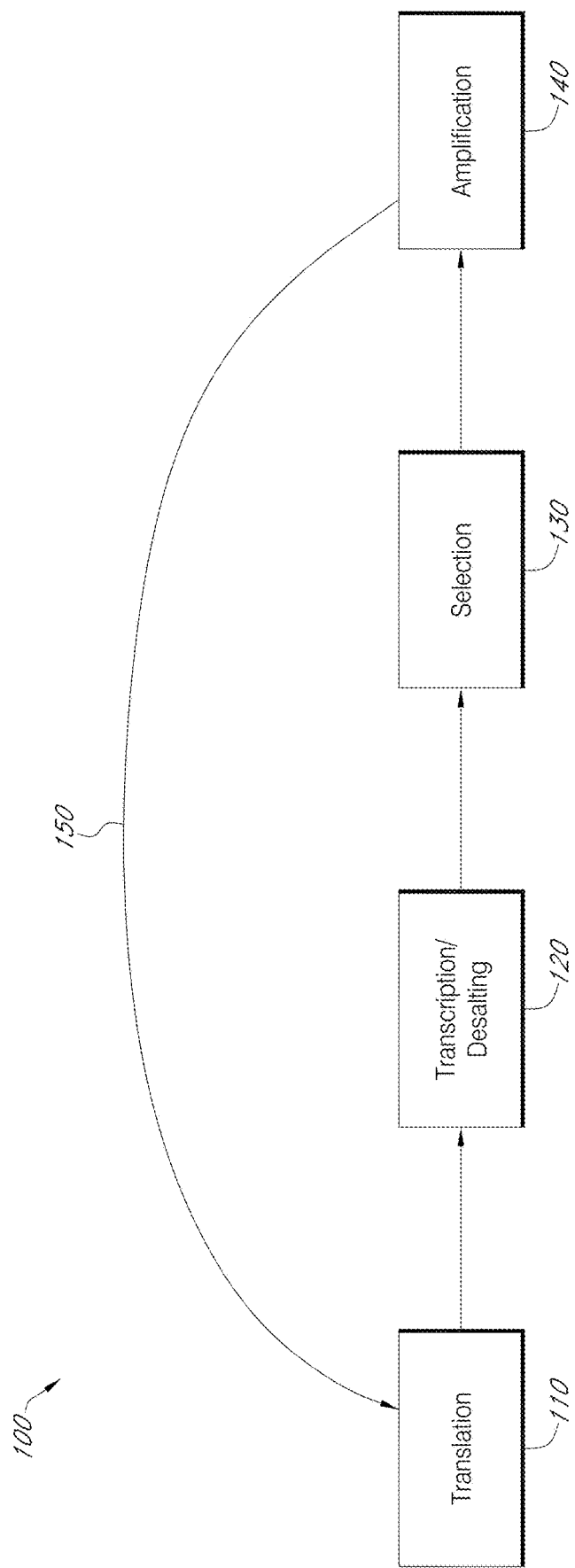
FIG. 1 illustrates non-limiting exemplary embodiments of a general schematic workflow for screening a plurality of libraries of DNA-containing compositions for binding to a desired binding target, in accordance with various embodiments.

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

I. Overview

This disclosure describes various exemplary embodiments of methods, and systems for screening nucleotide-tagged peptide libraries for binding activity to one or more desired target(s). The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion.

II. Exemplary Context and Descriptions of Terms

It is to be understood that the terminology used herein is for the purpose of describing particular embodiments only, and is not intended to be limiting.

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art. Generally, nomenclatures utilized in connection with, and techniques of, chemistry, biochemistry, molecular biology, pharmacology and toxicology are described herein are those well-known and commonly used in the art.

As used herein, the singular forms "a," "an," and "the" are intended to include the plural forms as well, unless the context clearly indicates otherwise. It is also to be understood that the term "and/or" as used herein refers to and encompasses any and all possible combinations of one or more of the associated listed items. It is further to be understood that the terms "includes," "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

Throughout this disclosure, various aspects are presented in a range format. It should be understood that the description in range format is merely for convenience and brevity and should not be construed as an inflexible limitation on the disclosure. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed in the disclosure. The upper and lower limits of these smaller ranges may independently be included in the smaller ranges, and are also encompassed in the disclosure, subject to any specifically excluded limit in the stated range. Where the stated range includes one or both of the limits, ranges excluding either or both of those included limits are also included in the disclosure. This applies regardless of the breadth of the range.

The term "about" as used herein refers to include the usual error range for the respective value readily known. Reference to "about" a value or parameter herein includes (and describes) embodiments that are directed to that value or parameter per se. For example, description referring to "about X" includes description of "X". In some embodiments, "about" may refer to ±15%, ±10%, ±5%, or ±1% as understood by a person of skill in the art.

In addition, as the terms "in communication with" or "communicatively coupled with" or similar words are used herein, one element may be capable of communicating directly, indirectly, or both with another element via one or more wired communications links, one or more wireless communications links, one or more optical communications links, or a combination thereof. In addition, where reference is made to a list of elements (e.g., elements a, b, c), such reference is intended to include any one of the listed elements by itself, any combination of less than all of the listed elements, and/or a combination of all of the listed elements.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

As used herein, the term "ones" means more than one.

As used herein, the term "plurality" or "group" can be 2, 3, 4, 5, 6, 7, 8, 9, 10, or more.

As used herein, the term "set" means one or more.

As used herein, the phrase "at least one of," when used with a list of items, may mean different combinations of one or more of the listed items may be used and only one of the items in the list may be needed. The item may be a particular object, thing, step, operation, process, or category. In other words, "at least one of" means any combination of items or number of items may be used from the list, but not all of the items in the list may be required. For example, without limitation, "at least one of item A, item B, or item C" or "at least one of item A, item B, and item C" may mean item A; item A and item B; item B; item A, item B, and item C; item B and item C; or item A and C. In some cases, "at least one of item A, item B, or item C" or "at least one of item A, item B, and item C" may mean, but is not limited to, two of item A, one of item B, and ten of item C; four of item B and seven of item C; or some other suitable combination.

An "individual", "subject," or "patient" may be a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain aspects, the individual or subject is a human.

As used herein, "nucleic acid sequencing data," "nucleic acid sequencing information," "nucleic acid sequence," "genomic sequence," "genetic sequence," or "fragment sequence," or "nucleic acid sequencing read" may denote any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

A "nucleotide," "polynucleotide," "nucleic acid," or "oligonucleotide" may refer to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

As used herein, the term "cell" may be used interchangeably with the term "biological cell." Non-limiting examples of biological cells include eukaryotic cells, plant cells, animal cells, such as mammalian cells, reptilian cells, avian cells, fish cells or the like, prokaryotic cells, bacterial cells, fungal cells, protozoan cells, or the like, cells dissociated from a tissue, such as muscle, cartilage, fat, skin, liver, lung, neural tissue, and the like, immunological cells, such as T cells, B cells, natural killer cells, macrophages, and the like, embryos (e.g., zygotes), oocytes, ova, sperm cells, hybridomas, cultured cells, cells from a cell line, cancer cells, infected cells, transfected and/or transformed cells, reporter cells and the like. A mammalian cell can be, for example, from a human, mouse, rat, horse, goat, sheep, cow, primate or the like.

As used herein, a "genome" is the genetic material of a cell or organism, including animals, such as mammals, e.g., humans. In humans, the genome includes the total DNA, such as, for example, genes, noncoding DNA and mitochondrial DNA. The human genome typically contains 23 pairs of linear chromosomes: 22 pairs of autosomal chromosomes plus the sex-determining X and Y chromosomes. The 23 pairs of chromosomes include one copy from each parent. The DNA that makes up the chromosomes is referred to as chromosomal DNA and is present in the nucleus of human cells (nuclear DNA). Mitochondrial DNA is located in mitochondria as a circular chromosome, is inherited from only the female parent, and is often referred to as the mitochondrial genome as compared to the nuclear genome of DNA located in the nucleus.

The phrase "sequencing" may refer to any technique known in the art that allows the identification of consecutive nucleotides of at least part of a nucleic acid. Non-limiting exemplary sequencing techniques include RNA-seq (also known as whole transcriptome sequencing), Illumina™ sequencing, direct sequencing, random shotgun sequencing, Sanger dideoxy termination sequencing, whole-genome sequencing, massively parallel signature sequencing (MPSS), sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, mass spectrometry, and any combination thereof.

The phrase "RNA-seq (RNA-sequencing)" may refer to any step or technique that can examine the presence, quantity or sequences of RNA in a biological sample using sequencing such as next generation sequencing (NGS). RNA-seq can analyze the transcriptome of gene expression patterns encoded within the RNA.

The phrase "next generation sequencing" (NGS) may refer to sequencing technologies having increased throughput as compared to traditional Sanger and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization. More specifically, the MISEQ, HISEQ and NEXTSEQ Systems of Illumina and the Personal Genome Machine (PGM) and SOLiD Sequencing System of Life Technologies Corp, provide massively parallel sequencing of whole or targeted genomes. The SOLiD System and associated workflows, protocols, chemistries, etc. are described in more detail in PCT Publication No. WO 2006/084132, entitled "Reagents, Methods, and Libraries for Bead-Based Sequencing," international filing date Feb. 1, 2006, U.S. patent application Ser. No. 12/873,190, entitled "Low-Volume Sequencing System and Method of Use," filed on Aug. 31, 2010, and U.S. patent application Ser. No. 12/873,132, entitled "Fast-Indexing Filter Wheel and Method of Use," filed on Aug. 31, 2010, the entirety of each of these applications being incorporated herein by reference thereto.

The term "in vitro display" may refer to a system that displays a phenotype with a genotype through conjugating the phenotype and the genotype, which encodes the sequence of the phenotype, by a noncovalent bond or a covalent bond. Non-limiting examples of in vitro display include mRNA display, PD display, STABLE (non-covalent DNA display), microbead/droplet display, covalent DNA display, phage display and ribosome display. The in vitro display can enable enrichment and amplification (selection) of active species using replication systems reconstituted in test tubes. A great advantage of an in vitro display system is that it allows one to search through a library encompassing a wide variety of standard, nonstandard peptides or a combination thereof, obviating the use of prokaryote and eukaryote organisms as mediums, enabling the selection of highly active physiological substance (e.g., peptides). An in vitro display can enable one to search libraries with a diversity of 10 to the 13th power. Although mRNA display is explained as an example in some embodiments, an in vitro display can be used instead.

The term "RNA display" or "mRNA display" may refer to an in vitro technique wherein, expressed proteins or peptides are linked covalently or by non-covalent interaction to their encoding nucleic acid to form "mRNA/DNA-peptide conjugate" molecules. The protein or peptide component of an mRNA/DNA-peptide conjugate is selected as candidates for binding to a desired binding target and the identity of the candidate protein or peptide determined by sequencing of the attached encoding mRNA component.

The term "flexizyme" may refer to an artificial RNA catalyst developed as an aminoacyl-tRNA synthetase. Flexizymes are also known by designations such as dinitrobenzyl flexizyme (dFx), enhanced flexizyme (eFx), amino flexizyme (aFx), etc. Flexizymes can catalyze aminoacylation of adenosine at the 3' end using a weakly activated amino acid as a substrate by recognizing a carbonyl group with which the amino acid reacts, an aromatic ring in a side chain or leaving group of the amino acid, or an ACC-3' sequence at the 3' end of a linker.

The term "macrocyclic peptide" or "macrocycle" may refer to a peptide comprising a macrocyclic structure of four, five, six, seven, eight, nine, ten, eleven, twelve, or more amino acids or any intermediate ranges or values derived therefrom. As used herein, "macrocyclic structure" refers to a closed ring structure formed in a linear peptide. The ring structure can be formed by binding two amino acids separated by at least two amino acid residues directly or via a linker. The macrocyclic peptide or macrocycle can comprise one, two, three, four, five, or more rings.

The term "Ct (cycle threshold)" may refer to the number of cycles required for the fluorescent signal to cross the threshold (e.g., exceeds a background level). Ct levels are inversely proportional to the amount of candidate nucleic acid in the sample (i.e., the lower the Ct level the greater the amount of candidate nucleic acid in the sample).

The term "selecting" used in a target-binding selection may refer to substantially partitioning a molecule from other molecules in a population. As used herein, a "selecting" step may provide at least a 2-fold, preferably, a 30-fold, more preferably, a 100-fold, and, most preferably, a 1000-fold enrichment of a desired molecule relative to undesired molecules in a population following the selection step. As indicated herein, a selection step may be repeated any number of times and/or different types of selection steps may be combined in a given approach.

III. Target-Binding Candidate Discovery

Various method and system embodiments described herein enable improved multiplexed methods to detect peptide candidates in selection for binding to a desired target. For example, RNA display methods can be used here. RNA display generally involves expression of proteins or peptides, wherein the expressed proteins or peptides are linked covalently or by tight non-covalent interaction to their encoding mRNA to form RNA/protein fusion molecules. The protein or peptide component of an RNA/protein fusion can be selected for binding to a desired target and the identity of the protein or peptide determined by sequencing of the attached encoding mRNA component.

FIG. 1 illustrates non-limiting exemplary embodiments of a general schematic workflow for screening a plurality of libraries of DNA-containing compositions for binding to a desired target, in accordance with various embodiments.

The workflow 100 can comprise, at step 110, obtaining starting nucleic acid libraries (e.g., wells in a multi-well plate) and translating the starting nucleic acid libraries into peptide libraries that are encoded by their corresponding nucleic acids to produce libraries of nucleotide-containing conjugates. The starting nucleic acid libraries can comprise at least, at most, or about 10, 100, $10^3$, $10^4$, $10^5$, $10^6$, $10^7$, $10^8$, $10^9$, $10^{10}$, $10^{11}$, $10^{12}$, $10^{13}$, $10^{14}$, $10^{15}$, $10^{16}$, $10^{17}$, $10^{18}$, $10^{19}$, or $10^{20}$ (or any intermediate numbers of ranges derived therefrom) conjugates. The starting nucleic acid libraries can be chosen with a design preference. For example, the starting nucleic acid libraries can be chosen to have a low abundance of conjugates and can comprise about 10, 100, or $10^3$ (or any intermediate numbers of ranges derived therefrom) conjugates. The starting nucleic acid libraries can be chosen to have a medium abundance of conjugates and can comprise about $10^4$, $10^5$, $10^6$, $10^7$, $10^8$, or $10^9$ (or any intermediate numbers of ranges derived therefrom) conjugates. The starting nucleic acid libraries can be chosen to have a high abundance of conjugates and can comprise about $10^{10}$, $10^{11}$, $10^{12}$, $10^{13}$, or $10^{14}$ (or any intermediate numbers of ranges derived therefrom) conjugates.

The workflow 100 translates RNA to peptides by adding an in vitro translation mix, according to some embodiments. For example, the in vitro translation mix comprises a ribozyme that charges tRNA with standard amino acids, a ribozyme that charges tRNA with non-standard amino acids, or a combination thereof, such as an aminoacyl-tRNA synthetase (aaRS or ARS or also called tRNA-ligase) for adding standard amino acids, a flexizyme for adding non-standard amino acids, or a combination thereof. During the in vitro translation reaction, the mRNA molecules become covalently linked to their peptide products via a peptide acceptor (e.g., puromycin) fused at the 3' end. In additional and alternative embodiments, the nucleotide-containing conjugates may comprise linkers that link mRNA to the corresponding peptides.

The peptide can be linear, stapled, cyclic, or a combination thereof. In particular embodiments, the cyclic peptide is a macrocyclic peptide. The macrocyclic peptide can have one, two, three, or more rings. The macrocyclic peptide can comprise monocycle peptides, bicycle peptides or tetracycle peptides, or a combination thereof. The libraries of nucleotide-containing conjugates may comprise RNA conjugated to peptides as mRNA-displayed peptides.

The workflow 100 can comprise, at step 120, in vitro reverse transcription of nucleotide-containing conjugates and desalting the in vitro reverse transcription product. For example, the workflow 100 produces DNA-mRNA-peptide conjugates by adding a reverse transcription mix to mRNA-peptide conjugates. The workflow 100 transfers the resulting DNA-mRNA-peptide conjugates to desalting columns to remove salts and other small molecules, so desalted libraries are produced. The desalted libraries may be input for a round of selection to detect target-binding candidate peptides.

The workflow 100 can comprise, at step 130, selection of target-binding candidates from input libraries. The input libraries may comprise the nucleotide-containing conjugates after in vitro reverse transcription and desalting. Each selection may comprise positive selection for candidate binders binding to a desired target molecule, negative selection to remove libraries that bind to support without the desired target molecule, or a combination thereof.

For example, the target molecules are bound to a solid support, such as agarose beads. The target molecule is directly linked to a solid substrate. In another embodiment, the target molecule is first modified, for example, biotinylated, then the modified target molecule is bound via the modification to a solid substrate, such as a bead. Non-limiting examples of a solid-support include streptavidin (SA)-M280, neutravidin-M280, SA-M270, NA-M270, SA-MyOne, NA-MyOne, SA-agarose, and NA-agarose. In additional and alternative embodiments, the solid support further includes magnetic beads, for example Dynabeads®. Such magnetic beads allow separation of the solid support, and any bound nucleotide-containing conjugates, from an assay mixture using a magnet.

In negative selection, the input libraries can be mixed thoroughly with empty beads. Any bead-binding members from the input libraries can be removed. In some embodiments, the first round of selection skips negative selection.

In positive selection, the input libraries can be incubated with one or more target molecules bound to a solid support, e.g., beads that capture tags displayed on one or more target molecules. For example, a pull-down assay can be performed to wash off unbound nucleotide-containing conjugates and elute candidate binders from beads that are attached to a target protein, i.e., positive beads.

The target-bound nucleotide-containing conjugates can be eluted from the solid support prior to amplification of the nucleic acid component. Any available method of elution is contemplated. Alternatively or additionally, the target-bound nucleotide-containing conjugates can be eluted at a high temperature, e.g., boiling. Alternatively or additionally, the target-bound nucleotide-containing conjugates are eluted using alkaline conditions, for example, using a pH of about 8.0, 8.5, 9.0, 9.5, 10.0, or any intermediate ranges or values derived therefrom. In additional and alternative embodiments, the target-bound nucleotide-containing conjugates are eluted using acid conditions, for example, using a pH of about 3.0, 3.5, 4.0, 4.5, 5.0, 5.5, 6.0, or any intermediate ranges or values derived therefrom.

For example, the positive beads can be transferred to a PCR plate, sealed, and boiled. The positive beads can then be cooled and transferred to a magnetic plate. The supernatant from the magnetic plate can be removed and transferred to a new PCR plate for further analysis of the nucleotide-containing conjugates.

The workflow 100 can comprise, at step 140, amplification of selected target-binding candidates from the input libraries. For example, selected target-binding candidates are DNA-RNA-peptide conjugates. The workflow 100 amplifies DNA in selected target-binding candidates by PCR and uses the amplified product as input for the next round of selection or analyzed by sequencing.

The workflow 100 quantifies and normalizes, at step 140, selected target-binding candidates for DNA amplification. The workflow 100 measures DNA concentration in selected target-binding candidates, for example by quantitative PCR (qPCR). The workflow 100 collects and analyzes qPCR data for normalization to ensure appropriate DNA concentration to be used in the next round of selection. For example, the workflow 100 collects Ct values for each selected target-binding candidate by qPCR and may be used to determine appropriate PCR cycles for using PCR to amplify each selected target-binding candidate.

In additional and alternative embodiments, RNA in selected target-binding candidates may be amplified to produce more RNA. Any available method of RNA replication is contemplated, for example, using an RNA replicase enzyme. In another embodiment, RNA in eluted target-binding candidates may be transcribed into cDNA before being amplified by PCR.

Step 140 may involve quantification and normalization of selected target-binding candidates for amplification, which may be further exemplified in additional and alternative normalization workflows and in FIGS. 2-8 in more detail. Visualization of quantification and normalization results may be described in more detail in visualization workflows and FIGS. 9-14.

The workflow 100 can comprise, at step 150, repeated selection of target-binding candidates from input libraries. The PCR-amplified pool can be subject to one or more rounds of selection to enrich for the highest affinity target-binding candidates, for example, two, three, four, five, six, seven, eight, nine, ten or more rounds. The process of selection and amplification is repeated until the libraries are dominated by candidates with the desired properties. The number of repetitions needed depends on the diversity of the starting libraries and the enrichment achieved in the selection step.

At step 150, amplified DNA nucleotides may be transcribed to mRNA and then translated to peptides to produce additional libraries of nucleotide-containing conjugates for another round selection of steps 110, 120, 130, and 140.

Additionally or alternatively, the nucleic acid sequences may be amplified under conditions that result in the introduction of mutations into amplified DNA, thereby introducing further diversity into the selected nucleic acid sequences. This mutated pool of DNA molecules may be subjected to further rounds of selection.

Additionally or alternatively, the PCR amplified pool of nucleic acids may be sequenced using any available sequencing methods to determine the nucleic sequences of every selected nucleotide-containing conjugates, for example, next generation sequencing (NGS). The sequence identity of selected nucleotide-containing conjugates can be further used for validation of target binding affinity of selected nucleotide sequences.

IV. Normalization of Nucleotide-Containing Libraries

Various method and system embodiments described herein enable improved reliable quantitative assessment of target binding selection using in vitro display. In particular, the embodiments described herein enable tracking the progress and success or failure of simulation selections from one round to another round. The methods and systems described herein are robust and reproducible and may be used to normalize nucleotide-containing libraries for target binding selection.

Normalization helps minimize the variation of input DNA to the subsequent round between individual DNA-containing compositions, e.g., well-to-well variations. The input DNA may be used to generate libraries of potential binders, and the DNA concentration of the libraries generated may be measured and recorded as part of the experiment in each round of selection. Normalization helps to compare the progress and success/failure of simultaneous selections in each round of selection.

One non-limiting advantage may be that normalization methods and systems used herein may allow to track progress of several rounds of selection with any possible combination of DNA concentrations as input while obviating the need of manual intervention.

IV.A. Normalization Workflow

Figure 2:
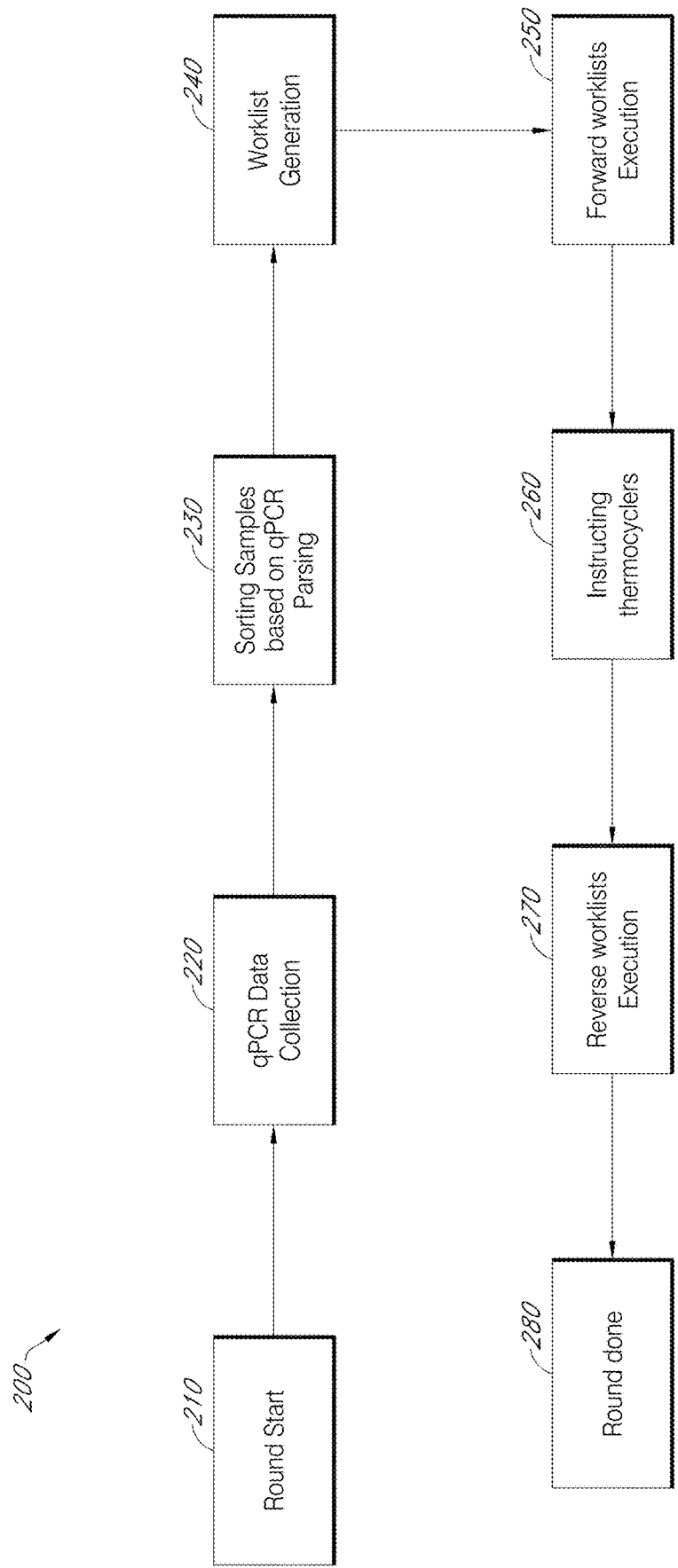
FIG. 2 illustrates non-limiting exemplary embodiments of a general schematic workflow for normalizing a plurality of libraries of DNA-containing compositions, in accordance with various embodiments.

A general schematic workflow 200 is provided in FIG. 2 to illustrate a non-limiting example process for normalizing a plurality of libraries of DNA-containing compositions in accordance with various embodiments. Such a normalization can handle any possible combinations of DNA concentrations of different libraries in between different experiments without intervention. For example, the different experiments can be different rounds of selection for target-binding candidates, e.g., an in vitro display selection. The workflow can include various combinations of features, whether it be more or less features than that illustrated in FIG. 2. As such, FIG. 2 simply illustrates one example of a possible workflow. The workflow 200 may be implemented using, for example, system 1200 described with respect to FIG. 12 or a similar system.

The workflow 200 can comprise, at step 210, starting a round of selection to detect binding to a desired target molecule. The round of selection may start with translation, reverse transcription, desalting, and selection to detect binding to a target molecule, and quantification of selected nucleotide-containing compositions, for example, by qPCR.

The workflow 200 can comprise, at step 220, qPCR data collection from a round of selection to detect target-binding candidates. The workflow 200 performs qPCR by transferring a small sample of each of the selected nucleotide-containing conjugates into a designated space of a container, for example, a 384-well plate. In various embodiments, qPCR is used to measure the concentration of candidate DNA in a given sample through repeated cycles of sequence-specific DNA amplification followed by DNA concentration measurements. Between subsequent cycles, the amount of each candidate DNA approximately doubles during the exponential phase of amplification. The cycle at which the observed DNA concentration first exceeds a fixed threshold is commonly called the threshold cycle (Ct). These Ct values represent a quantitative assessment of DNA concentration and are often treated as the raw data for subsequent analyses.

At step 220, qPCR data collection can comprise receiving qPCR data from a qPCR machine, performing data analysis, and exporting data to a computer. In various embodiments, the most recent qPCR data can be transferred and read into a database. The Ct values of each sample of one round of selection can be extracted from the qPCR data and visualized simultaneously as described more in detail in FIGS. 9-14.

The workflow 200 can comprise, at step 230, sorting a plurality of DNA-containing compositions. For example, the plurality of DNA-containing compositions can be sorted into bins based on their respective quantification information, e.g., the Ct values of each sample (i.e., DNA-containing composition) or PCR cycle count of each sample determined based on the Ct values. The sorting can be automatic.

For example, each bin is determined to share a common PCR cycle count for subsequent amplification to normalize the concentration of each DNA-containing composition. Each bin groups DNA-containing compositions with similar concentration, for example, with the same Ct value within a range or same PCR cycle count within a range. The same Ct value within a range may refer to a Ct value within 1, 2, 3, 4, or 5 integer values or any ranges or values derived therefrom. The same PCR cycle count within a range may refer to a PCR cycle count value within 1, 2, 3, 4, or 5 integer values or any ranges or values derived therefrom.

For example, all individual wells with Ct values within 3 Ct values (e.g., Ct of 9, 10, and 11) may be combined into one bin, and may be applied with the same number of PCR cycle counts (e.g., 10 PCR cycles) for the entire bin for subsequent amplification. Each bin may be assigned with an identification label such as a barcode and corresponding samples with an assigned common PCR cycle based on the quantification information such as Ct from a qPCR quantification assay. For example, each PCR cycle count for each well or the assigned common PCR cycle can be based on a pre-determined formula, for example, each PCR cycle count for each well or the assigned common PCR cycle can be Ct of the respective well rounded to the nearest integer or can be Ct of the respective well adding or subtracting a whole number from the rounded integer. If several wells have similar Ct, some wells may be assigned a common PCR cycle count, or each has a similar PCR cycle count based on similar Ct and is assigned a common PCR cycle count based on a range of these similar Ct values or similar PCR cycle counts. In some embodiments, PCR cycle count for each well can be equivalent or can be adjusted to be equivalent to a common PCR cycle count shared by several wells that have similar Ct values.

These assignments may be organized into worklists and transferred to a liquid handler. The liquid handler can execute worklists by selecting the samples and transferring the selected samples from a source plate into plates for PCR amplification with the assigned common PCR cycle. After PCR amplification, the liquid handler can transfer the samples so amplified back to original wells of the source plate.

As shown in Table 1, a PCR cycle count for future amplification may be determined using determined qPCR Ct values (Min and Max refer to the minimum and maximum qPCR Ct values in each bin). In Table 1, all the samples are sorted into bins according to previously-determined qPCR Ct values, with each bin having samples that are determined to share a common PCR cycle count for future amplification. For example, when a sample has a qPCR Ct of 13, it will be in the 3rd bin and will be assigned to have 15 cycles of PCR for subsequent amplification as shown in the following Table 1 ("PCR cycle count").

As shown in Table 1, any sample that has a qPCR Ct between 0 and 9 can be assigned to a bin in which all the samples in the bin are assigned 9 cycles of PCR for subsequent amplification. Any sample that has a qPCR Ct between 10 and 12 can be assigned to a bin in which all the samples in the bin are assigned 12 cycles of PCR for subsequent amplification. Any sample that has a qPCR Ct between 13 and 15 can be assigned to a bin in which all the samples in the bin are assigned 15 cycles of PCR for subsequent amplification. Any sample that has a qPCR Ct between 16 and 18 can be assigned to a bin in which all the samples in the bin are assigned 18 cycles of PCR for subsequent amplification. Any sample that has a qPCR Ct between 19 and 20 can be assigned to a bin in which all the samples in the bin are assigned 20 cycles of PCR for subsequent amplification. Any sample that has a qPCR Ct between 21 and 23 can be assigned to a bin in which all the samples in the bin are assigned 23 cycles of PCR for subsequent amplification. Any sample that has a qPCR Ct between 24 and 26 can be assigned to a bin in which all the samples in the bin are assigned 26 cycles of PCR for subsequent amplification. Any sample that has a qPCR Ct between 27 and 40 can be assigned to a bin in which all the samples in the bin are assigned 28 cycles of PCR for subsequent amplification.

TABLE 1

Non-Limiting Examples of Binning of Samples

| Bin Number | Min Ct | Max Ct | PCR Cycle Count |
| --- | --- | --- | --- |
| 1 | 0 | 9 | 9 |
| 2 | 10 | 12 | 12 |
| 3 | 13 | 15 | 15 |
| 4 | 16 | 18 | 18 |
| 5 | 19 | 20 | 20 |
| 6 | 21 | 23 | 23 |
| 7 | 24 | 26 | 26 |
| 8 | 27 | 40 | 28 |

In additional and alternative embodiments, the sorting can comprise identifying a PCR cycle count value range of all the samples and sorting all the samples into an integer number of bins using the PCR cycle count value range so that each bin has an equal number of samples or an equal number of samples within a range. The integer number of bins may be at least or at most or about 1, 2, 3, 4, 5, 6, 7, 8, 9 10, 11, 12, 13, 14, 15, 16, 17, 18, 19, 20 or more. The equal number of samples within a range may mean that each bin has an equal number of samples or the difference in size of samples between each bin does not exceed 1, 2, 3, 4, 5, 6, 7, or 8. In a particular embodiment, the integer number of bins may be eight bins, and each of eight bins has an equal number of samples. Thus, in one or more embodiments, the samples may be sorted evenly into a selected number N of bins.

In each round of selection for target-binding candidates, the size of each bin can be fixed or dynamic. In some embodiments, the size of each bin can be fixed across selection rounds. In other embodiments, the size of each bin can change in response to how wide the PCR cycle count range changes. For example, at earlier rounds, a larger bin size for each of an integer number of bins and PCR plates may be automatically generated based on a wider range of PCR cycle counts. But at later rounds of selection, when the data starts to converge, each of the integer number of bins and PCR plates may have a much smaller bin size, i.e., a smaller size of samples in each bin, based on a narrower range of PCR cycle counts. In a particular embodiment, the integer number is 8. Spreading out the samples across a large of bins, e.g., 8 bins, achieves a good accuracy normalization.

The workflow 200 can comprise, at step 240, generation of worklists, e.g., a forward worklist and a reverse worklist. The workflow 200 assigns two worklists to each bin. A forward worklist has instructions for samples of one bin to be selected from original wells of a source plate into a PCR plate to perform PCR based on the assigned common PCR cycle count of the bin. For example, the source plate may have individual wells A5, B5, and D5 that have the same Ct value and that are sorted into the same bin (e.g., A5, B5, and D5 refer to rows A, B, and D and the fifth column in a 96-well plate). The forward worklist may be generated to select samples from the same bin, i.e., from well A5, B5, and D5 into the same PCR plate for subsequent PCR amplification. In a reverse worklist, samples can be transferred back to the original wells in the source plate after PCR amplification.

The workflow 200 can comprise, at step 250, execution of a forward worklist. For example, the workflow 200 obtains PCR plates and assigns the PCR plates arbitrary barcodes. The forward worklist may be executed for a liquid handler to transfer samples from original wells in the source plate to corresponding PCR plates. Each bin that shares a common PCR cycle count for amplification may be assigned to a corresponding PCR plate with a particular barcode, and the assignment may be saved in a database. Accordingly, in one or more embodiments, a single PCR plate may receive only those samples sharing the common PCR cycle count for amplification.

The workflow 200 can comprise, at step 260, creating and sending instructions to a thermocycler for performing PCR amplification according to a forward worklist. The instructions are based on the common PCR cycle count for each bin. The instructions may check barcodes of each PCR plate against the database and notify a PCR thermocycler that which barcodes are ready for PCR. For example, once a plate of samples in a single bin have been transferred to a corresponding PCR plate, the workflow 200 may move the corresponding PCR plate to a PCR thermocycler and update a designated file with the barcode of the PCR plate. Because the database has a file containing a list of barcodes that match corresponding bins, the PCR thermocycler may access the database and read the file to see which barcodes have been loaded into the PCR plates of a thermocycler and compare to the database to identify the matching bins that have the corresponding Ct counts from quantification and the assigned common PCR cycle count for amplification. The instructions may also update the thermocycler on how many cycles of PCR (i.e., the assigned common cycle count for amplification) to run for corresponding samples according to the match between barcodes of PCR plates and bins of samples.

The workflow 200 can comprise, at step 270, executing reverse worklists to put processed samples back into a source plate. After PCR, reverse worklists may be executed to transfer processed samples, such as amplified samples in the PCR plates, back to original wells of the source plate so that amplified DNA for each original well is generated.

For example, the workflow 200 may first receive worklists from the database and execute worklists 1 and 2 to transfer samples from original wells to corresponding PCR plates. The workflow 200 may have the PCR plates transferred to a PCR thermocycler. The workflow 200 may notify the PCR thermocycler that barcodes 1 and 2 and their corresponding PCR plates are ready for PCR amplification. The PCR thermocycler may check how many PCR cycles of samples in the first and second bins match PCR plates 1 and 2 and then perform the corresponding PCR cycles to amplify samples in the first and second bins. The reverse worklists 1 and 2 may be executed to transfer amplified samples back to the original wells in the source plate. The workflow 200 can then check if worklists for barcodes 3 and 4 exist, and if they do, repeat the above steps for worklists 1 and 2. The workflow 200 may receive and execute worklists one at a time, two at a time, three at a time, four at a time, five at a time, six at a time or more at a time, depending on how many different PCR reactions can be performed at the same time.

The workflow 200 can comprise, at step 280, finishing this round and repeating another round of selection. Subsequent rounds of selection can involve the same workflow 200 including steps 210, 220, 230, 240, 250, 260, and 270.

Figure 3A:
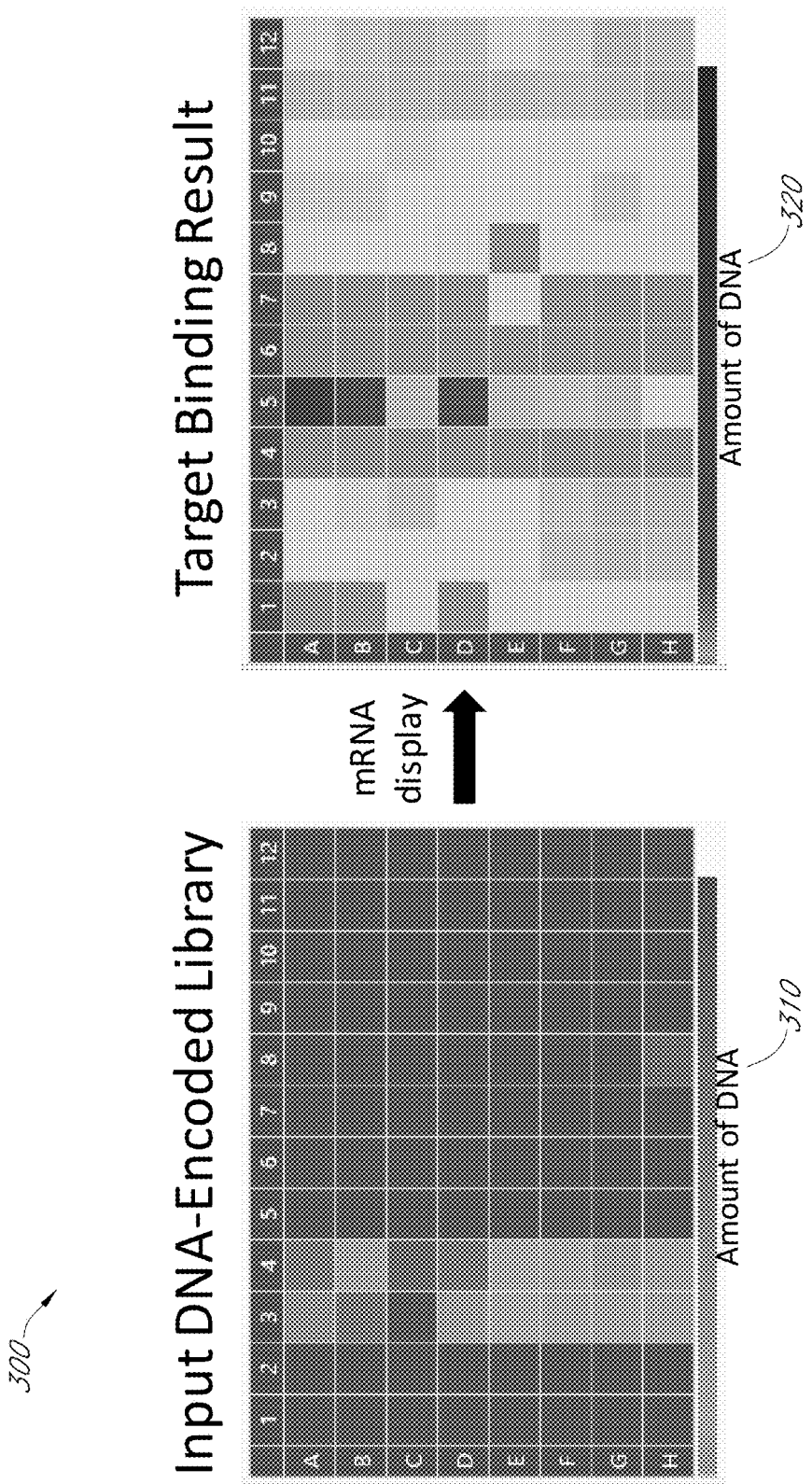
FIGS. 3A-3C illustrates non-limiting exemplary embodiments of a workflow for normalizing a plurality of libraries of DNA-containing compositions for identifying a candidate DNA conjugate for binding affinity to a binding target, in accordance with various embodiments.
Figure 3B:
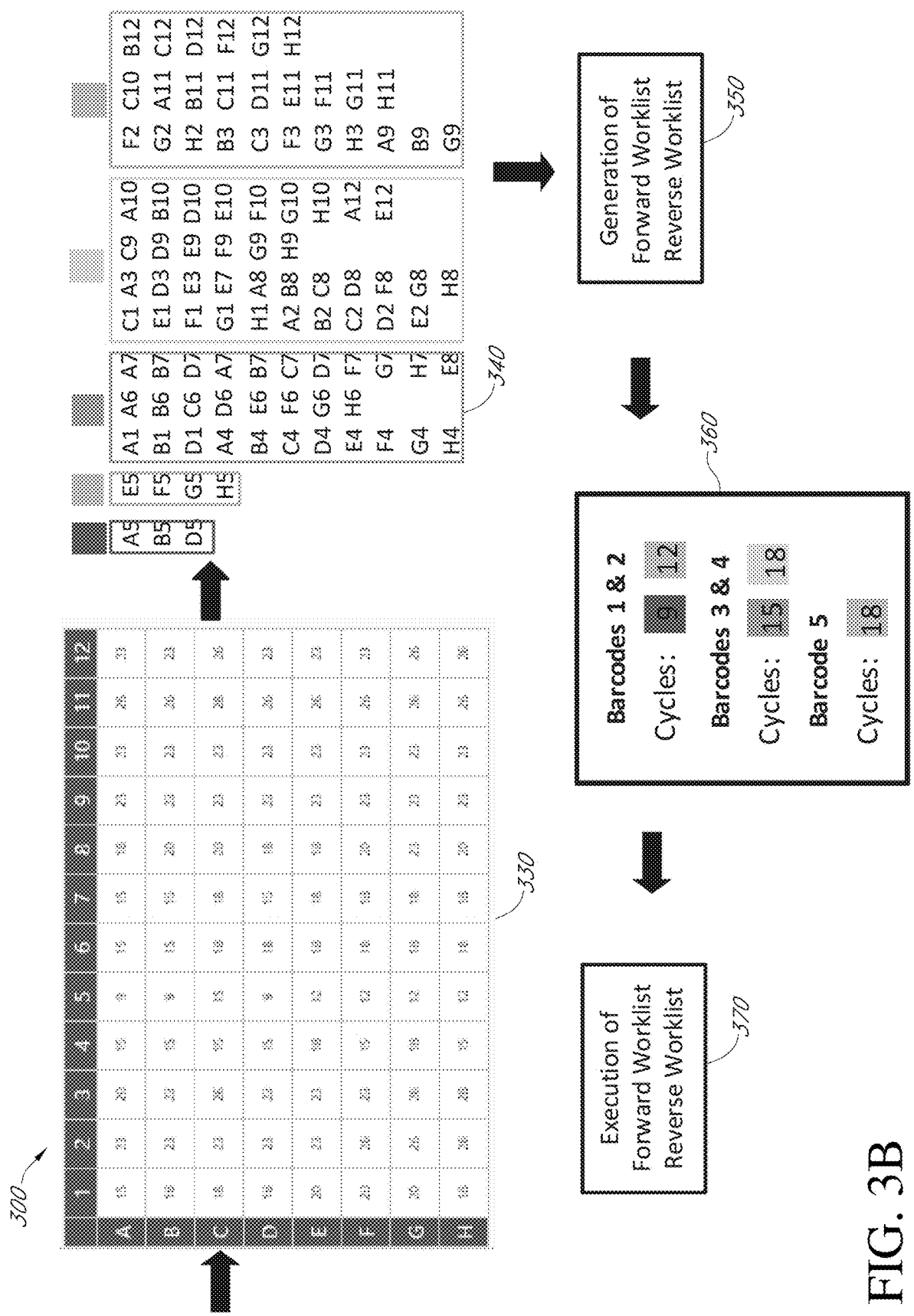
Figure 3C:
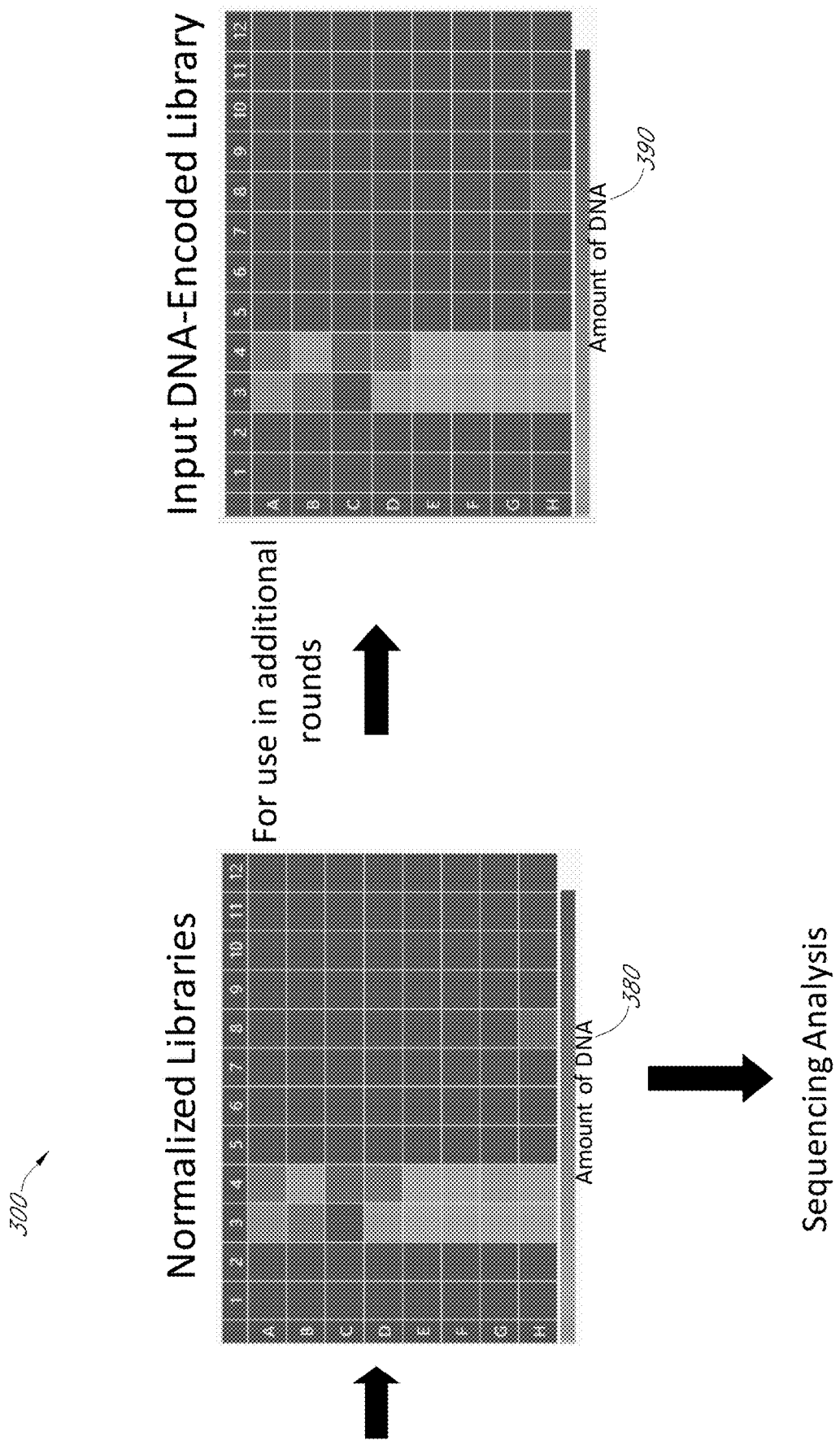

FIGS. 3A-3C are graphs showing non-limiting exemplary embodiments of a normalization workflow 300. The normalization workflow 300 can be repeated at the end of each round of selection (except the last round of selection) after positive selection for binding to a desired target or negative selection to remove libraries that bind to support without the desired target molecule so libraries with more DNA after selection are determined to do more PCR cycles for amplification to normalize DNA concentration in all the libraries.

In FIG. 3A, the normalization workflow 300 includes transforming input libraries 310, which contain DNA. into libraries 320 with target-binding results after mRNA display and target-binding selection, as illustrated in FIG. 1. The amount of DNA in individual wells can be visualized simultaneously as different grades of shading, different colors, different patterns, or a combination thereof in, for example, a heat map.

In FIG. 3B, DNA concentration in the libraries 320 with target-binding results is measured by qPCR and normalized across different wells. At step 330 of the normalization workflow 300, after qPCR, PCR cycles of each of the libraries 320 (e.g., each well in a multi-well plate) in FIG. 3A can be calculated as Ct values and exported to match corresponding wells. For example, a pre-set criterium can be used to assign a PCR cycle count for any sample based on adding or subtracting a pre-determined number from the Ct values.

At step 340 of the normalization workflow 300, wells with the same Ct values within a range from PCR quantification or wells with the same PCR cycle counts for future amplification within a range can be grouped together into five bins. For example, the first bin has wells A6, B5 and D5, all of which have qPCR Ct of 9. The second bin has wells E5, F5, G5, and H5, all of which have qPCR Ct of 12. The third bin has several wells, which have similar qPCR Ct of 15 and 18. The fourth bin has several wells, which have similar qPCR Ct of 18, 20, and 23. The fifth bin has several wells, which have qPCR Ct counts of 23 and 26. Each bin groups conjugates with same Ct values within a range and will be determined to share a common PCR cycle for subsequent amplification to normalize DNA amounts across all libraries in the same bin and across different bins.

At 350, a forward worklist that instructs to select samples of one bin from original wells of a source plate for transfer into a corresponding PCR plate and a reverse worklist that instructs to send samples back to the original wells in the source plate may be generated, for example, by a database.

At step 360 of the normalization workflow 300, each bin may be assigned to a corresponding PCR plate with an assigned barcode. For example, a barcode of 1 may be assigned to the bin with the lowest Ct range or value. A worklist, such as a forward and a reverse worklist, may be generated using the barcode with a list of samples in that bin. Then this process may repeat for all the bins. The bin with the second-lowest Ct range or value may have a barcode of 2, the bin with the third-lowest Ct range or value may have a barcode of 3, and so on until the bin with the highest CT range or value is assigned a barcode of N, which is the total number of bins. The number of bins may be at least, about or at most 5, 6, 7, 8, 9, 10, or any range or value derived therefrom, depending on the qPCR data. This may be a dynamic process with barcode assignment and assignment of bins to corresponding barcodes.

After all the bins have barcodes of PCR plates assigned and all the worklists have been generated, the worklists may be saved for a device such as a liquid handler to access and instruct to process the PCR plates for amplification according to the worklists. For example, the bins with similar common PCR cycles counts for amplification may be processed together. The first bin may have an assigned common PCR cycle count of 9 for amplification. The second bin may have an assigned common PCR cycle count of 12 for amplification. The third bin may have an assigned common PCR cycle count of 15 for amplification. The fourth bin may have an assigned common PCR cycle count of 18 for amplification. The fifth bin may have an assigned common PCR cycle count of 18 for amplification. The processing may be done from low PCR cycle counts to high PCR cycle counts, for example, PCR plates with barcodes 1 and 2 may be processed together, PCR plates with barcodes 3 and 4 may be processed together, PCR plate with barcode 5 may be processed subsequently.

As one non-limiting advantage of the present disclosure, samples in the bins with low PCR cycle counts are amplified to have a similar amount of DNA as samples in the bins with high PCR cycle counts after amplification so well-to-well variation can be minimized.

At 370, the forward worklist may be executed by a liquid handler to transfer samples in each bin from their original wells in a source plate to the assigned corresponding PCR plate and to perform PCR according to the assigned common PCR cycle count for each bin. After PCR, the reverse worklist may be executed by a liquid handler to transfer processed samples containing amplified DNA back to their respective original wells in the source plate.

In FIG. 3C, the workflow 300 continues to generate normalized libraries 380 that may have the same DNA concentration within a range across all the wells. The normalized libraries 380 may be used as input DNA 390 in a subsequent round of selection or be used for sequencing analysis.

IV.B. Exemplary Normalization Methods

Methods are provided for normalizing a plurality of libraries of DNA-containing compositions. The methods can be implemented via computer software or hardware. The methods can also be implemented on a computing device/system that can include a combination of engines for normalizing a plurality of libraries of DNA-containing compositions. In various embodiments, the computing device/system can be communicatively connected to one or more of a data source, sample analyzer (e.g., a genomic sequence analyzer), and display device via a direct connection or through an internet connection.

IV.B.1. Normalization for Performing PCR

Figure 4:
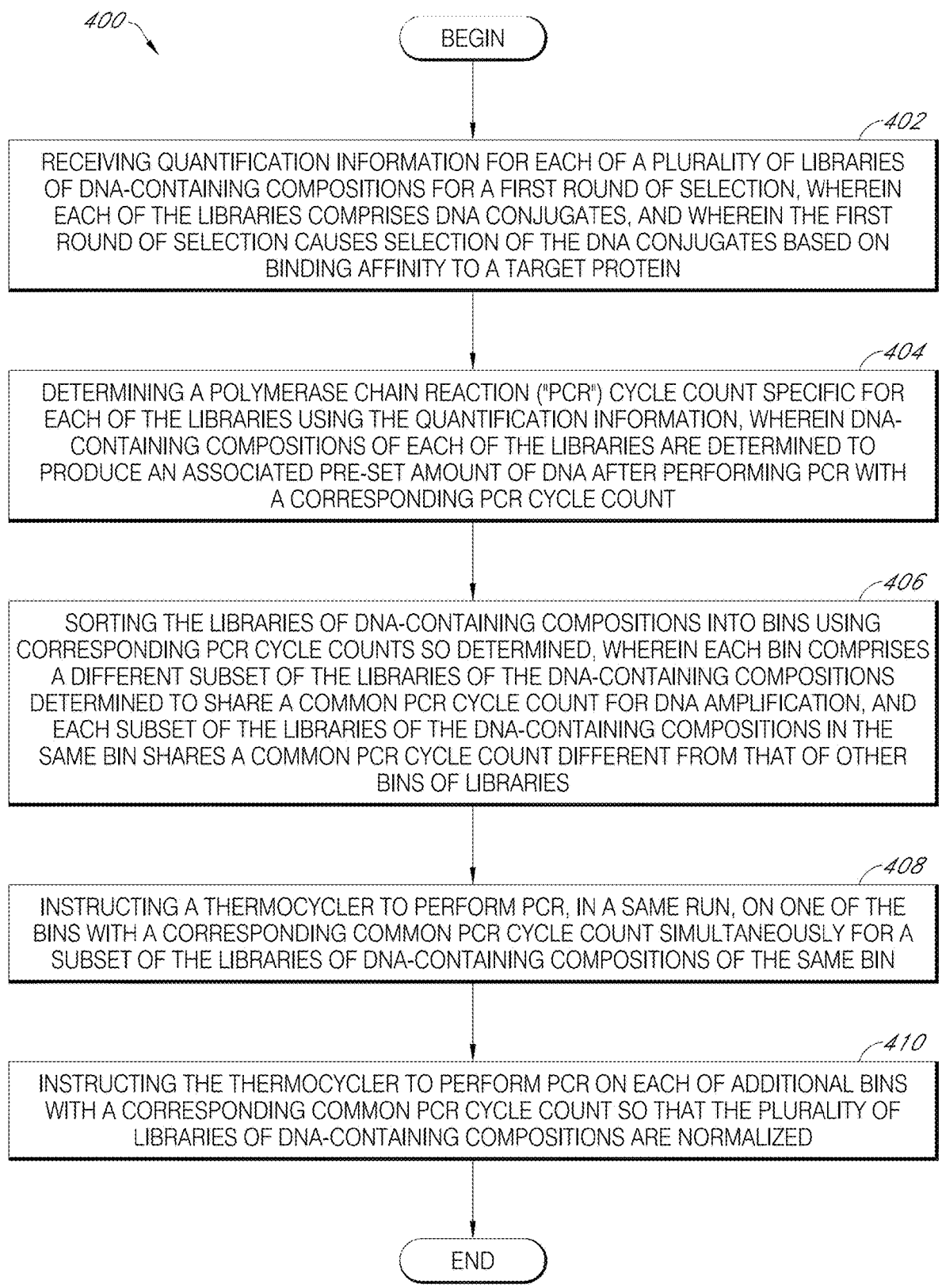
FIG. 4 is a flowchart illustrating a method for normalizing a plurality of libraries of DNA-containing compositions, in accordance with various embodiments.
Figure 5:
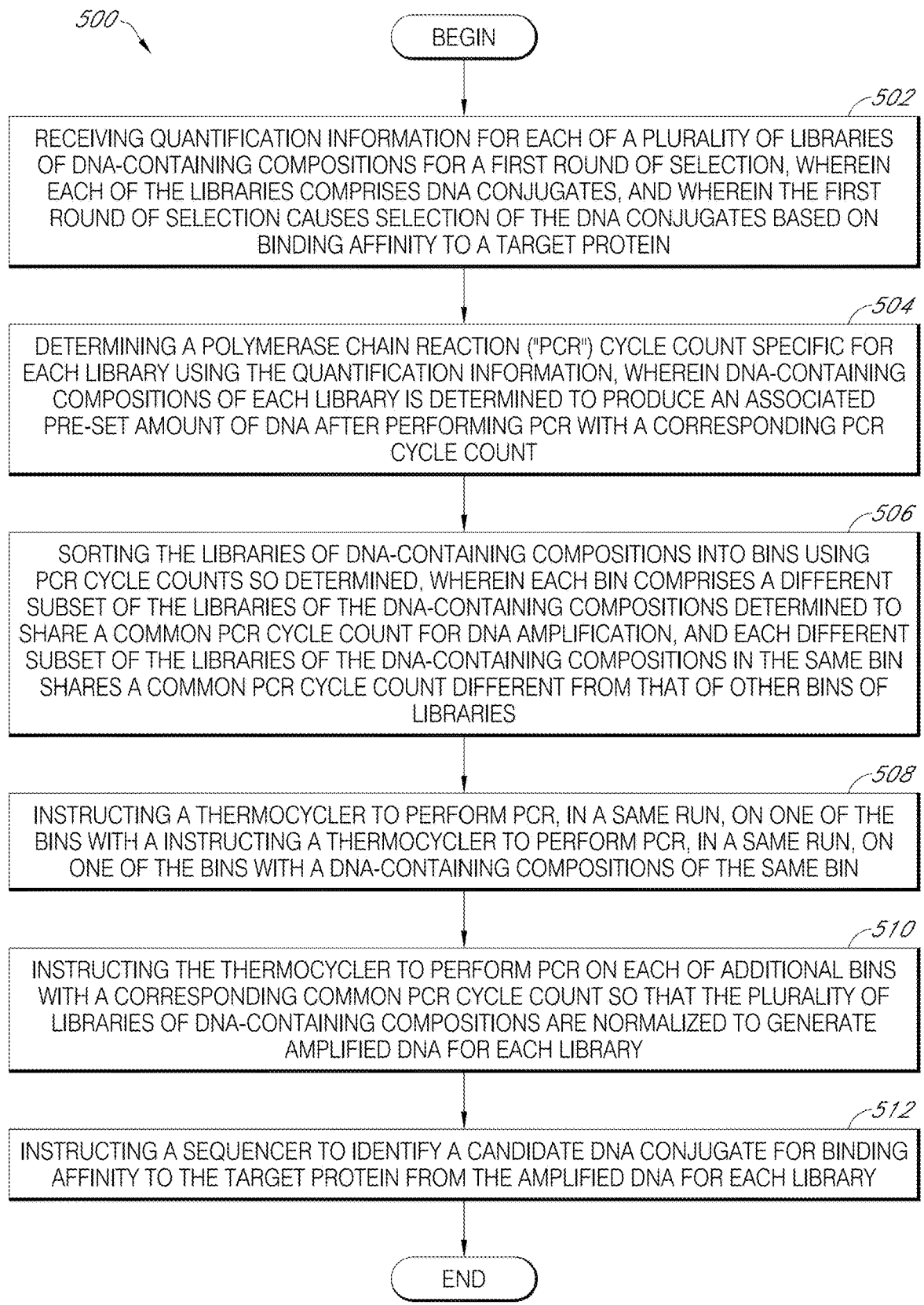
FIG. 5 is a flowchart illustrating a method for identifying a candidate DNA conjugate for binding affinity to a binding target, in accordance with various embodiments.

Referring now to FIG. 4, a flowchart illustrating a non-limiting example method 400 for normalization is disclosed, in accordance with various embodiments. The method 400 can comprise, at step 402, receiving quantification information for each of a plurality of libraries of DNA-containing compositions for a first round of selection. For example, each of the libraries comprises DNA conjugates, and the first round of selection causes selection of the DNA conjugates based on binding affinity to a target protein. For example, the DNA conjugates comprise peptides, such as macrocycles. The DNA conjugates can comprise peptides such as a linear or a cyclic peptide, or a combination thereof. The cyclic peptide can comprise macrocycles. The macrocycle can have one, two, three, or more rings, or a combination thereof. For example, the quantification information comprises cycle threshold (Ct) values for quantitative PCR (qPCR).

The method 400 can comprise, at step 404, determining a polymerase chain reaction ("PCR") cycle count specific for each of the libraries using the quantification information, wherein DNA-containing compositions of each of the libraries are determined to produce an associated pre-set amount of DNA after performing PCR with a corresponding PCR cycle count. The wells with lower amounts of DNA will have a higher Ct as determined by qPCR and will need to have more PCR cycle counts in amplification to normalize the difference between the wells with lower amounts of DNA and the wells with higher amounts of DNA.

The method 400 can comprise, at step 406, sorting the libraries of DNA-containing compositions into bins using corresponding PCR cycle counts so determined at step 404. Each bin may include a different subset of the libraries of the DNA-containing compositions determined to share a common PCR cycle count for DNA amplification. The libraries in each subset of the libraries of the DNA-containing compositions that are in the same bin share a common PCR cycle count different from that of other bins of libraries. In this manner, each bin may be assigned a unique PCR cycle count. For example, at least one of the bins includes more than one libraries of the DNA-containing compositions, such as 2, 3, 4, 5, 6, 7, 8, 9, 10 or more libraries, so libraries with similar PCR cycle counts can be grouped in the same bin to be assigned a common PCR cycle count for future amplification.

Each of the libraries of DNA-containing compositions of any one of the bins is determined to produce the same or similar amount of amplified DNA after performing PCR with a corresponding PCR cycle count for the same bin, in some embodiments. Therefore, the method can normalize the composition in each bin by determining a different PCR cycle count for each different bin so that there is the same or similar amount of DNA in each bin and across different bins. In some embodiments, the same or similar amount of DNA may have an amount within a pre-determined range, for example, an amount of DNA that differs by less than 25%, 20%, 15%, 10%, 9%, 8%, 7%, 6%, 5%, 4%, 3%, 2%, or 1%. The pre-determined range can be determined based on the binning of Ct values: for example, if there is more variance in Ct values of all conjugates in a bin, the pre-determined range is higher.

The method 400 can further comprise correlating each bin to a corresponding PCR plate for performing PCR amplification on DNA-containing compositions of the same bin with a corresponding common PCR cycle count on the corresponding PCR plate.

The method 400 can comprise, at step 408, instructing a thermocycler to perform PCR, in a same run, on one of the bins with a corresponding common PCR cycle count simultaneously for a subset of the libraries of DNA-containing compositions of the same bin. The method 400 can further comprise instructing a thermocycler to perform PCR on each of DNA-containing compositions of an additional bin with an additional corresponding common PCR cycle count simultaneously to produce additional amplified DNA The method 400 can further comprise generating a forward worklist comprising a first list corresponding to DNA-containing compositions of each bin to be transferred from original locations of a source plate into a PCR plate for performing PCR on DNA-containing compositions of the same bin with a corresponding common PCR cycle count to generate amplified DNA-containing compositions. The method 400 can further comprise generating a reverse worklist comprising a second list corresponding to the amplified DNA-containing compositions to be transferred from the PCR plate back to the original locations (wells) of a source plate.

The method 400 can comprise, at step 410, instructing the thermocycler to perform PCR on each of additional bins with a corresponding common PCR cycle count so that the plurality of libraries of DNA-containing compositions are normalized to minimize sample-to-sample variations. Normalized libraries can start next round of selection, including in vitro translation, reverse transcription, incubation with a desired target or an empty bead, wash of non-binders, elution of putative binders, and amplification of candidate binders by normalization as described herein.

IV.B.2. Normalization for Identifying a Candidate DNA Conjugate for Binding Affinity to a Target Protein Referring now to FIG. 5, a flowchart illustrating a non-limiting example method 500 for normalization in target-binding selection is disclosed, in accordance with various embodiments. The method can be used for identifying a candidate DNA conjugate for binding affinity to a target protein. The method can comprise, at step 502, receiving quantification information for each of a plurality of libraries of DNA-containing compositions for a first round of selection, wherein each of the libraries comprises DNA conjugates, and wherein the first round of selection causes selection of the DNA conjugates based on binding affinity to a target protein.

The method can comprise, at step 504, determining a polymerase chain reaction ("PCR") cycle count specific for each of the libraries using the quantification information, wherein DNA-containing compositions of each of the libraries is determined to produce an associated pre-set amount of DNA after performing PCR with a corresponding PCR cycle count.

The method can comprise, at step 506, sorting the libraries of DNA-containing compositions into bins, wherein each bin comprises a different subset of the libraries of the DNA-containing compositions determined to share a common PCR cycle count for DNA amplification, and each subset of the libraries of the DNA-containing compositions in the same bin shares a common PCR cycle count different from that of other bins of libraries. In some embodiments, at least one of the bins includes more than one libraries of the DNA-containing compositions, such as 2, 3, 4, 5, 6, 7, 8, 9, 10 or more libraries. Each of the libraries of DNA-containing compositions of any one of the bins is determined to produce a substantially identical amount of amplified DNA after performing PCR with a corresponding PCR cycle count for the same bin, in some embodiments. Therefore, the method can normalize the composition in each bin by determining a different PCR cycle count for each different bin so that there is the same or similar amount of DNA in each bin and across different bins. In some embodiments, the same or similar amount of DNA may have an amount within a pre-determined range, for example, an amount of DNA that differs by less than 25%, 20%, 15%, 10%, 9%, 8%, 7%, 6%, 5%, 4%, 3%, 2%, 1%, or any range or value derived therefrom.

The method can comprise, at step 508, instructing a thermocycler to perform PCR, in a same run, on one of the bins with a corresponding common PCR cycle count simultaneously for a subset of the libraries of the DNA-containing compositions of the same bin.

The method can comprise, at step 510, instructing the thermocycler to perform PCR on each of additional bins with a corresponding common PCR cycle count so that the plurality of libraries of DNA-containing compositions are normalized to generate amplified DNA for each of the libraries to minimize sample-to-sample variations.

The method can comprise, at step 512, instructing a sequencer to identify a candidate DNA conjugate for binding affinity to the target protein from the amplified DNA for each library. The candidate DNA conjugate can be identified by any available sequencing methods, such as next-generation sequencing. For example, the sequencer may include a next-generation sequencing system.

IV.B.3. Normalization for PCR Amplification using Dynamic Binning

Figure 6:
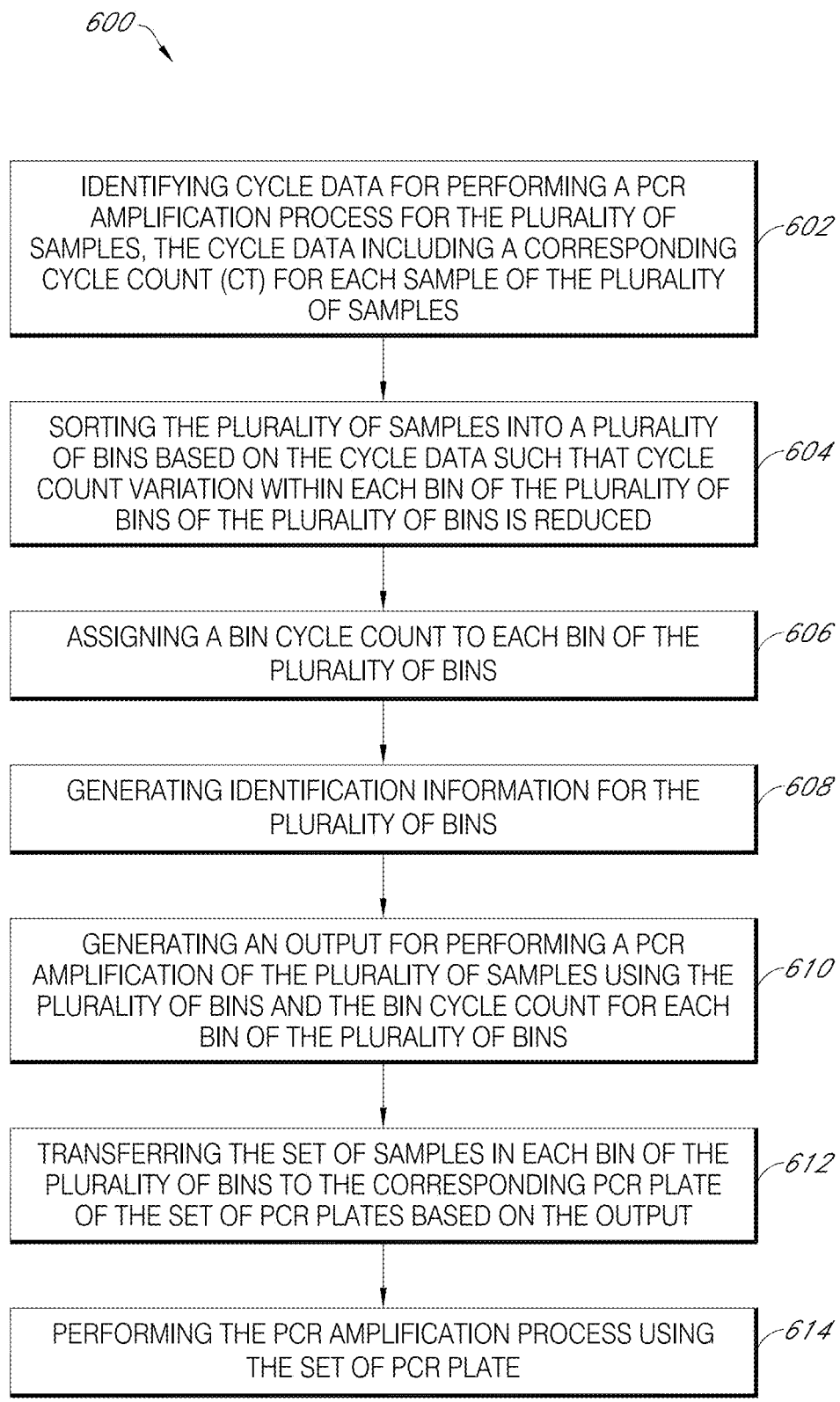
FIG. 6 is a flowchart illustrating a method for normalizing a polymerase chain reaction (PCR) amplification process for a plurality of samples containing DNA in accordance with various embodiments.

Referring now to FIG. 6, a flowchart illustrating a non-limiting example method 600 for normalizing a polymerase chain reaction (PCR) amplification process for a plurality of samples containing DNA in accordance with various embodiments. The method 600 may be one example of an implementation for the normalization that can be performed in step 140 of workflow 100 in FIG. 1. In one or more embodiment, the method 600 may be implemented using, for example, a computing system, such as computing device/analytics server 1206 in FIG. 12 described below. In some cases, the method 600 may be implemented using one or more engines of the computing system (e.g., one or more of PCR cycle count engine 1208, sorting engine 1210, and amplification engine 1212 in FIG. 12 described below.

The method 600 may comprise, at step 602, identifying cycle data for performing a PCR amplification process for the plurality of samples, the cycle data including a corresponding cycle count (Ct) for each sample of the plurality of samples. The plurality of samples may also be referred to as a plurality of libraries. The plurality of samples may include, for example, DNA-containing compositions. The cycle data may also be referred to as PCR cycle data. In one or more embodiments, the cycle data is received from a qPCR system. In other embodiments, the cycle data is generated using initial cycle data received from the qPCR system, the initial cycle data including an initial cycle count for each sample of the plurality of samples. Step 602 may include modifying the initial cycle count for the at least one sample of the plurality of samples. For example, in some cases, at least one sample of the plurality of samples may have an initial cycle count with an "undetermined" or null value. Step 602 may include changing the initial cycle count for the at least one sample to a preselected cycle count (e.g., a same cycle count as a minimum cycle count for the plurality of samples, 3 cycles, 5 cycles, 10 cycles, or some other number of cycles).

In some embodiments, step 602 may include adding a selected number of cycles to each initial cycle count for the plurality of samples, converting each non-integer cycle count into an integer cycle count (e.g., rounding up to the next integer), or both. The selected number of cycles added may be, for example, one, two, three, four, five, or some other number of cycles. In one example, a cycle count of 12.2 is converted to an integer value using the "whole number" portion of the cycle count, which is 12, or by rounding up to a nearest integer, which would be 13.

In other embodiments, step 602 may include deriving cycle data from some other form of data such as, for example, DNA amounts that are received from a qPCR system.

The method 600 may comprise, at step 604, sorting the plurality of samples into a plurality of bins based on the cycle data such that cycle count variation within each bin of the plurality of bins of the plurality of bins is reduced. Step 604 may be performed in any of a number of different ways. In one or more embodiments, step 604 may be performed by distributing, substantially evenly, the plurality of samples into the plurality of bins based on a selected range of cycle counts in the cycle data. Distributing, substantially evenly, may refer to sorting the plurality of samples into the plurality of bins such that an approximately same number (e.g., within one, two, three, or four of the same number) of samples are assigned to each bin.

The selected range of cycle counts may be, for example, between and inclusive of the minimum cycle count in the cycle data and the maximum cycle count in the cycle data. As another example, the selected range of cycle counts may be between and inclusive of a selected low cycle count (e.g., 3, 6, 5, 6, etc. cycle counts) and a selected high cycle count (e.g., 23, 24, 25, 26, 27, etc. cycle counts). The cycle count variation within each bin may be reduced by assigning samples that have a same cycle count or a corresponding cycle count within a selected range of cycles (e.g. within one, two, three, five, six, etc. cycles) of each other to a same bin.

In one or more embodiments, step 604 may be performed by first converting each non-integer cycle count in the cycle data into an integer cycle count to form modified cycle data. The non-integer cycle count (e.g., 13.2) may be rounded up to a nearest integer (e.g., 14). In some cases, the non-integer cycle count (e.g., 13.2) may be converted to its whole number (e.g., 13). The plurality of samples may then be distributed substantially evenly into the plurality of bins based on a selected range of cycle counts in the modified cycle data. This distribution may be performed in a manner similar to the manner described above.

In one or more embodiments, step 604 may further include modifying a distribution of the plurality of samples in the plurality of bins such that any samples of the plurality of samples having corresponding cycle counts associated with a same integer value are grouped together in a same bin. For example, in some cases, substantially even distribution of the plurality of samples into the plurality of bins may result in cycle counts associated with the same integer value being in two (or more) different bins. Cycle counts associated with a same integer value may include, for example, 13.2, 13.4, and 13.8, all of which correspond to the same integer value of 13. In some cases, these cycle counts may be considered as being associated with the same integer because rounding to the next nearest integer value results in the same integer value of 14. In this example, modifying the distribution ensures that all samples having cycle counts associated with the integer value of 13 (or, where rounding up, 14) are binned together in a same bin.

The method 600 can comprise, at step 606, assigning a bin cycle count to each bin of the plurality of bins. With respect to step 606, the bin cycle count is unique to each bin of the plurality of bins. In other words, no two bins may be assigned the same bin cycle count. The bin cycle count of a bin of the plurality of bins may be generated using, for example, a cycle count selected from a group consisting of a highest cycle count, an average cycle count, or a median cycle count of the set of samples in the bin. For example, the highest cycle count of the set of samples in a given bin may be used as the bin cycle count for that bin. Alternatively, the integer value associated with the highest cycle count may be used as the bin cycle count. In some cases, the bin cycle count is a sum of the highest cycle count for the set of samples and a selected cycle count or the integer value of such a sum. The selected cycle count may be, for example, one, two, three, four, five, or some other number of cycles. As one example, when the selected cycle count is two, if the highest cycle count of the set of samples in a bin is 10 cycles, then that bin may be assigned a bin cycle count of 12.

The method 600 can comprise, at step 608, generating identification information for the plurality of bins. The identification information may include a bin identifier for each bin of the plurality of bins. In one or more embodiments, this bin identifier is a unique identifier that uniquely identifies the bin. The bin identifier may be, for example, but is not limited to, a barcode. In one or more embodiments, the bin identifier assigned to a bin may be the same as a plate identifier associated with a PCR plate. For example, the bin identifier assigned to the bin may be the barcode of a PCR plate. Such an assignment indicates that the set of samples included in that bin are to be transferred to the PCR plate having the same barcode. In other embodiments, the bin identifier is one that can be matched to the plate identifier of a PCR plate using a database, spreadsheet, or other data format that matches up bin identifiers with plate identifiers. In some embodiments, the identification information may include additional information for the plurality of bins such as, for example, a total number of the bins, a total number of the set of samples in each bin, a minimum and/or maximum bin cycle count associated with each bin, other information that characterizes the plurality of bins as a whole and/or each individual bin, or a combination hereof.

The method 600 can comprise, at step 610, generating an output for performing a PCR amplification of the plurality of samples using the plurality of bins and the bin cycle count for each bin of the plurality of bins. The output may include, for example, a transfer output for use in transferring the set of samples in each bin of the plurality of bins to a corresponding PCR plate of a set of PCR plates using the identification information. For example, the identification information may be used to match the plurality of bins to the set of PCR plates so that each bin of the plurality of bins is matched to a corresponding PCR plate of the set of PCR plates.

In one or more embodiments, the transfer output includes a plurality of forward worklists for the plurality of bins. Each forward worklist of the plurality of forward worklists is associated with a corresponding bin of the plurality of bins. For example, a forward worklist for a bin may include an order in which the set of samples in the bin is to be selected from the source plate holding the plurality of samples and transferred to the PCR plate. The forward worklist may, for example, identify a sample by the row and column of its well in the source plate and may identify the corresponding well in the PCR plate to which the sample is to be transferred. In various embodiments, the transfer output may further include a reverse worklist for each bin that enables transferring the set of samples (after amplification) from the PCR plate back to the source plate.

The output generated at step 610 may further include, for example, an amplification output for use in performing the PCR amplification process. The amplification output may include, for example, instructions for a thermocycler that indicate the bin cycle count associated with each bin (and thereby, PCR plate) and/or the bin cycle count associated with each PCR plate (by virtue of the bin cycle count being associated with the bin corresponding to the PCR plate). The thermocycler may use this information to perform the PCR.

In one or more embodiments, each bin is uniquely matched to a PCR plate. In other words, no two bins may be assigned to the same PCR plate. In other embodiments, however, two bins may have the same identifier that corresponds to a same PCR plate. Assigning two bins to a same PCR plate may occur when, for example, the two bins differ in bin cycle count by less than a selected amount (e.g., differ by about 1, 0.75, 0.5, etc.).

The method 600 may comprise, at step 612, transferring the set of samples in each bin of the plurality of bins to the corresponding PCR plate of the set of PCR plates based on the output. For example, the set of samples in a bin may be transferred from a source plate to the corresponding PCR plate by a liquid handler.

The method 600 may comprise, at step 614, performing the PCR amplification process using the set of PCR plates. In one or more embodiments, the PCR amplification is performed with the number of cycles of amplification for each PCR plate of the set of PCR plates being determined by the bin cycle count for the one or more bins associated with each PCR plate. Prior to amplification, the plurality of samples have varying amounts of DNA. After the PCR amplification process has been performed, the plurality of samples in the set of PCR plates may be a plurality of amplified samples that have normalized amounts of DNA. In other words, the PCR amplification process is performed such that the amounts of DNA in the plurality of amplified samples are generally the same or similar (e.g., within selected tolerances of each other). For example, normalized amounts of DNA may be amounts of DNA that are within a threshold range (e.g., percent range, amount, etc.) of each other. As one example, normalized amounts of DNA may include amounts of DNA that are within 1%, 2%, 3%, 4%, 5%, 8%, 10%, 15%, or some other percent range of each other.

Figure 7:
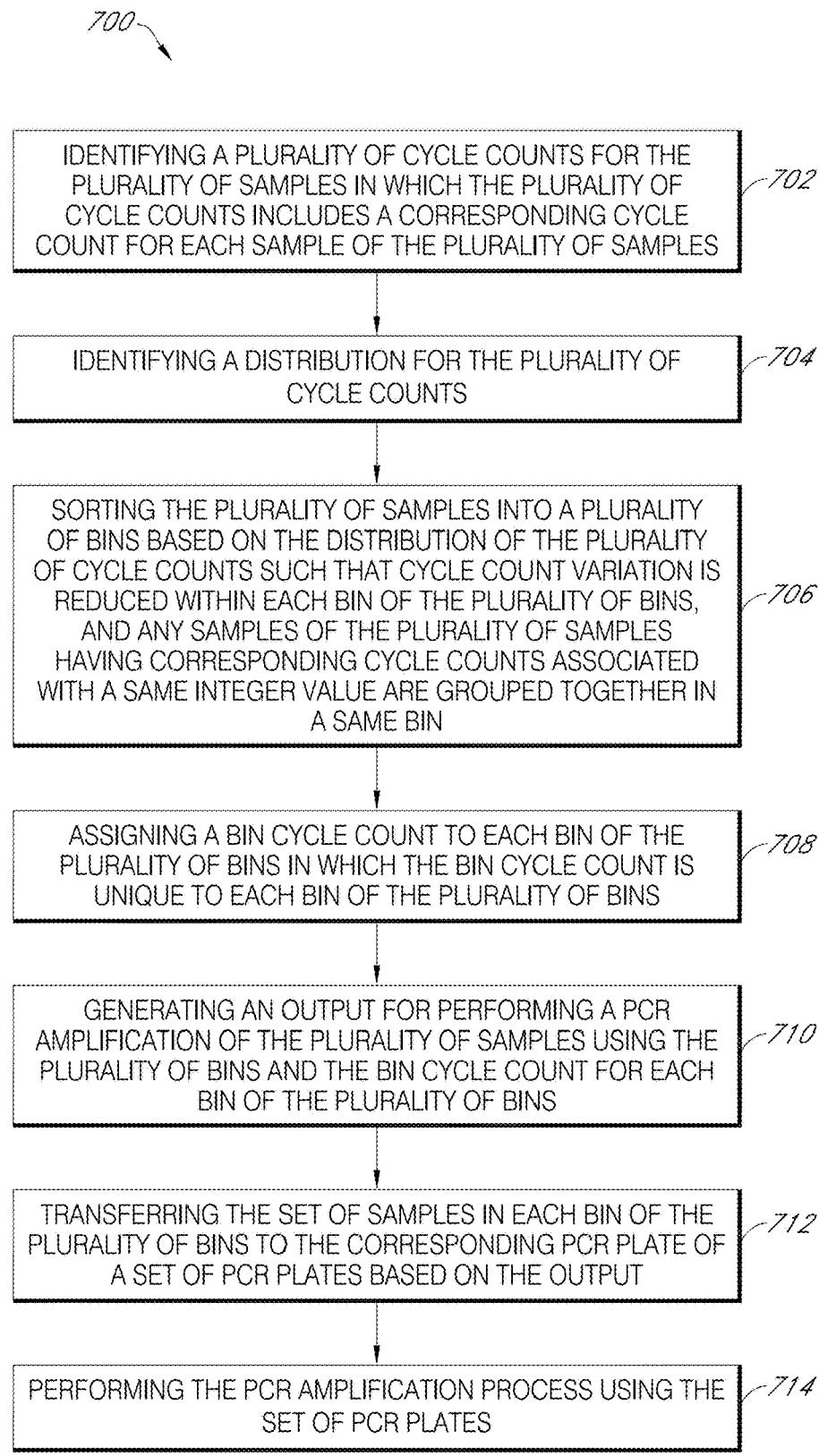
FIG. 7 is a flowchart illustrating of a method for normalizing a plurality of samples containing DNA depicted in accordance with various embodiments.

The method 600 may be repeated for each PCR run. In some cases, at step 608, the selected cycle count that is added to a highest cycle count of a bin to form the bin cycle count for that bin is dynamic in that the selected cycle count may be changed, as needed, from run to run. For example, if after one run, the data indicates lower than desired DNA amounts, the selected cycle count may be increased (e.g., from two to three). If, however, after another run, the data indicates that the DNA amounts are too high, the selected cycle count may be decreased (e.g., from two to one). The changes to the selected cycle may be made via user input entered by a user or via FIG. 7 is a flowchart illustrating of a non-limiting example method 700 for normalizing a plurality of samples containing DNA depicted in accordance with various embodiments. The method 700 may be another example of an implementation for the normalization that can be performed in step 140 of workflow 100 in FIG. 1.

The method can comprise, at step 702, identifying a plurality of cycle counts for the plurality of samples in which the plurality of cycle counts includes a corresponding cycle count for each sample of the plurality of samples. The plurality of cycle counts may be identified by, for example, receiving the plurality of cycle counts from a qPCR system. In one or more embodiments, the plurality of cycle counts are identified by receiving initial cycle counts from the qPCR system that are then modified (e.g., at least one of the initial cycle counts is modified) to form the plurality of cycle counts. This modification may be performed in a manner similar to the modification described above in step 602 of the method 600 described above with respect to FIG. 6.

The method can comprise, at step 704, identifying a distribution for the plurality of cycle counts. The distribution may be, for example, a histogram distribution. In one or more embodiments, between 60% and 100% of the plurality of cycle counts are within a selected range between and inclusive of a selected low cycle count and a selected high cycle count. The selected low cycle count may be, for example, 2, 3, 4, or 5 cycles. The selected high cycle count may be, for example, 22, 23, 24, 25, 26 or 27 cycles. Thus, in one or more embodiments, the selected range may be between, and inclusive of, 4 cycles and 24 cycles.

The method can comprise, at step 706, sorting the plurality of samples into a plurality of bins based on the distribution of the plurality of cycle counts such that cycle count variation is reduced within each bin of the plurality of bins, and any samples of the plurality of samples having corresponding cycle counts associated with a same integer value are grouped together in a same bin. Step 706 may be performed in any of a number of different ways.

In one or more embodiments, step 706 may include assigning any sample of the plurality of samples having a corresponding cycle count below the selected low cycle count to a first bin of the plurality of bins and assigning any sample of the plurality of samples having a corresponding cycle count above the selected high cycle count to a last bin of the plurality of bins. As one example, when there are 8 bins, the selected low cycle count is 4 cycles, and the selected high cycle count is 24 cycles, any sample having a corresponding cycle count below 4 cycles may be assigned to the first bin and any sample having a corresponding cycle count above 24 cycles may be assigned to the eighth bin. Thus, outlier cycle counts are binned in the first and last bins. A remaining portion of the plurality of samples may then be distributed between a set of bins between the first bin and the last bin.

In some cases, where there are no outlier cycle counts with respect to the selected range (e.g., 100% of the cycle counts are within the selected range), the plurality of samples may be distributed between the plurality of bins with a bias towards providing more bin separation between lower cycle counts as compared to higher cycle counts. For example, samples with lower cycle counts (e.g., between 4 and 16 cycle counts) may be distributed across more bins as compared to those samples with higher cycle counts (e.g., between 16 and 24 cycle counts).

In one or more embodiments, the plurality of samples are sorted into the plurality of bins, based on the distribution for the plurality of cycle counts, with a bias towards providing more bin separation between the cycle counts corresponding to the majority of the samples. For example, the plurality of samples may be sorted into the plurality of bins, based on the distribution for the plurality of cycle counts, with a bias towards providing more bin separation between a portion of the plurality of cycle counts falling within one standard deviation of a mean of the plurality of cycle counts as compared to another portion of the plurality of cycle counts falling outside the one standard deviation of the mean.

Step 706 may further include ensuring that all cycle counts associated with the same integer value are binned together. In some embodiments, two cycle counts may be considered associated with the same integer value if each of the two cycle counts contains a whole number that is the same integer value. For example, 11.42 and 11.75 would be both considered associated with the integer value of 11. In other embodiments, two cycle counts may be considered associated with the same integer value if each of the two cycle counts, when rounded up to the nearest integer, rounds up to the same integer value. For example, 11.42 and 11.75 would be both considered associated with the integer value of 12 because both cycle counts round up to 12.

The method can comprise, at step 708, assigning a bin cycle count to each bin of the plurality of bins in which the bin cycle count is unique to each bin of the plurality of bins. Step 708 may be implemented in different ways. Step 708 may be implemented in a manner similar to step 606 of the method 600 described above with respect to FIG. 6.

The method can comprise, at step 710, generating an output for performing a PCR amplification of the plurality of samples using the plurality of bins and the bin cycle count for each bin of the plurality of bins. Step 710 may be performed in a manner similar to step 608 of the method 600 described above with respect to FIG. 6.

The method can comprise, at step 712, transferring a set of samples in each bin of the plurality of bins to a corresponding PCR plate of a set of PCR plates based on the output. For example, the set of samples may be transferred from a source plate to the corresponding PCR plate.

The method can comprise, at step 714, performing a PCR amplification process using the set of PCR plates. The PCR amplification process may include performing a single PCR plate or a pair of PCR plates at a time. Once the PCR has been performed for the set of PCR plates, the plurality of samples among the set of PCR plates may be considered a plurality of amplified samples that have normalized amounts of DNA.

Figure 8:
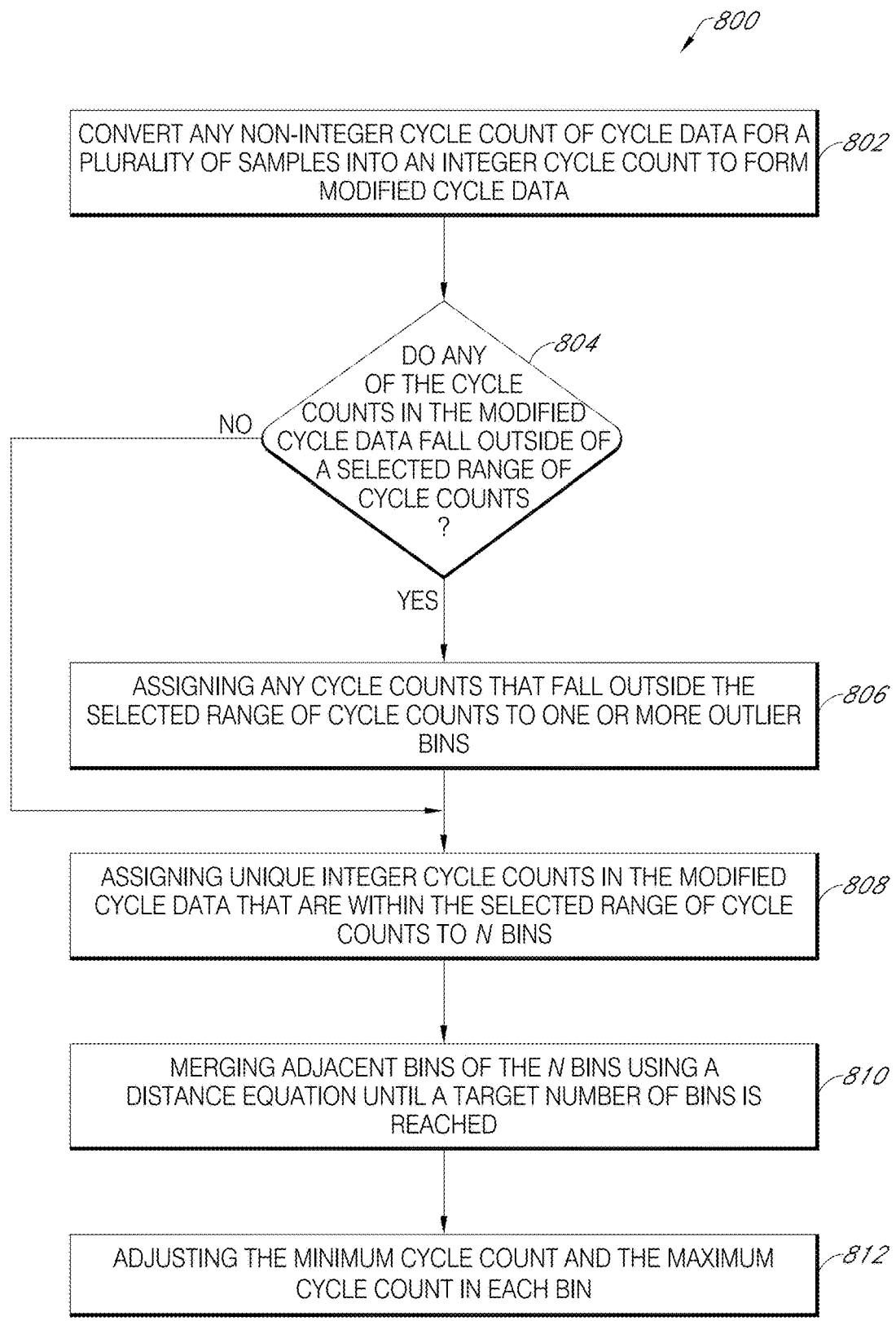
FIG. 8 is a flowchart illustrating of a non-limiting example method 800 for normalizing a plurality of samples containing DNA depicted in accordance with various embodiments.

FIG. 8 is a flowchart illustrating of a non-limiting example method 800 for normalizing a plurality of samples containing DNA depicted in accordance with various embodiments. The method 800 may be another example of an implementation for the normalization that can be performed in step 140 of workflow 100 in FIG. 1. In one or more embodiments, at least a portion of the method 800 may be used to implement step 604 of the method 600 described in FIG. 6 above and/or steps 704 and 706 of the method 700 described in FIG. 7 above.

The method 800 can comprise, at step 802, converting any non-integer cycle count of cycle data for a plurality of samples into an integer cycle count to form modified cycle data. A non-integer (e.g., decimal) cycle count may be rounded up to the nearest integer or down to the nearest integer. In some embodiments, all non-integer cycle counts are rounded up to the nearest integer. In some cases, step 802 may be one example of an implementation for at least a portion of step 602 of the method 600 described in FIG. 6 above and/or step 702 of the method 700 described in FIG. 7 above. In other cases, step 802 may be considered one example of an implementation for a portion of step 604 of the method 600 described in FIG. 6 above or 704 and/or 706 of the method 700 described in FIG. 7 above.

The method can comprise, at step 804, determining whether any of the cycle counts in the modified cycle data fall outside of a selected range of cycle counts. The selected range of cycle counts is a range between and inclusive of a selected low cycle count and a selected high cycle count. The selected low cycle count may be, for example, 2, 3, 4, or 5 cycles. The selected high cycle count may be, for example, 22, 23, 24, 25, 26 or 27 cycles. For example, the selected range of cycle counts may include, but is not limited to, 5 to 24 cycles.

If any of the cycle counts fall outside of the selected range of cycle counts, the method 800 can comprise, at step 806, assigning any cycle counts that fall outside the selected range of cycle counts to one or more outlier bins. For example, if a total number of available bins is 8 bins, then the first bin (e.g., bin 1) and the last bin (e.g., bin 8) may be used as outlier bins. Any cycle counts falling below the selected range of cycle counts may be assigned to the first bin and any cycle counts falling above the selected range of cycle counts may be assigned to the last bin. Assigning a cycle count to a bin includes assigning any sample associated with that cycle count to that bin.

The method can comprise, at step 808, assigning unique integer cycle counts of the modified cycle data that are within the selected range of cycle counts to N bins. In one or more embodiments, the unique integer cycle counts are placed in the N bins in ascending order, where N is the number of unique integer cycle counts.

The method can comprise, at step 810, merging adjacent bins of the N bins using a distance equation until a target number of bins is reached. The distance equation defines distance as the difference between a minimum cycle count in bin M and a minimum cycle count in bin M+1. Adjacent bins with the smallest distance are merged until the target number of bins is reached. The target number of bins may vary based on the cycle counts that fall within the selected range of cycle counts. For example, the target number of bins may be the total number of available bins (e.g., 8 bins) minus the number of outlier bins (e.g., 1 or 2) used at step 808.

The method can comprise, at step 812, adjusting the minimum cycle count and the maximum cycle count in each bin. For example, adjustments may be made to account for the rounding up and/or down of cycle counts at step 802. In one or more embodiments, the minimum cycle count in each bin is reduced by a first adjustment and the maximum cycle count in each bin is increased by a second adjustment. The first adjustment and the second adjustment may be the same or different. The first adjustment and the second adjustment may be, for example, 0.5. In other examples, the first adjustment may be 0.5 and the second adjustment may be 1.0, or vice versa.

With reference again to step 804, if none of the cycle counts fall outside of the selected range of cycle counts, the method 800 proceeds to step 808 as described above. In these such examples, the target number of bins in step 808 may simply be the total number of available bins.

In this manner, the method 800 is a process for sorting cycle counts into a plurality of bins. After this sorting has been performed, each bin may be assigned a bin cycle count, as described in step 606 of the method 600 in FIG. 6 and in step 708 of the method 700 in FIG. 7.

IV.B.4. Example Results of Dynamic Binning

FIG. 9A is a table illustrating a first round of dynamic binning using an upper bias in accordance with one or more embodiments. Table 900 shows the results of dynamic binning of samples and their corresponding cycle counts after a first round of qPCR analysis based on sorting with an upper bias.

FIG. 9B is a table illustrating a fourth round of dynamic binning using an upper bias in accordance with one or more embodiments. Table 902 shows the results of dynamic binning of samples and their corresponding cycle counts after a fourth round of qPCR analysis based on sorting with an upper bias.

FIG. 10 is a table illustrating a first round of dynamic binning using even distribution in accordance with one or more embodiments. Table 1000 shows the results of dynamic binning of samples and their corresponding cycle counts after a first round of qPCR analysis where the samples and their corresponding cycle counts have been evenly distributed across the available bins (8 bins).

FIG. 11A is a table illustrating a first round of dynamic binning with a bias towards samples having cycle counts within a selected range of cycle counts in accordance with one or more embodiments. Table 1100 shows the results of dynamic binning of samples and their corresponding cycle counts after a first round of qPCR analysis based on sorting with a bias towards samples having cycle counts within a selected range of cycle counts. This bias is used to reduce deviations in PCR amplifications from the desired cycle count (e.g., the cycle count derived via the qPCR system) for the samples within the selected range of cycle counts. Thus, this type of binning may help ensure that the greatest number of middle samples (within the selected range of cycle counts) are given the correct PCR cycles as compared to samples having outlier cycle counts (outside the selected range of cycle counts).

FIG. 11B is a table illustrating a fourth round of dynamic binning bias towards samples having cycle counts within a selected range of cycle counts in accordance with one or more embodiments. Table 1102 shows the results of dynamic binning of samples and their corresponding cycle counts after a first round of qPCR analysis based on sorting with the bias towards samples having cycle counts within the selected range of cycle counts.

IV.C. Normalization Systems

Figure 12:
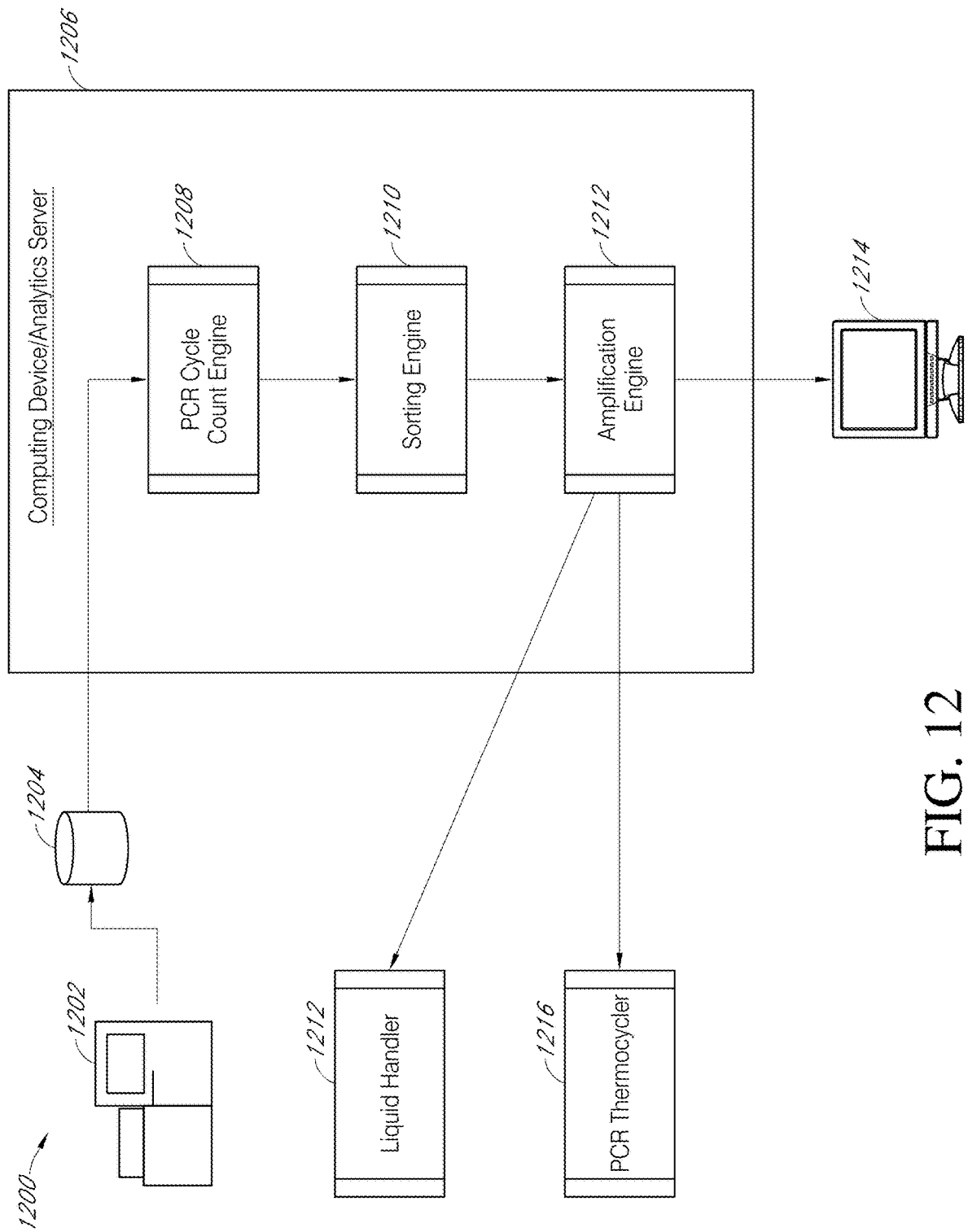
FIG. 12 is a schematic diagram of non-limiting examples of a system configured to normalize a plurality of libraries of DNA-containing compositions, in accordance with various embodiments.

FIG. 12 illustrates a non-limiting example system configured to normalize a plurality of libraries in target-binding selection, in accordance with various embodiments. The system 1200 can include various combinations of features, whether it be more or less features than that illustrated in FIG. 12. As such, FIG. 12 simply illustrate one example of a possible system.

The system 1200 includes a quantitative PCR unit 1202, a data storage unit 1204, a computing device/analytics server 1206, a display 1214, a PCR thermocycler 1216, and a liquid handler 1218. The quantitative PCR unit 1202 is a quantitative PCR instrument, i.e., a machine that amplifies and detects DNA. A quantitative PCR instrument combines the functions of a thermal cycler and a fluorimeter, enabling the process of quantitative PCR. Quantitative PCR instruments monitor the progress of PCR, and the nature of amplified products, by measuring fluorescence.

The quantitative PCR unit 1202 can be communicatively connected to the data storage unit 1204 by way of a serial bus (if both form an integrated instrument platform) or by way of a network connection (if both are distributed/separate devices). The generated qPCR datasets are stored in the data storage unit 1204 for subsequent processing. In various embodiments, one or more raw qPCR datasets can also be stored in the data storage unit 1204 prior to processing and analyzing. Accordingly, in various embodiments, the data storage unit 1204 can be configured to store qPCR datasets of the various embodiments herein that correspond to a plurality of libraries of DNA-containing compositions. In various embodiments, the processed and analyzed qPCR datasets can be fed to the computing device/analytics server 1206 in real-time for further downstream analysis.

The data storage unit 1204 can be communicatively connected to the computing device/analytics server 1206. In various embodiments, the data storage unit 1204 and the computing device/analytics server 1206 can be part of an integrated apparatus. In various embodiments, the data storage unit 1204 can be hosted by a different device than the computing device/analytics server 1206. In various embodiments, the data storage unit 1204 and the computing device/ analytics server 1206 can be part of a distributed network system. In various embodiments, the computing device/ analytics server 1206 can be communicatively connected to the data storage unit 1204 via a network connection that can be either a "hardwired" physical network connection (e.g., Internet, LAN, WAN, VPN, etc.) or a wireless network connection (e.g., Wi-Fi, WLAN, etc.). The computing device/analytics server 1206 can be a workstation, mainframe computer, distributed computing node (part of a "cloud computing" or distributed networking system), personal computer, mobile device, etc, according to various embodiments. The computing device/analytics server 1206 can be a client computing device. In various embodiments, the computing device/analytics server 1206 can be a personal computing device having a web browser (e.g., INTERNET EXPLORER™, FIREFOX™, SAFARI™, etc.) that can be used to control the operation of the qPCR unit 1202, data storage unit 1204, display 1214, PCR thermocycler 1216, and liquid handler 1218.

The computing system such as computer device/analytics sever 1206 is configured to host one or more PCR cycle count engines 1208, one or more sorting engines 1210, and one or more amplification engines 1212, according to various embodiments. An engine, such as PCR cycle count engine 1208, sorting engine 1210, and amplification engine 1212, may be implemented using software, firmware, hardware, or a combination thereof within the computing system (computer device/analytics sever 1206).

The PCR cycle count engine 1208 is configured to determine a polymerase chain reaction ("PCR") cycle count specific for each library using the quantification information, wherein DNA-containing compositions of each library is determined to produce an associated pre-set amount of DNA after performing PCR with a corresponding PCR cycle count.

The sorting engine 1210 is configured to sort the libraries of DNA-containing compositions into bins, wherein each bin comprises a different subset of the libraries of the DNA-containing compositions determined to share a common PCR cycle count for DNA amplification, and each different subset of the libraries of the DNA-containing compositions in each bin shares a different common PCR cycle count. In one or more embodiments, the sorting engine 1210 may be used to perform at least one of step 406 in FIG. 4, step 506 in FIG. 5, one or more of steps 602, 604, 606, 608, and 610 in FIG. 6, one or more of steps 702, 704, 706, 708, and 710 in FIG. 7, one or more of steps 802, 804, 806, 808, 810, and 812 in FIG. 8, or a combination thereof.

The amplification engine 1212 is configured to instruct a thermocycler 1216 to perform PCR, in a same run, on one of the bins with a corresponding common PCR cycle count simultaneously for a subset of the libraries of the DNA-containing compositions of the same bin. The amplification engine 1212 is configured to instruct the thermocycler 1216 to perform PCR on each library of DNA-containing compositions of additional bins so that the plurality of libraries of DNA-containing compositions are normalized. The amplification engine 1212 may be used to perform, for example, one or more of steps 408 and 410 in FIG. 4, one or more of steps 508 and 510 in FIG. 5, one or more of steps 610, 612, and 614 in FIG. 6, one or more of steps 710, 712, and 714 in FIG. 7, or a combination thereof.

The system 1200 further comprises a liquid handler 1218 configured to transfer each library of the same bin from a source plate to a PCR plate, wherein each library of the same bin is amplified by PCR on the PCR plate with a common PCR cycle count for the same bin to generate amplified DNA. The liquid handler 1218 is further configured to subject amplified DNA of all bins for an additional round of selection. The amplification engine 1212 can be communicatively coupled to the liquid handler 1218 to instruct the liquid handler 1218 to transfer samples back to a source plate.

During the time when the computing device/analytics server 1206 is receiving and processing data from the data storage unit 1204 or after the processing is done, an output of the results can be displayed as a result or summary on a display or client terminal 1214 that is communicatively connected to the computing device/analytics server 1206. The display or client terminal 1214 can be a client computing device. The display or client terminal 1214 can be a personal computing device having a web browser (e.g., INTERNET EXPLORER™ FIREFOX™, SAFARI™, etc.) that can be used to control the operation of the operation of the qPCR unit 1202, data storage unit 1204, PCR cycle count engine 1208, sorting engines 1210, amplification engine 1212, PCR thermocycler 1216, and the liquid handler 1218.

It should be appreciated that the various engines can be combined or collapsed into a single engine, component or module, depending on the requirements of the particular application or system architecture. Engines 1208, 1210, 1212 can comprise additional engines or components as needed by the particular application or system architecture.

V. Visualization of Quantification Information of Nucleotide-Containing Libraries Methods and systems can be provided herein for visualization and monitoring of quantification information of nucleotide-containing libraries in one or more rounds of selection for binding to a desired target. Currently, it is extremely challenging to visualize a large number of libraries simultaneously, and it can be time consuming and error-prone to compare different datasets from a large-scale selection by going back and forth between different datasets. Methods and systems provided herein allow simultaneous tracking and monitoring of large datasets in a more efficient and effective way.

V.A. Visualization Workflow

Figure 13:
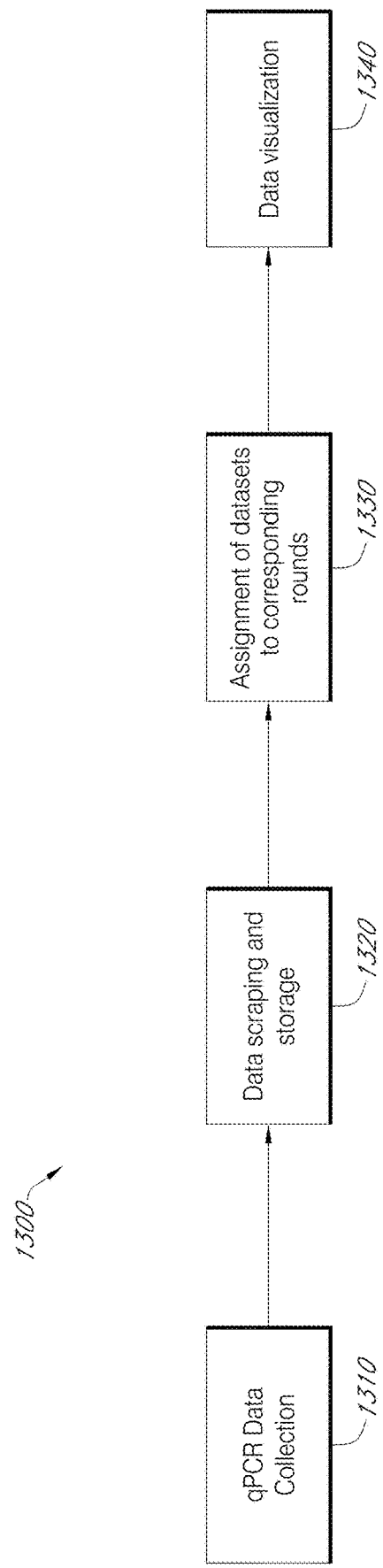
FIG. 13 illustrates non-limiting exemplary embodiments of a workflow for monitoring quantification information of each of a plurality of libraries to detect binding to a binding target in a graphical user interface, in accordance with various embodiments.

A general schematic workflow 1300 is provided in FIG. 13 to illustrate a non-limiting example process for visualizing and monitoring, on a graphical user interface, quantification information of a plurality of libraries of DNA-containing compositions to detect target binding, in accordance with various embodiments. Such a graphical user interface can enable simultaneous visual observation and comparison of a large number of libraries for a round of selection for target binding and for round-to-round comparison. The workflow can include various combinations of features, whether it be more or less features than that illustrated in FIG. 13. As such, FIG. 13 simply illustrate one example of a possible workflow.

The workflow 1300 can comprise, at step 1310, receiving quantification information for a plurality of libraries of DNA-containing compositions, including qPCR data. Receiving the quantification information may include collecting qPCR data for input molecules, positive molecules and negative molecules. Prior to each round of the target binding selection, qPCR is performed on aliquots of each of the mRNA-DNA-peptide conjugate libraries. The Ct produced by that pre-selection reaction represents a molecule number of each of the "input" libraries because it represents the total amount of each library before any binding steps and provides quantification information of input molecules. The quantification information of positive molecules includes the Ct produced by qPCR of aliquots of each of the mRNA-DNA-peptide conjugate libraries after a positive selection, i.e., the DNA captured from the target binding step of a positive selection. The quantification information of negative molecules includes the Ct produced by qPCR of aliquots of each of the mRNA-DNA-peptide conjugate libraries after a negative selection.

The qPCR data may be generated after a round of automated or manual library generation, target binding selection and DNA measurement by qPCR. Without further processing for visualization as described herein, the raw qPCR data, e.g., a table that comprises all the data in in all individual wells across all the rounds, are not easy to understand or interpret. For example, there may be 136 experiments in a 136-well plate that undergo four to ten target-binding selection rounds. On a table of qPCR raw data, the Ct levels for DNA in each well across all target-binding selection rounds are very challenging to be compared with another well in the same selection round or with the same well in another selection round to provide insight in an efficient and effective way.

Some embodiments of visualization methods as described herein may be able to solve these issues by displaying selected quantification information simultaneously to make better informed decisions.

The workflow 1300 can comprise, at step 1320, transfer quantification data and storing data in a database. Data transfer may include data scraping, in which a computer program extracts data from human-readable output coming from another program, e.g., Excel. The database stores each automatically or non-automatically exported dataset and all associated metadata (e.g., date, time, and plate barcode, etc.)

The workflow 1300 can comprise, at step 1330, assigning datasets to a corresponding round of selection. Each exported dataset may be assigned to a corresponding round of selection by a user, in accordance with some embodiments.

The workflow 1300 can comprise, at step 1340, visualizing data on a graphical display surface. Once each dataset is assigned to a corresponding round, all the heatmaps and charts are generated according to pre-set criteria or a selection of filters. For example, if a round-to-round comparison is selected, bar graphs of a round-to-round comparison of % mRNA recovery are generated (e.g., positive or negative recovery). For example, if mRNA % recovery is selected, heatmaps with mRNA % recovery of each well will be generated. For example, if negative molecules after round 1 is selected, heatmaps with qPCR results of negative molecules of each well after the first round are generated. For example, if positive molecules after round 1 is selected, heatmaps with mRNA % recovery of each well after the first round are generated (e.g., positive or negative recovery). For example, mRNA % positive recovery is defined as input/positive*100. For example, input molecules are multiplied by pre-defined multipliers, such as input molecules=(input qPCR results*20*50*10000), where a user inputs these multipliers beforehand. For example, heatmap color definition for positive or negative molecules are as follows: 10e8 is red, 10e10 is blue, and 10e13 is purple.

V.B. Visualization Methods

Methods are provided for visualizing quantification information of a plurality of libraries of DNA-containing compositions to detect target binding. The methods can be implemented via computer software or hardware. The methods can also be implemented on a computing device/system that can include a combination of engines for normalizing a plurality of libraries of DNA-containing compositions. The computing device/system can be communicatively connected to one or more of a data source, sample analyzer (e.g., a genomic sequence analyzer), and display device via a direct connection or through an internet connection.

Figure 14:
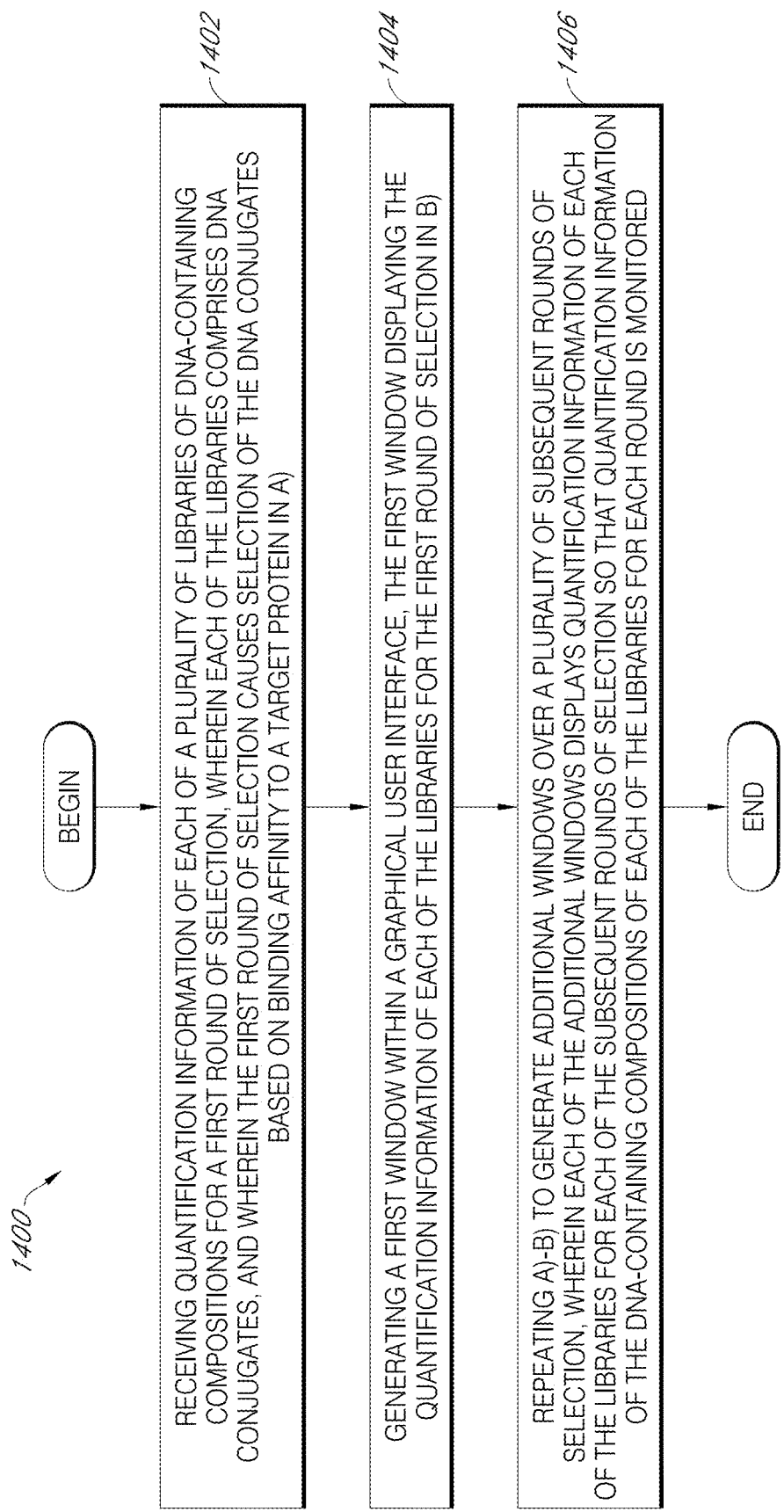
FIG. 14 is a flowchart illustrating a method for monitoring quantification information of each of a plurality of libraries to detect binding to a binding target binding in a graphical user interface, in accordance with various embodiments.

Referring now to FIG. 14, a flowchart illustrating a non-limiting example method 1400 for normalization is disclosed, in accordance with various embodiments. The method 1400 can comprise, at step 1402, receiving quantification information each of a plurality of libraries of DNA-containing compositions for a first round of selection. For example, each of the libraries of DNA-containing compositions comprises DNA conjugate. The DNA conjugates can comprise peptides such as a linear or a cyclic peptide, or a combination thereof. The cyclic peptide can be macrocycles, which can include monocycle, bicycle or tetracycle peptides. The method 1400 can be part of a screening assay where the DNA conjugates have been selected for binding affinity to a target protein for a first round of selection and for additional rounds of selection for the binding affinity.

For example, the quantification information of each of the libraries of DNA-containing compositions comprises cycle threshold (Ct) values for quantitative PCR (qPCR) input molecules, positive molecules, negative molecules, or any combination thereof. Additionally and alternatively, the quantification information of each of the libraries of DNA-containing compositions comprises a percentage of positive molecules relative to input molecules, a percentage of negative molecules relative to input molecule, or a combination thereof.

The quantification information of each of the libraries of DNA-containing compositions has been obtained from data scraping of qPCR data of each of the libraries, in some embodiments.

The method 1400 can comprise, at step 1404, displaying a first window within a graphical user interface on a computer screen, the first window containing the quantification information for each of the plurality of DNA-containing compositions.

The method 1400 can comprise, at step 1406, repeating steps 1402 and 1404 to generate a plurality of windows, wherein each of the plurality of windows correspond to quantification information for each of a plurality of subsequent rounds of selection so that quantification information of each of the libraries to detect target binding in the plurality of subsequent rounds is dynamically monitored.

Any window can comprise first graphical elements in a plurality of locations, in some embodiments. Each of the first graphical elements can be configured to represent each of the libraries. For example, each of the libraries is in one of individual spaces of a source plate, and each of the first graphical elements is configured to horizontally and vertically correspond to each of the individual spaces of the source plate. Each of the first graphical elements is located in the same location across different windows to represent a same well in a source plate, in some embodiments.

Any window can also comprise second graphical elements configured to visually distinguish quantification information of different libraries. The second graphical elements comprise color, numbers, or a combination thereof.

Any window can comprise third graphic elements configured to set up a filter to display quantification information of each of the libraries selected by the filter. For example, the filter is a user-selected scaffold, a user-selected codon, or a user-selected target. Any window can comprise first, second, third graphic elements, or any additional graphic elements, or a combination thereof.

The method 1400 further comprises displaying a selected window displaying quantification information of a selected round while hiding other windows. The method 1400 further comprises updating the graphic user interface to display a new window when a new round of selection is selected by a user. The method 1400 further comprises displaying the first window and the additional windows within the same graphical user interface so that a round-to-round comparison is generated. The method 1400 further comprises plotting a round-to-round comparison for each of the libraries of DNA-containing compositions on the graphic user interface.

V.C. Visualization Systems

Figure 15:
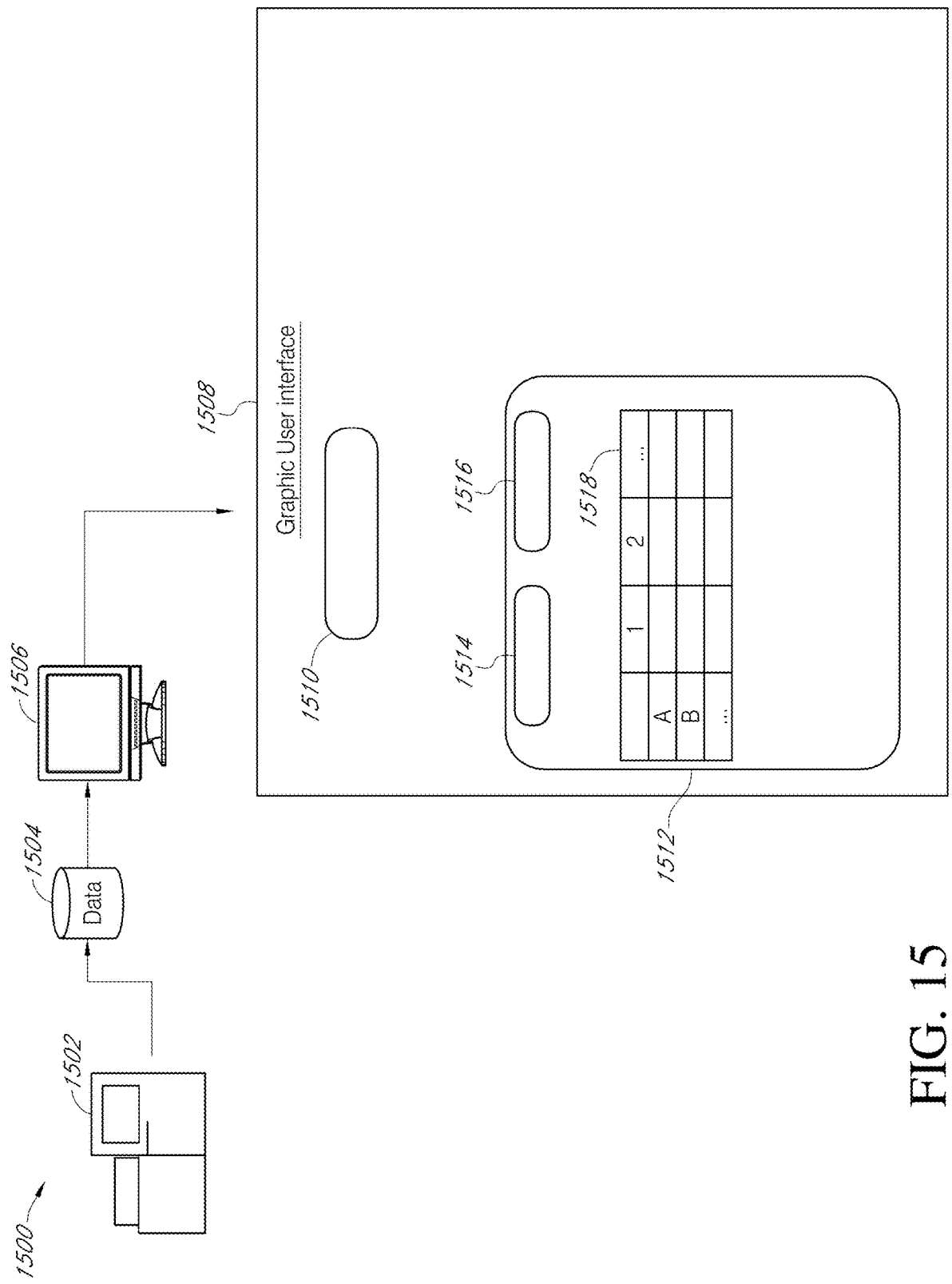
FIG. 15 illustrates non-limiting exemplary embodiments of a system and a graphic user interface for monitoring quantification information of each of a plurality of nucleotide-tagged peptide libraries to detect binding to a binding target in a graphical user interface, in accordance with various embodiments.

A general system 1500 is provided in FIG. 15 to illustrate a non-limiting example system for visualizing quantification information of a plurality of libraries of DNA-containing compositions to detect target binding, in accordance with various embodiments. The system 1500 can include various combinations of features, whether it be more or less features than that illustrated in FIG. 15. As such, FIG. 15 simply illustrate one example of a possible system.

The system 1500 includes a quantitative PCR unit 1502, a data storage unit 1504, and a computing device/analytics server/display 1506. The quantitative PCR unit 1502 is a quantitative PCR instrument, i.e., a machine that amplifies and detects DNA. A quantitative PCR instrument combines the functions of a thermal cycler and a fluorimeter, enabling the process of quantitative PCR. Quantitative PCR instruments monitor the progress of PCR, and the nature of amplified products, by measuring fluorescence.

The quantitative PCR unit 1502 can be communicatively connected to the data storage unit 1504 by way of a serial bus (if both form an integrated instrument platform) or by way of a network connection (if both are distributed/separate devices). The generated qPCR datasets are stored in the data storage unit 1504 for subsequent processing. One or more raw qPCR datasets can also be stored in the data storage unit 1504 prior to processing and analyzing. Accordingly, in various embodiments, the data storage unit 1504 can be configured to store qPCR datasets of the various embodiments herein that correspond to a plurality of libraries of DNA-containing compositions. The processed and analyzed qPCR datasets can be fed to the computing device/analytics server/display 1506 in real-time for further downstream analysis.

The data storage unit 1504 can be communicatively connected to the computing device/analytics server/display 1506. In various embodiments, the data storage unit 1504 and the computing device/analytics server/display 1506 can be part of an integrated apparatus. In various embodiments, the data storage unit 1504 can be hosted by a different device than the computing device/analytics server/display 1506. In various embodiments, the data storage unit 1504 and the computing device/analytics server/display 1506 can be part of a distributed network system. In various embodiments, the computing device/analytics server/display 1506 can be communicatively connected to the data storage unit 1504 via a network connection that can be either a "hardwired" physical network connection (e.g., Internet, LAN, WAN, VPN, etc.) or a wireless network connection (e.g., Wi-Fi, WLAN, etc.). In various embodiments, the computing device/analytics server/display 1506 can be a workstation, mainframe computer, distributed computing node (part of a "cloud computing" or distributed networking system), personal computer, mobile device, etc.

The computing device/analytics server/display 1506 can be a client computing device. In various embodiments, the computing device/analytics server/display 1506 can be a personal computing device having a web browser (e.g., INTERNET EXPLORER™ FIREFOX™, SAFARI™, etc.) that can be used to control the operation of the qPCR unit 1502 and data storage unit 1504.

One or more graphic user interfaces 1508 can be displayed on a display of the computing device/analytics server/display 1506. The computing device/analytics sever/display 1506 is configured to host one or more graphic user interfaces 1508 in various embodiments. For example, the graphic user interface 1508 includes graphical element 1510 to set up one or more filters to determine particular quantification information of each of the libraries to be displayed on the graphic user interface. Non-limiting exemplary formats of graphic elements can include blank fields, text boxes, check boxes, pull-down menus, or other input areas that a user can select data output.

For example, the graphical element 1510 is a filter such as a user-selected scaffold, a user-selected codon, or a user-selected target. For example, the graphical element 1510 is a menu of several options, including, but not limited to, positive recovery, negative recovery, input, positive melt curve, negative melt curve, enrichment, qPCR Ct Cycles, round 1, round 2, round 3, round 4, round 5, round 6, any appropriate round number, or any combination thereof.

After the graphical element 1510 is selected, one or more corresponding windows 1512 is displayed to show corresponding quantification information of all the wells in one assay. Each well represents each library in a plurality of libraries of DNA-containing compositions. For example, the windows 1512 display graphic elements 1514, 1516, and a grid 1518. The grid 1518 includes columns and row of quantification information matching corresponding columns and row of a source plate in the qPCR assay. The graphic element 1514 displays a label indicating content of the window 1512 and matching corresponding selection on the graphic element 1510. For example, when the graphic element 1510 is selected to display "input" and "round 1," the content of the grid 1518 will show qPCR results of input molecules at round 1, and the graphic element 1514 will show "input qPCR R1." The graphic element 1516 is a filter to select subsets of quantification information to be displayed on the window 1512, such as a selection of qPCR results of input, positive, or negative molecules.

Figure 16:
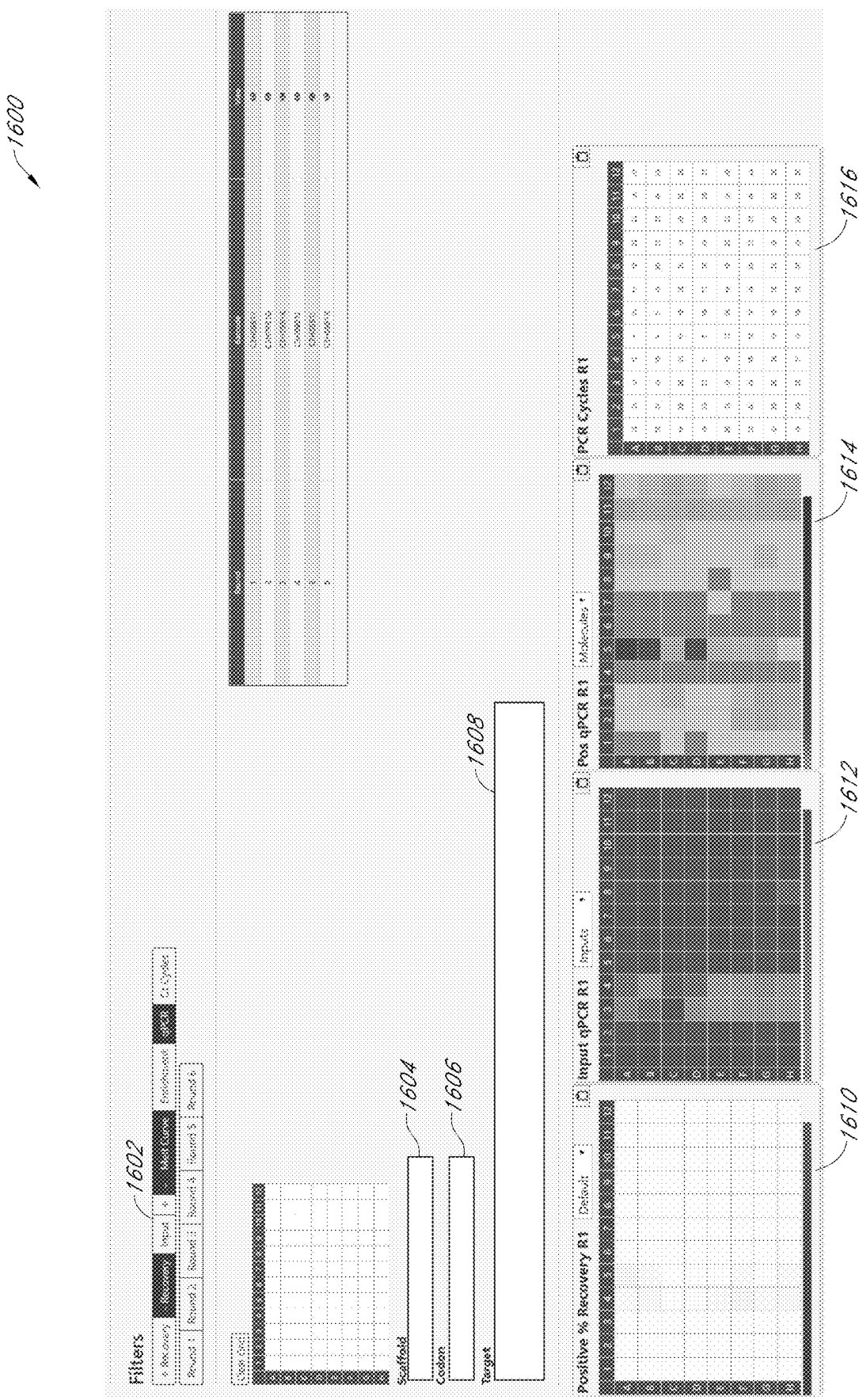
FIG. 16 depicts a screenshot illustrating non-limiting exemplary embodiments of a graphic user interface for monitoring quantification information of nucleotide-tagged peptide libraries to detect binding to a binding target in a graphical user interface, in accordance with various embodiments.

FIGS. 16-14 are graphs showing non-limiting exemplary embodiments of a graphic user interface for visualizing a plurality of libraries of DNA-containing compositions in target-binding selection.

FIG. 16 depicts a non-limiting exemplary embodiment of a graphic user interface 1600 for visualizing each of a plurality of libraries of DNA-containing compositions in selected target-binding selection rounds. The graphic user interface 1600 comprises filters 1602, 1604, 1606, and 1608 that can be selected to display filtered data from quantification information of the plurality of libraries of DNA-containing compositions. For examples, the filters include positive recovery, negative recovery, input, positive melt curve, negative melt curve, enrichment, qPCR, Ct cycles, or a round number (e.g., round 1 or R1, round 2 or R2, round 3 or R3, round 4 or R4, round 5 or R5, round 6 or R6, etc.). Additional filters may include, but not limited a filter 1604 that can select quantification information of peptides with certain scaffolds for visualization (e.g., peptide length in the plurality of peptide candidate libraries for target-binding selection, such as scaffold 1, scaffold 2, scaffold 3, etc.), a filter 1606 that can select quantification information of peptides with certain codons for visualization (e.g., codons used in making peptide candidates in the plurality of libraries for target-binding selection, such as codon table 1, codon table 2, codon table 3, etc.), a filter 1608 that can select quantification information of peptides that have been screened against certain targets for visualization (e.g., desired protein targets used in the target-binding screen or selection, such as target 1, target 2, target 3, etc.). With specific filters selected with particular user-selected values, for example, quantification information of each of the plurality of libraries of DNA-containing compositions or each selection round matching the selected filters can be displayed in exemplary graphs 1610-1216 and FIGS. 17-14.

Figure 17:
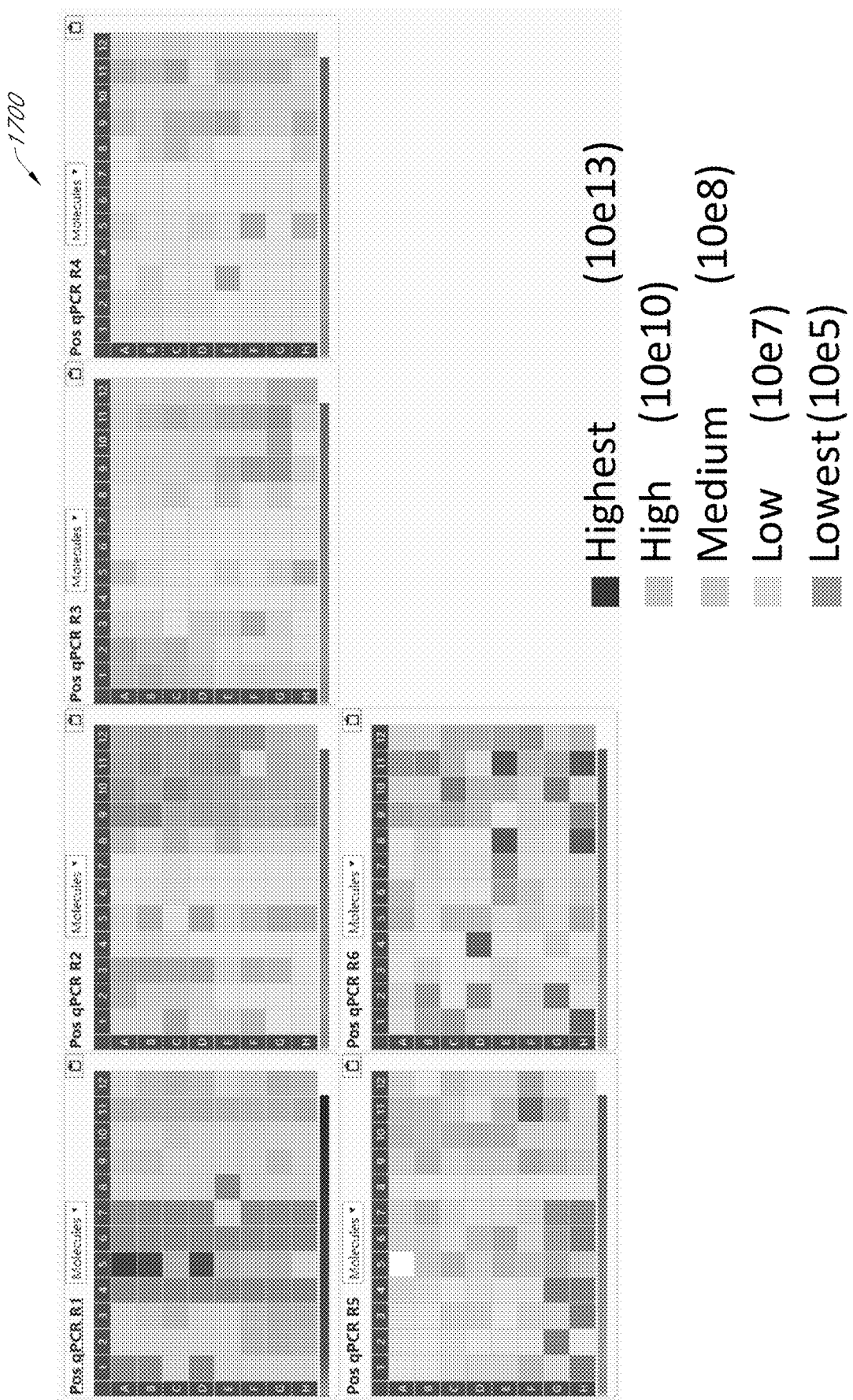
FIG. 17 depicts a screenshot illustrating non-limiting exemplary embodiments of a graphic user interface for monitoring quantification information of nucleotide-tagged peptide libraries to detect binding to a binding target in a graphical user interface, in accordance with various embodiments.

FIG. 17 depicts a non-limiting exemplary embodiment of a graphic user interface 1700 for visualizing each of a plurality of libraries of DNA-containing compositions in all target-binding selection rounds. FIG. 17 is a screen shot of the graphic user interface 1700, which comprises six heat maps using colors (colors are represented as shades of gray) to display different DNA concentration in each well (wells A1 to H12) for each round, respectively (R1=round 1, R2=round 2, R3=round 3, R4=round 4, R5=round 5, and R6=round 6). "Pos" refers to qPCR results of DNA concentration after a round of positive selection. This is a representative view to monitor the overall run progress of target-binding selection and can help a user to determine if another round of target-binding selection is desirable. For example, columns 4-7 in rounds 4, 5, and 6 showing medium DNA concentration were performing relatively well in target-binding selection as compared to other columns showing low DNA concentration. Visualization of this trend of enrichment continuing from one to another round to another round helps a user to build confidence that the whole selection process is working well.

Figure 18:
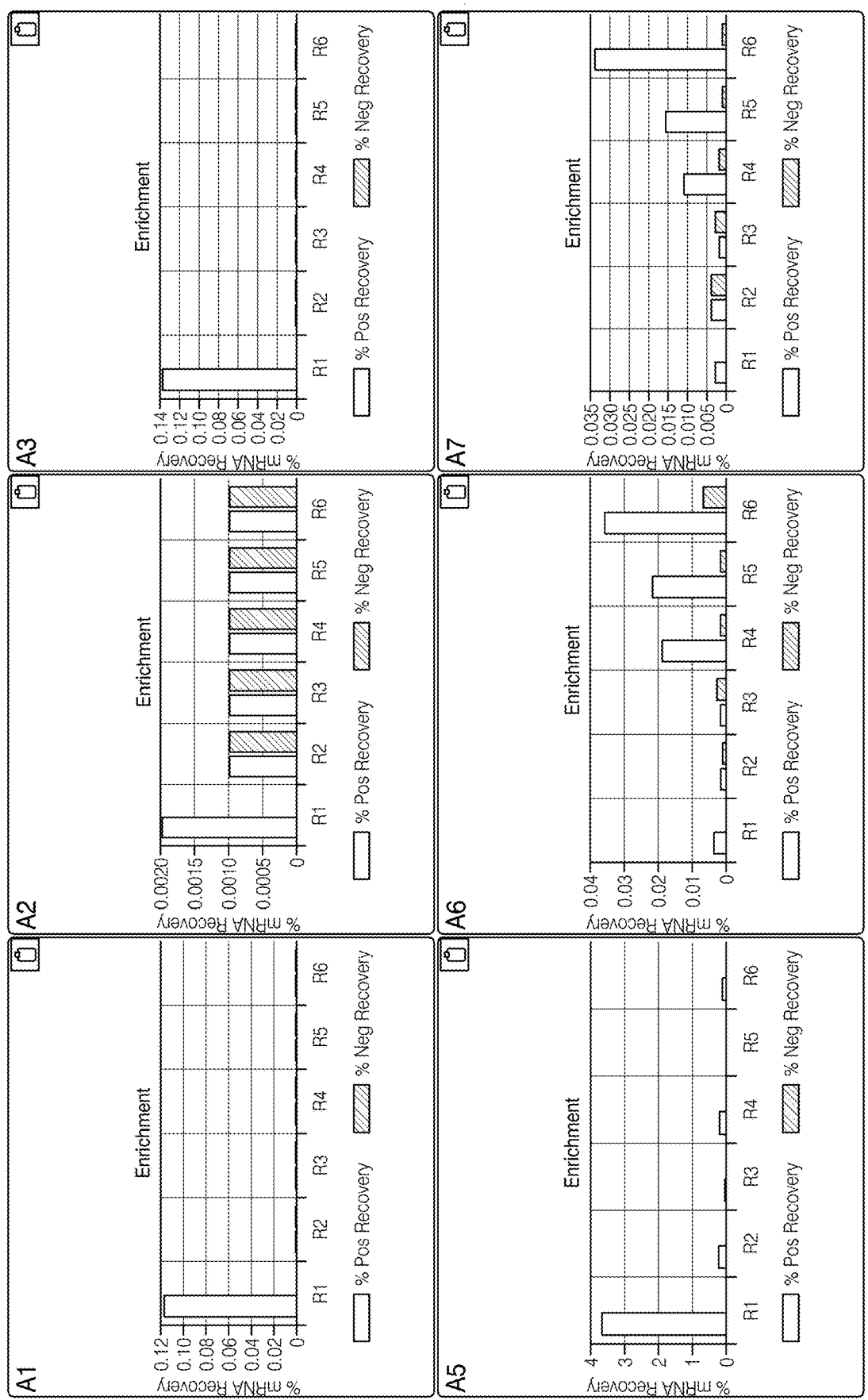
FIG. 18 depicts a screenshot illustrating non-limiting exemplary embodiments of a graphic user interface for monitoring quantification information of nucleotide-tagged peptide libraries to detect binding to a binding target in a graphical user interface, in accordance with various embodiments.

FIG. 18 depicts another non-limiting exemplary embodiment of a graphic user interface 1800 for visualizing each of a plurality of libraries of DNA-containing compositions in all target-binding selection rounds. FIG. 18 is a screen shot of the graphic user interface 1800. qPCR data of each of a plurality of libraries of DNA-containing compositions after each round of selection was parsed into % mRNA recovery by dividing positive molecules or negative molecules by input molecules. For example, % mRNA recovery (% positive recovery and % negative recovery) in each round was plotted as a bar chart to display the progression of the experiment for each individual well, e.g., each library of macrocycle-DNA-RNA conjugates. This data is reviewed each round, in conjunction with molecule heat maps as exemplified in FIG. 19 to decide if another round is desirable. % mRNA Recovery is calculated from qPCR data. % mRNA recovery represents the total mRNA/DNA/peptide amount of each library that was captured by the target. Positive molecules refer to the DNA captured from the target-binding step of a positive selection. Negative molecules refer to the DNA that remains after an empty-bead binding step of a negative selection. Prior to each round of the target binding selection, qPCR is performed on aliquots of each of the mRNA-DNA-peptide conjugate libraries. The Ct produced by that pre-selection reaction represents a molecule number of DNA in each of the "input" libraries because the Ct represents the total amount of each library before any binding steps.

VI. Computer-Implemented System

In various embodiments, any methods for normalization across different libraries with different DNA concentration and visualization of simultaneous selection of target-binding candidates can be implemented via software, hardware, firmware, or a combination thereof.

That is, as depicted in FIG. 12, the normalization methods disclosed herein can be implemented on a computer system such as computer system 1206 (e.g., a computing device/analytics server). The computer system 1206 (e.g., a computing device/analytics server) can be communicatively connected to a data storage 1204 and a display system 1214 via a direct connection or through a network connection (e.g., LAN, WAN, Internet, etc.). It should be appreciated that the computer system 1206 (e.g., a computing device/analytics server) depicted in FIG. 12 can comprise additional engines or components as needed by the particular application or system architecture.

Also, as depicted in FIG. 15, the visualization methods disclosed herein can be implemented on a computer system 1500. In various embodiments, the computer system 1500

(e.g., device/analytics/display system) can comprise a data storage 1504 communicatively connected to a computing device/analytics/display system 1506 via a direct connection or through a network connection (e.g., LAN, WAN, Internet, etc.). It should be appreciated that the computing device/analytics/display system 1500 depicted in FIG. 15 can comprise additional engines or components as needed by the particular application or system architecture.

Figure 19:
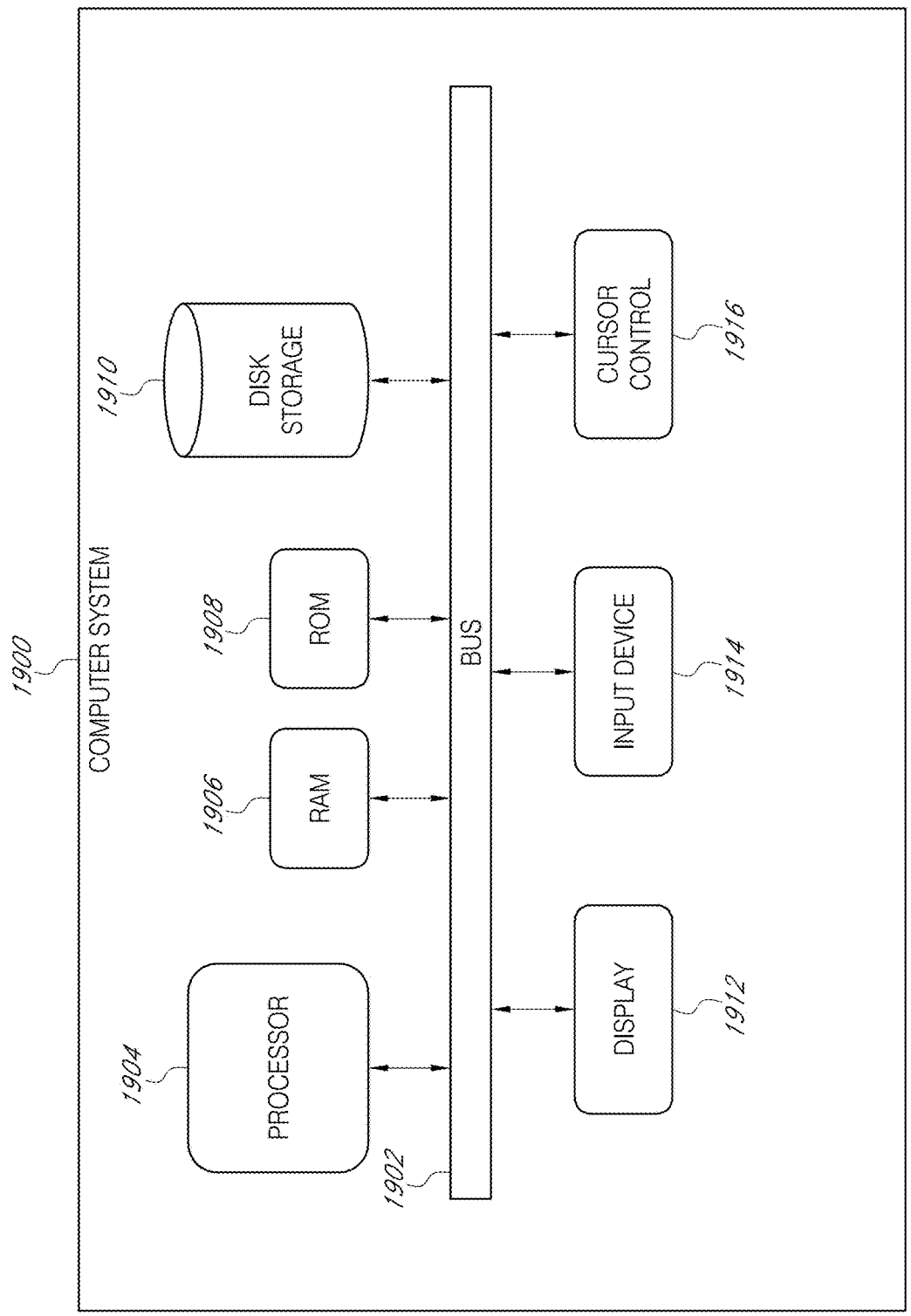
FIG. 19 is a block diagram of non-limiting examples illustrating a computer system configure to perform methods provided herein, in accordance with various embodiments.

FIG. 19 is a block diagram illustrating a computer system 1900 upon which embodiments of the present teachings may be implemented. In various embodiments of the present teachings, computer system 1900 can include a bus 1902 or other communication mechanism for communicating information and a processor 1904 coupled with bus 1902 for processing information. In various embodiments, computer system 1900 can also include a memory, which can be a random-access memory (RAM) 1906 or other dynamic storage device, coupled to bus 1902 for determining instructions to be executed by processor 1904. Memory can also be used for storing temporary variables or other intermediate information during execution of instructions to be executed by processor 1904. In various embodiments, computer system 1900 can further include a read only memory (ROM) 1908 or other static storage device coupled to bus 1902 for storing static information and instructions for processor 1904. A storage device 1910, such as a magnetic disk or optical disk, can be provided and coupled to bus 1902 for storing information and instructions.

In various embodiments, processor 1904 can be coupled via bus 1902 to a display 1912, such as a cathode ray tube (CRT) or liquid crystal display (LCD), for displaying information to a computer user. An input device 1914, including alphanumeric and other keys, can be coupled to bus 1902 for communication of information and command selections to processor 1904. Another type of user input device is a cursor control, such as a mouse, a trackball or cursor direction keys for communicating direction information and command selections to processor 1904 and for controlling cursor movement on display 1912. This input device 1914 typically has two degrees of freedom in two axes, a first axis (i.e., x) and a second axis (i.e., y), that allows the device to specify positions in a plane. However, it should be understood that input devices 1914 allowing for 3-dimensional (x, y and z) cursor movement are also contemplated herein.

Consistent with certain implementations of the present teachings, results can be provided by computer system 1900 in response to processor 1904 executing one or more sequences of one or more instructions contained in memory 1906. Such instructions can be read into memory 1906 from another computer-readable medium or computer-readable storage medium, such as storage device 1910. Execution of the sequences of instructions contained in memory 1906 can cause processor 1904 to perform the processes described herein. Alternatively, hard-wired circuitry can be used in place of or in combination with software instructions to implement the present teachings. Thus, implementations of the present teachings are not limited to any specific combination of hardware circuitry and software.

The term "computer-readable medium" (e.g., data store, data storage, etc.) or "computer-readable storage medium" as used herein refers to any media that participates in providing instructions to processor 1904 for execution. Such a medium can take many forms, including but not limited to, non-volatile media, volatile media, and transmission media. Examples of non-volatile media can include, but are not limited to, dynamic memory, such as memory 1906. Examples of transmission media can include, but are not limited to, coaxial cables, copper wire, and fiber optics, including the wires that comprise bus 1902.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, another memory chip or cartridge, or any other tangible medium from which a computer can read.

In addition to computer-readable medium, instructions or data can be provided as signals on transmission media included in a communications apparatus or system to provide sequences of one or more instructions to processor 1904 of computer system 1900 for execution. For example, a communication apparatus may include a transceiver having signals indicative of instructions and data. The instructions and data are configured to cause one or more processors to implement the functions outlined in the disclosure herein. Representative examples of data communications transmission connections can include, but are not limited to, telephone modem connections, wide area networks (WAN), local area networks (LAN), infrared data connections, NFC connections, etc.

It should be appreciated that the methodologies described herein, flow charts, diagrams and accompanying disclosure can be implemented using computer system 1900 as a standalone device or on a distributed network or shared computer processing resources such as a cloud computing network.

The methodologies described herein may be implemented by various means depending upon the application. For example, these methodologies may be implemented in hardware, firmware, software, or any combination thereof. For a hardware implementation, the processing unit may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, electronic devices, other electronic units designed to perform the functions described herein, or a combination thereof.

In various embodiments, the methods of the present teachings may be implemented as firmware and/or a software program and applications written in conventional programming languages such as C, C++, Python, etc. If implemented as firmware and/or software, the embodiments described herein can be implemented on a non-transitory computer-readable medium in which a program is stored for causing a computer to perform the methods described above. It should be understood that the various engines described herein can be provided on a computer system, such as computer system 1900, whereby processor 1904 would execute the analyses and determinations provided by these engines, subject to instructions provided by any one of, or a combination of, memory components 1906/1508/1510 and user input provided via input device 1914.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

In describing the various embodiments, the specification may have presented a method and/or process as a particular sequence of steps. However, to the extent that the method or process does not rely on the particular order of steps set forth herein, the method or process should not be limited to the particular sequence of steps described, and one skilled in the art can readily appreciate that the sequences may be varied and still remain within the spirit and scope of the various embodiments.

VII. Recitation of Embodiments

Embodiment 1: A method for normalizing a plurality of libraries of DNA-containing compositions, comprising: receiving quantification information for each of a plurality of libraries of DNA-containing compositions for a first round of selection, wherein each of the libraries comprises DNA conjugates, and wherein the first round of selection causes selection of the DNA conjugates based on binding affinity to a target protein; determining a polymerase chain reaction ("PCR") cycle count specific for each of the libraries using the quantification information, wherein DNA-containing compositions of each of the libraries are determined to produce an associated pre-set amount of DNA after performing PCR with a corresponding PCR cycle count; sorting the libraries of DNA-containing compositions into bins using corresponding PCR cycle counts so determined, wherein each bin comprises a different subset of the libraries of the DNA-containing compositions determined to share a common PCR cycle count for DNA amplification, and each subset of the libraries of the DNA-containing compositions in the same bin shares a common PCR cycle count different from that of other bins of libraries; instructing a thermocycler to perform PCR, in a same run, on one of the bins with a corresponding common PCR cycle count simultaneously for a subset of the libraries of DNA-containing compositions of the same bin; and instructing the thermocycler to perform PCR on each of additional bins with a corresponding common PCR cycle count so that the plurality of libraries of DNA-containing compositions are normalized.

Embodiment 2: The method of Embodiment 1, wherein the DNA conjugates comprise peptides.

Embodiment 3: The method of Embodiment 2, wherein the peptides comprise macrocycles.

Embodiment 4: The method of any one of Embodiments 1-3, wherein the quantification information comprises cycle threshold (Ct) values for quantitative PCR (qPCR).

Embodiment 5: The method of any one of Embodiments 1-4, wherein at least one of the bins includes more than one libraries of the DNA-containing compositions.

Embodiment 6: The method of any one of Embodiments 1-5, wherein each of the libraries of DNA-containing compositions of any one of the bins is determined to produce a same amount of amplified DNA after performing PCR with a corresponding PCR cycle count for the same bin.

Embodiment 7: The method of any one of Embodiments 1-6, further comprising instructing a thermocycler to perform PCR on each of DNA-containing compositions of an additional bin with an additional corresponding common PCR cycle count simultaneously to produce additional amplified DNA.

Embodiment 8: The method of any one of Embodiments 1-7, further comprising correlating each bin to a corresponding PCR plate for performing PCR on DNA-containing compositions of the same bin with a corresponding common PCR cycle count on the corresponding PCR plate.

Embodiment 9: The method of any one of Embodiments 1-8, further comprising generating a forward worklist comprising a first list corresponding to DNA-containing compositions of each bin to be transferred from original locations of a source plate into a PCR plate to generate amplified DNA-containing compositions.

Embodiment 10: The method of any one of Embodiments 1-9, further comprising generating a reverse worklist comprising a second list corresponding to the amplified DNA-containing compositions to be transferred from the PCR plate back to the original locations of a source plate.

Embodiment 11: A computer-program product tangibly embodied in a non-transitory machine-readable storage medium, including instructions configured to cause one or more data processors to perform a method for normalizing a plurality of libraries of DNA-containing compositions, the method comprising: receiving quantification information for each of a plurality of libraries of DNA-containing compositions for a first round of selection, wherein each of the libraries comprises DNA conjugates, and wherein the first round of selection causes selection of the DNA conjugates based on binding affinity to a target protein; determining a polymerase chain reaction ("PCR") cycle count specific for each of the libraries using the quantification information, wherein DNA-containing compositions of each of the libraries are determined to produce an associated pre-set amount of DNA after performing PCR with a corresponding PCR cycle count; sorting the libraries of DNA-containing compositions into bins using corresponding PCR cycle counts so determined, wherein each bin comprises a different subset of the libraries of the DNA-containing compositions determined to share a common PCR cycle count for DNA amplification, and each subset of the libraries of the DNA-containing compositions in the same bin shares a common PCR cycle count different from that of other bins of libraries; instructing a thermocycler to perform PCR, in a same run, on one of the bins with a corresponding common PCR cycle count simultaneously for a subset of the libraries of the DNA-containing compositions of the same bin; and instructing the thermocycler to perform PCR on each library of DNA-containing compositions of additional bins so that the plurality of libraries of DNA-containing compositions are normalized.

Embodiment 12: A system comprising: a data store configured to store a dataset containing quantification information of each of a plurality of libraries of DNA-containing compositions for each round of selection, wherein each of the libraries of DNA-containing compositions comprises DNA conjugates, and wherein each round of selection causes selection of the DNA conjugates based on binding affinity to a target protein; one or more data processors; and a computing device communicatively connected to the data store and configured to receive the data set, the computing device comprising a non-transitory computer readable storage medium containing instructions which, when executed on the one or more data processors, cause the one or more data processors to perform a method for normalizing a plurality of libraries of DNA-containing compositions, the method comprising: sorting the libraries of DNA-containing compositions into bins using the datasets, wherein each bin comprises a different subset of the libraries of the DNA-containing compositions determined to share a common PCR cycle count for DNA amplification using the quantification information, and each subset of the libraries of the DNA-containing compositions in the same bin shares a common PCR cycle count different from that of other bins of libraries; a thermocycler configured to perform PCR, in a same run, on one of the bins with a corresponding common PCR cycle count simultaneously for DNA-containing compositions of the same bin and to perform PCR on each library of DNA-containing compositions of additional bins so that the plurality of libraries of DNA-containing compositions are normalized.

Embodiment 13: The system of Embodiment 12, further comprising a liquid handler configured to transfer each library of the same bin from a source plate to a PCR plate, wherein each library of the same bin is amplified by PCR on the PCR plate with a common PCR cycle count for the same bin to generate amplified DNA.

Embodiment 14: The system of Embodiment 13, wherein the liquid handler is further configured to subject amplified DNA of all bins for an additional round of selection.

Embodiment 15: The system of any one of Embodiments 11-14, wherein the system further comprises a quantitative PCR unit configured to quantify each of the libraries before and after each round of selection.

Embodiment 16: The system of any one of Embodiments 11-15, wherein each of the libraries of DNA-containing compositions of any one of the bins is determined to produce a same amount of amplified DNA after performing PCR with a corresponding PCR cycle count for the same bin.

Embodiment 17: The system of any one of Embodiments 11-16, wherein the method further comprises determining a polymerase chain reaction ("PCR") cycle count specific for each library using the quantification information, wherein DNA-containing compositions of each library is determined to produce an associated pre-set amount of DNA after performing PCR with a corresponding PCR cycle count.

Embodiment 18: The system of any one of Embodiments 11-17, wherein the method further comprises correlating each bin to a corresponding PCR plate for performing PCR on DNA-containing compositions of the same bin with a corresponding common PCR cycle count on the corresponding PCR plate.

Embodiment 19: The system of any one of Embodiments 11-18, wherein the method further comprises generating a forward worklist comprising a first list corresponding to DNA-containing compositions of each bin to be transferred from original locations of a source plate into a PCR plate for performing PCR with a corresponding common PCR cycle count to generate amplified DNA.

Embodiment 20: The system of any one of Embodiments 11-19, wherein the method further comprises generating a reverse worklist comprising a second list corresponding to the amplified DNA to be transferred from the PCR plate back to the original locations of the source plate.

Embodiment 21: A method for identifying a candidate DNA conjugate for binding affinity to a target protein, comprising: receiving quantification information for each of a plurality of libraries of DNA-containing compositions for a first round of selection, wherein each of the libraries comprises DNA conjugates, and wherein the first round of selection causes selection of the DNA conjugates based on binding affinity to a target protein; determining a polymerase chain reaction ("PCR") cycle count specific for each library using the quantification information, wherein DNA-containing compositions of each library is determined to produce an associated pre-set amount of DNA after performing PCR with a corresponding PCR cycle count; sorting the libraries of DNA-containing compositions into bins using PCR cycle counts so determined, wherein each bin comprises a different subset of the libraries of the DNA-containing compositions determined to share a common PCR cycle count for DNA amplification, and each different subset of the libraries of the DNA-containing compositions in the same bin shares a common PCR cycle count different from that of other bins of libraries; instructing a thermocycler to perform PCR, in a same run, on one of the bins with a corresponding common PCR cycle count simultaneously for a subset of the libraries of the DNA-containing compositions of the same bin; instructing the thermocycler to perform PCR on each of additional bins with a corresponding common PCR cycle count so that the plurality of libraries of DNA-containing compositions are normalized to generate amplified DNA for each library; and instructing a sequencer to identify a candidate DNA conjugate for binding affinity to the target protein from the amplified DNA for each library.

Embodiment 22: The method of Embodiment 21, wherein the DNA conjugates comprise peptides.

Embodiment 23: The method of Embodiment 22, wherein the peptides comprise macrocycle peptides.

Embodiment 24: The method of any one of Embodiments 21 to 23, wherein the quantification information comprises cycle threshold (Ct) values for quantitative PCR (qPCR).

Embodiment 25: The method of any one of Embodiments 21 to 24, wherein each library of the plurality of DNA-containing compositions is stored in an individual space of a source plate.

Embodiment 26: The method of any one of Embodiments 21 to 25, wherein each of the libraries of DNA-containing compositions of one of the bins is determined to produce a same amount of DNA after performing PCR with a corresponding PCR cycle count for the same bin.

Embodiment 27: The method of any one of Embodiments 21 to 26, wherein each bin is determined to produce a same amount of DNA after performing PCR with a corresponding PCR cycle count.

Embodiment 28: The method of any one of Embodiments 21 to 27, further comprising correlating each bin to a PCR plate for performing PCR on DNA-containing compositions of the same bin with a corresponding common PCR cycle count on the PCR plate.

Embodiment 29: The method of any one of Embodiments 21 to 28, further comprising generating a forward worklist comprising a first list corresponding to DNA-containing compositions of each bin to be transferred from original locations of a source plate into a PCR plate for performing PCR with a corresponding common PCR cycle count to generate amplified DNA.

Embodiment 30: The method of any one of Embodiments 21 to 29, further comprising generating a reverse worklist comprising a second list corresponding to the amplified DNA to be transferred from the PCR plate back to the original locations of the source plate.

Embodiment 31: The method of any one of Embodiments 21 to 30, wherein additional rounds of selection comprise repeating steps of: selecting, from each of the libraries, DNA-containing compositions for binding affinity to the target protein; and amplifying DNA-containing compositions so selected.

Embodiment 32: The method of any one of Embodiments 21 to 31, wherein instructing the sequencer to identify the candidate DNA conjugate for binding affinity to the target protein comprises instructing the sequencer to sequence DNA in the candidate DNA conjugate.

Embodiment 33: The method of any one of Embodiments 21 to 32, further comprising, after each round of selection, generating new libraries of DNA-containing compositions, which comprises: performing in vitro translation on each of the libraries of a source place to produce new peptides; and performing in vitro reverse transcription on each of the libraries of the source plate to generate new peptide libraries of DNA-containing compositions.

Embodiment 34: The method of any one of Embodiments 21 to 33, further comprising quantifying each of the libraries.

Embodiment 35: The method of any one of Embodiments 21 to 34, further comprising quantifying each of the libraries using quantitative PCR (qPCR).

Embodiment 36: The method of any one of Embodiments 21 to 35, further comprising generating a heat map to visualize the quantification information for each of the libraries.

Embodiment 37: A computer-program product tangibly embodied in a non-transitory machine-readable storage medium, including instructions configured to cause one or more data processors to perform a method for monitoring quantification information of each of a plurality of libraries to detect target binding on a graphical user interface, the method comprising: receiving quantification information for each of a plurality of libraries of DNA-containing compositions for a first round of selection, wherein each of the libraries comprises DNA conjugates, and wherein the first round of selection causes selection of the DNA conjugates based on binding affinity to a target protein; determining a polymerase chain reaction ("PCR") cycle count specific for each of the libraries using the quantification information, wherein DNA-containing compositions of each of the libraries is determined to produce an associated pre-set amount of DNA after performing PCR with a corresponding PCR cycle count; sorting the libraries of DNA-containing compositions into bins using PCR cycle counts so determined, wherein each bin comprises a different subset of the libraries of the DNA-containing compositions determined to share a common PCR cycle count, and each different subset of the libraries of the DNA-containing compositions in the same bin shares a common PCR cycle count different from that of other bins of libraries; instructing a thermocycler to perform PCR, in a same run, on one of the bins with a corresponding common PCR cycle count simultaneously for the DNA-containing compositions of the same bin to generate amplified DNA-containing compositions; and identifying a candidate DNA conjugate for binding affinity to the target protein from the amplified DNA-containing compositions.

Embodiment 38: A system comprising: a data store configured to store a dataset containing quantification information of each of a plurality of libraries of DNA-containing compositions for each round of selection, wherein each of the libraries of DNA-containing compositions comprises DNA conjugates, and wherein each round of selection causes selection of the DNA conjugates based on binding affinity to a target protein; one or more data processors; and a computing device communicatively connected to the data store and configured to receive the data set, the computing device comprising a non-transitory computer readable storage medium containing instructions which, when executed on the one or more data processors, cause the one or more data processors to perform a method for identifying a candidate DNA conjugate for binding affinity to a target protein, the method comprising: determining a polymerase chain reaction ("PCR") cycle count specific for each of the libraries using the quantification information, wherein DNA-containing compositions of each of the libraries is determined to produce an associated pre-set amount of DNA after performing PCR with a corresponding PCR cycle count; and sorting the libraries of DNA-containing compositions into bins using PCR cycle counts so determined, wherein each bin comprises a different subset of the libraries of the DNA-containing compositions determined to share a common PCR cycle count, and wherein each subset of the libraries of the DNA-containing compositions in the same bin shares a common PCR cycle count different from that of other bins of libraries; and instructing a thermocycler to perform PCR, in a same run, on one of the bins with a corresponding common PCR cycle count simultaneously for DNA-containing compositions of the same bin to generate amplified DNA-containing compositions; and identifying a candidate DNA conjugate for binding affinity to the target protein from the amplified DNA-containing compositions.

Embodiment 39: The system of Embodiment 38, wherein the system further comprises a thermocycler configured to perform PCR, in a same run, on one of the bins with a corresponding common PCR cycle count simultaneously for DNA-containing compositions of the same bin.

Embodiment 40: The system of Embodiment 38 or 39, wherein the system further comprises a quantitative PCR unit configured to quantify each of libraries before and after each round of selection.

Embodiment 41: A method for monitoring quantification information of a plurality of libraries of DNA-containing compositions to detect target binding, the method comprising: a) receiving quantification information of each of a plurality of libraries of DNA-containing compositions for a first round of selection, wherein each of the libraries comprises DNA conjugates, and wherein the first round of selection causes selection of the DNA conjugates based on binding affinity to a target protein; b) generating a first window within a graphical user interface, the first window displaying the quantification information of each of the libraries for the first round of selection; and c) repeating a)-b) to generate additional windows over a plurality of subsequent rounds of selection, wherein each of the additional windows displays quantification information of each of the libraries for each of the subsequent rounds of selection so that quantification information of the DNA-containing compositions of each of the libraries for each round is monitored.

Embodiment 42: The method of Embodiment 41, wherein the quantification information of each of the libraries of DNA-containing compositions in a) and c) comprises cycle threshold (Ct) values for quantitative PCR (qPCR) input molecules, positive molecules, negative molecules, or any combination thereof.

Embodiment 43: The method of Embodiment 41 or 42, wherein the quantification information of each of the libraries of DNA-containing compositions in a) and c) comprises a percentage of positive molecules relative to input molecules.

Embodiment 44: The method of any one of Embodiments 41 to 43, further comprising displaying a selected window displaying quantification information of a selected round while hiding other windows.

Embodiment 45: The method of any one of Embodiments 41 to 44, wherein the quantification information of each of the libraries of DNA-containing compositions in a) and c) has been obtained from data scraping of qPCR data of each of the libraries.

Embodiment 46: The method of any one of Embodiments 41 to 45, wherein the DNA conjugates comprise peptides.

Embodiment 47: The method of any one of Embodiments 41 to 46, wherein the peptides comprise macrocycles.

Embodiment 48: The method of any one of Embodiments 41 to 47, wherein the first window and the additional windows comprise first graphical elements in a plurality of locations, each of the first graphical elements configured to represent each of the libraries.

Embodiment 49: The method of any one of Embodiments 41 to 48, wherein each of the libraries is in one of individual spaces of a source plate, and each of the first graphical elements is configured to horizontally and vertically correspond to each of the individual spaces of the source plate.

Embodiment 50: The method of any one of Embodiments 41 to 49, wherein each of the first graphical elements is located in the same location across different windows to represent a same well in a source plate.

Embodiment 51: The method of any one of Embodiments 41 to 50, wherein the first window and the additional windows comprise second graphical elements configured to visually distinguish quantification information of different libraries.

Embodiment 52: The method of any one of Embodiments 41 to 51, wherein the second graphical elements comprise color or numbers.

Embodiment 53: The method of any one of Embodiments 41 to 52, wherein the second graphical elements comprise numbers.

Embodiment 54: The method of any one of Embodiments 41 to 53, further comprising updating the graphic user interface to display a new window when a new round of selection is selected by a user.

Embodiment 55: The method of any one of Embodiments 41 to 54, further comprising displaying the first window and the additional windows within the same graphical user interface so that a round-to-round comparison is generated.

Embodiment 56: The method of any one of Embodiments 41 to 55, wherein the first window and the additional windows comprise third graphic elements configured to set up a filter to display quantification information of each of the libraries selected by the filter.

Embodiment 57: The method of any one of Embodiments 41 to 56, wherein the filter is a user-selected scaffold, a user-selected codon, or a user-selected target.

Embodiment 58: The method of any one of Embodiments 41 to 57, further comprising plotting a round-to-round comparison for each of the libraries of DNA-containing compositions on the graphic user interface.

Embodiment 59: A computer-program product tangibly embodied in a non-transitory machine-readable storage medium, including instructions configured to cause one or more data processors to perform a method for monitoring quantification information of libraries to detect target binding in a graphical user interface, the method comprising: a) receiving quantification information of each of a plurality of libraries of DNA-containing compositions for a first round of selection, wherein each of the libraries of DNA-containing compositions comprises DNA conjugates, and wherein the first round of selection causes selection of the DNA conjugates based on binding affinity to a target protein; b) displaying a first window within a graphical user interface, the first window containing the quantification information of each of the libraries of DNA-containing compositions after the first round of selection; and c) repeating a)-b) to generate additional windows over a plurality of subsequent rounds of selection, wherein each of the additional windows displays quantification information of each of the libraries for each of the subsequent rounds of selection so that quantification information of the DNA-containing compositions of each of the libraries for each round is monitored.

Embodiment 60: A system comprising: a data store configured to store a dataset containing quantification information of each of a plurality of libraries of DNA-containing compositions for each round of selection, wherein each of the libraries of DNA-containing compositions comprises DNA conjugates, and wherein each round of selection causes selection of the DNA conjugates based on binding affinity to a target protein; one or more data processors; and a computing device communicatively connected to the data store and configured to receive the data set, the computing device comprising a non-transitory computer readable storage medium containing instructions which, when executed on the one or more data processors, cause the one or more data processors to perform a method for displaying the quantification information of each of the libraries of DNA-containing compositions, the method comprising generating a graphical user interface comprising windows that are selected to display the quantification information of each of the libraries of DNA-containing compositions for any round of selection that has been selected to be displayed.

Embodiment 61: The system of Embodiment 60, further comprising a liquid handler configured to transfer each of the libraries from a source plate to PCR plates for PCR amplification.

Embodiment 62: The system of Embodiment 61, wherein the liquid handler is further configured to normalize each of the libraries between each two sequential rounds of selection.

Embodiment 63: The system of any one of Embodiments 60 to 62, wherein the system further comprises a thermocycler configured to amplify each of the libraries after each round of selection.

Embodiment 64: The system of any one of Embodiments 60 to 63, wherein the system further comprises a quantitative PCR unit configured to quantify each of the libraries before and after each round of selection.

Embodiment 65. A method for normalizing a polymerase chain reaction (PCR) amplification process for a plurality of samples containing DNA, the method comprising: identifying cycle data for performing the PCR amplification process for the plurality of samples, the cycle data including a corresponding cycle count for each sample of the plurality of samples; sorting the plurality of samples into a plurality of bins based on the cycle data such that cycle count variation between bins of the plurality of bins is reduced; assigning a bin cycle count to each bin of the plurality of bins, wherein the bin cycle count is unique to each bin of the plurality of bins; generating identification information for the plurality of bins; and generating an output for performing a PCR amplification of the plurality of samples using the plurality of bins and the bin cycle count for each bin of the plurality of bins.

Embodiment 66. The method of embodiment 65, wherein the plurality of samples have varying amounts of DNA and wherein after the PCR amplification process is performed such that the plurality of samples become a plurality of amplified samples, the plurality of amplified samples have normalized amounts of DNA.

Embodiment 67. The method of embodiment 65 or embodiment 66, wherein generating the identification information comprises: generating a bin identifier for each bin of the plurality of bins.

Embodiment 68. The method of any one of embodiments 65-67, wherein generating the output comprises: generating a forward worklist for a bin of the plurality of bins, the forward worklist including an order in which the set of samples in the bin is to be transferred from a source plate to a corresponding PCR plate for the bin.

Embodiment 69. The method of any one of embodiments 65-68, wherein the output further comprises instructions for a thermocycler for performing the PCR amplification process using a set of PCR plates.

Embodiment 70. The method of any one of embodiments 65-69, wherein assigning the bin cycle count comprises: generating the bin cycle count for a bin of the plurality of bins using a cycle count from a group consisting of a highest cycle count of the set of samples in the bin, an average cycle count of the set of samples, a median cycle count of the set of samples, and a sum of the highest cycle count and a selected cycle count.

Embodiment 71. The method of embodiment 70, wherein the selected cycle count is changed from a first run of the PCR amplification process to a second run of the PCR amplification process.

Embodiment 72. The method of any one of embodiments 65-71, wherein the sorting comprises: converting any non-integer cycle count of the cycle data into an integer cycle count to form modified cycle data; assigning unique integer cycle counts of the modified cycle data that are within a selected range of cycle counts to N bins; and merging adjacent bins of the N bins using a distance equation until a target number of bins is reached, wherein the target number of bins forms at least a portion of the plurality of bins.

Embodiment 73. The method of any one of embodiments 65-71, wherein identifying the cycle data comprises: receiving initial cycle data from a quantitative PCR (qPCR) system, the initial cycle data including an initial cycle count for each sample of the plurality of samples; and modifying the initial cycle count for at least one of the plurality of samples to generate the cycle data.

Embodiment 74. The method of embodiment 73, wherein the initial cycle count for a sample of the plurality of samples is an undetermined value and wherein the modifying comprises: changing the initial cycle count for the sample from the undetermined value to a preselected cycle count.

Embodiment 75. The method of any one of embodiments 73-74, wherein the modifying comprises at least one of: adding two cycles to the initial cycle count for each sample of the plurality of samples; or converting each non-integer cycle count into an integer cycle count.

Embodiment 76. The method of any one of embodiments 65-71 or 72-75, wherein the sorting comprises: distributing the plurality of samples into the plurality of bins based on a selected range of cycle counts in the cycle data.

Embodiment 77. The method of embodiment 76, wherein the distributing comprises: assigning a portion of the plurality of samples having corresponding cycle counts outside of the selected range of cycle counts to a portion of the plurality of bins; and distributing, substantially evenly, a remaining portion of the plurality of samples having corresponding cycle counts within the selected range of cycle counts between a remaining portion of the plurality of bins.

Embodiment 78. The method of any one of embodiments 65-71 or 72-75, wherein the sorting comprises: converting each non-integer cycle count in the cycle data into an integer cycle count to form modified cycle data; distributing, substantially evenly, the plurality of samples into the plurality of bins based on a selected range of cycle counts in the modified cycle data.

Embodiment 79. The method of any one of embodiments 65-78, wherein the generating the output comprises: generating a transfer output for use in transferring the set of samples in each bin of the plurality of bins to a corresponding PCR plate of a set of PCR plates using the identification information Embodiment 80. The method of any one of embodiments 65-71, wherein the plurality of samples have a plurality of corresponding cycle counts and wherein the sorting comprises: assigning a first portion of the plurality of samples having a first set of cycle counts in the plurality of corresponding below a selected low cycle count to a first bin of the plurality of bins; assigning a second portion of the plurality of samples having a second set of cycle counts above a selected high count to a last bin of the plurality of bins; and distributing a remaining portion the plurality of samples into a set of bins between the first bin and the last bin.

Embodiment 81. The method of any one of embodiments 65-71, wherein the plurality of samples have a plurality of corresponding cycle counts and wherein the sorting comprises further comprising: identifying a distribution for the plurality of corresponding cycle counts.

Embodiment 82. The method of embodiment 81, wherein identifying the distribution comprises: identifying a histogram distribution for the plurality of corresponding cycle counts, wherein between 60 percent and 100 percent of the plurality of corresponding cycle counts are within a selected range between and inclusive of a selected low cycle count and a selected high cycle count.

Embodiment 83. The method of embodiment 82, wherein the selected low cycle count is 4 cycle counts and wherein the selected high cycle count is 24 cycle counts.

Embodiment 84. The method of embodiment 82 or embodiment 83, wherein the sorting comprises: assigning any sample of the plurality of samples having the corresponding cycle count below the selected low cycle count to a first bin of the plurality of bins; and assigning any sample of the plurality of samples having the corresponding cycle count above the selected high cycle count to a last bin of the plurality of bins.

Embodiment 85. The method of embodiment 84, wherein the sorting further comprises: distributing a remaining portion of the plurality of samples between a set of bins between the first bin and the last bin.

Embodiment 86. The method of embodiment 82 or embodiment 83, wherein 100 percent of the plurality of corresponding cycle counts are within the selected range and wherein sorting the plurality of samples into the plurality of bins comprises: distributing the plurality of samples between the plurality of bins with a bias towards providing more bin separation between lower cycle counts as compared to higher cycle counts.

Embodiment 87. The method of any one of embodiments 65-71, wherein the sorting comprises: distributing the plurality of samples into the plurality of bins based on a selected range of cycle counts in the cycle data; and modifying the distribution of the plurality of samples in the plurality of bins such that any samples of the plurality of samples having corresponding cycle counts associated with a same integer value are grouped together in a same bin.

Embodiment 88. The method of embodiment 87, wherein the plurality of samples have a plurality of corresponding cycle counts and wherein two cycle counts of the plurality of corresponding cycle counts are associated with a same integer value if each of the two cycle counts contain a whole number that is the same integer value.

Embodiment 89. The method of embodiment 87, wherein the plurality of samples have a plurality of corresponding cycle counts and wherein two cycle counts of the plurality of corresponding cycle counts are associated with a same integer value if each of the two cycle counts rounds up to the same integer value.

Embodiment 90. The method of any one of embodiments 65-71, wherein the sorting comprises: sorting, based on the distribution for the plurality of cycle counts, the plurality of samples into the plurality of bins with a bias towards providing more bin separation between a portion of the plurality of cycle counts falling within one standard deviation of a mean of the plurality of cycle counts as compared to another portion of the plurality of cycle counts falling outside the one standard deviation of the mean.

Embodiment 91. The method of any one of embodiments 65-90, further comprising: transferring the set of samples in each bin of the plurality of bins to a corresponding PCR plate of a set of PCR plates based on the output; and performing the PCR amplification process using the set of PCR plates.

Embodiment 92. The method of any one of embodiments 65-91, wherein identifying the cycle data comprises: receiving the cycle data from a quantitative PCR (qPCR) system.

Embodiment 93. A system comprising: one or more data processors; and a non-transitory computer readable storage medium containing instructions which, when executed on the one or more data processors, cause the one or more data processors to perform part or all of one or more methods disclosed in embodiments 1-10, 21-36, 41-58, and 65-92.

Embodiment 94. A computer-program product tangibly embodied in a non-transitory machine-readable storage medium, including instructions configured to cause one or more data processors to perform part or all of one or more methods disclosed in embodiments 1-10, 21-36, 41-58, and 65-92.

VIII. Additional Considerations

The headers and subheaders between sections and subsections of this document are included solely for the purpose of improving readability and do not imply that features cannot be combined across sections and subsection. Accordingly, sections and subsections do not describe separate embodiments.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The ensuing description provides preferred exemplary embodiments only, and is not intended to limit the scope, applicability or configuration of the disclosure. Rather, the ensuing description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

In describing the various embodiments, the specification may have presented a method and/or process as a particular sequence of steps. However, to the extent that the method or process does not rely on the particular order of steps set forth herein, the method or process should not be limited to the particular sequence of steps described, and one skilled in the art can readily appreciate that the sequences may be varied and still remain within the spirit and scope of the various embodiments.

All references cited herein, including patent applications, patent publications, and UniProtKB/Swiss-Prot Accession numbers are herein incorporated by reference in their entirety, as if each individual reference were specifically and individually indicated to be incorporated by reference.

What is claimed is:

1. A method for normalizing a plurality of libraries of DNA-containing compositions, comprising:
    receiving quantification information for each of a plurality of libraries of DNA-containing compositions for a first round of selection, wherein each of the libraries comprises DNA conjugates, and wherein the first round of selection causes selection of the DNA conjugates based on binding affinity to a target protein;
    determining a polymerase chain reaction ("PCR") cycle count specific for each of the libraries using the quantification information, wherein DNA-containing compositions of each of the libraries are determined to produce an associated pre-set amount of DNA after performing PCR with a corresponding PCR cycle count;
    sorting the libraries of DNA-containing compositions into bins using corresponding PCR cycle counts so determined, wherein each bin comprises a different subset of the libraries of the DNA-containing compositions determined to share a common PCR cycle count for DNA amplification, and each subset of the libraries of the DNA-containing compositions in the same bin shares a common PCR cycle count different from that of other bins of libraries;
    instructing a thermocycler to perform PCR, in a same run, on one of the bins with a corresponding common PCR cycle count simultaneously for a subset of the libraries of DNA-containing compositions of the same bin; and
    instructing the thermocycler to perform PCR on each of additional bins with a corresponding common PCR cycle count so that the plurality of libraries of DNA-containing compositions are normalized.

2. The method of claim 1, wherein the DNA conjugates comprise peptides.

3. The method of claim 2, wherein the peptides comprise macrocycles.

4. The method of claim 1, wherein the quantification information comprises cycle threshold (Ct) values for quantitative PCR (qPCR).

5. The method of claim 1, wherein at least one of the bins includes more than one libraries of the DNA-containing compositions.

6. The method of claim 1, wherein each of the libraries of DNA-containing compositions of any one of the bins is determined to produce a substantially identical amount of amplified DNA after performing PCR with a corresponding PCR cycle count for the same bin.

7. The method of claim 1, further comprising instructing a thermocycler to perform PCR on each of DNA-containing compositions of an additional bin with an additional corresponding common PCR cycle count simultaneously to produce additional amplified DNA.

8. The method of claim 1, further comprising correlating each bin to a corresponding PCR plate for performing PCR on DNA-containing compositions of the same bin with a corresponding common PCR cycle count on the corresponding PCR plate.

9. The method of claim 1, further comprising generating a forward worklist comprising a first list corresponding to DNA-containing compositions of each bin to be transferred from original locations of a source plate into a PCR plate to generate amplified DNA-containing compositions.

10. The method of claim 9, further comprising generating a reverse worklist comprising a second list corresponding to the amplified DNA-containing compositions to be transferred from the PCR plate back to the original locations of a source plate.

* * * * *